United States Patent
Watabe et al.

(10) Patent No.: US 11,024,809 B2
(45) Date of Patent: Jun. 1, 2021

(54) LIGHT-EMITTING ELEMENT, LIGHT-EMITTING DEVICE, ELECTRONIC DEVICE, LIGHTING DEVICE, AND ORGANOMETALLIC COMPLEX

(71) Applicant: Semiconductor Energy Laboratory Co., Ltd., Kanagawa-ken (JP)

(72) Inventors: Takeyoshi Watabe, Kanagawa (JP); Satomi Watabe, Kanagawa (JP); Hideko Yoshizumi, Kanagawa (JP); Tomoka Hara, Kanagawa (JP); Yui Yamada, Kanagawa (JP); Takahiro Ishisone, Kanagawa (JP); Hiromitsu Kido, Kanagawa (JP); Kunihiko Suzuki, Kanagawa (JP); Satoshi Seo, Kanagawa (JP)

(73) Assignee: Semiconductor Energy Laboratory Co., Ltd.

( * ) Notice: Subject to any disclaimer, the term of this patent is extended or adjusted under 35 U.S.C. 154(b) by 188 days.

(21) Appl. No.: 15/687,861

(22) Filed: Aug. 28, 2017

(65) Prior Publication Data
US 2018/0062084 A1    Mar. 1, 2018

(30) Foreign Application Priority Data

Aug. 29, 2016    (JP) .............................. JP2016-167185

(51) Int. Cl.
*H01L 51/00*    (2006.01)
*C07D 213/06*    (2006.01)
(Continued)

(52) U.S. Cl.
CPC ........ *H01L 51/0067* (2013.01); *C07D 213/06* (2013.01); *C07D 249/10* (2013.01);
(Continued)

(58) Field of Classification Search
None
See application file for complete search history.

(56) References Cited

U.S. PATENT DOCUMENTS

| 7,192,326 B2 | 3/2007 | Suzuki et al. |
| 7,332,858 B2 | 2/2008 | Nomura et al. |

(Continued)

FOREIGN PATENT DOCUMENTS

| CN | 103168043 A | 6/2013 |
| CN | 107710441 A | 2/2018 |

(Continued)

OTHER PUBLICATIONS

Feldman et al. "Highly Quantum Efficient Phosphorescent Sky Blue Emitters Based on Diastereomeric Iridium (III) Complexes of Atropisomeric 5-Aryl-4H-1,2,4-triazole Ligands" Organometallics, 2015, 34, 3665-3669. (Year: 2015).*

(Continued)

*Primary Examiner* — Robert S Loewe
(74) *Attorney, Agent, or Firm* — Husch Blackwell LLP

(57) ABSTRACT

In a light-emitting element, a layer including an organic compound includes a light-emitting layer; the light-emitting layer includes a tris iridium complex; and on the assumption that there is a rectangle which covers the iridium complex and in which at least one atom of the iridium complex is located over each of four sides when the iridium complex is two-dimensionally seen from a direction of a C3 symmetry axis of the iridium complex, $A \times B/C^2$ is greater than or equal to 2.5, where A represents a maximum length of a long side of the rectangle, B represents a length of a short side of the rectangle when the length of the long side of the rectangle is A, and C represents a width in the direction of the C3 symmetry axis when the iridium complex is two-dimensionally seen from a normal direction of the C3 symmetry axis.

17 Claims, 39 Drawing Sheets

(51) Int. Cl.
*C07D 249/10* (2006.01)
*C09K 11/06* (2006.01)
*C07F 15/00* (2006.01)
*H01L 51/50* (2006.01)
*G01R 33/46* (2006.01)

(52) U.S. Cl.
CPC .......... *C07F 15/0033* (2013.01); *C09K 11/06* (2013.01); *H01L 51/0085* (2013.01); *G01R 33/46* (2013.01); *H01L 51/5016* (2013.01)

(56) References Cited

U.S. PATENT DOCUMENTS

| | | | | |
|---|---|---|---|---|
| 8,227,798 | B2 * | 7/2012 | Kai | H01L 51/0061 257/40 |
| 8,404,364 | B2 * | 3/2013 | Tanaka | C07F 15/0033 257/40 |
| 8,921,548 | B2 | 12/2014 | Inoue et al. | |
| 9,184,398 | B2 | 11/2015 | Inoue et al. | |
| 9,960,363 | B2 | 5/2018 | Eum et al. | |
| 9,985,223 | B2 | 5/2018 | Inoue et al. | |
| 2007/0085073 | A1 * | 4/2007 | Inoue | C07F 15/0046 257/40 |
| 2007/0176543 | A1 | 8/2007 | Suzuki et al. | |
| 2008/0305361 | A1 * | 12/2008 | Inoue | C07F 15/0033 428/691 |
| 2009/0184631 | A1 * | 7/2009 | Kim | H05B 33/14 313/504 |
| 2010/0247747 | A1 | 9/2010 | Yamazaki | |
| 2011/0057559 | A1 * | 3/2011 | Xia | C07F 15/0033 313/504 |
| 2011/0127503 | A1 * | 6/2011 | Takahashi | H01L 51/0007 257/40 |
| 2011/0291083 | A1 * | 12/2011 | Kim | C07D 249/08 257/40 |
| 2012/0025697 | A1 * | 2/2012 | Kadoma | C07D 471/04 313/504 |
| 2012/0098417 | A1 * | 4/2012 | Inoue | H05B 33/14 313/504 |
| 2012/0126212 | A1 | 5/2012 | Yamazaki et al. | |
| 2012/0133273 | A1 * | 5/2012 | Inoue | C07F 15/0033 313/504 |
| 2012/0248969 | A1 * | 10/2012 | Inoue | C07F 15/0033 313/504 |
| 2013/0049576 | A1 * | 2/2013 | Katakura | H05B 33/20 313/504 |
| 2013/0221278 | A1 * | 8/2013 | Inoue | C07F 15/0033 252/301.16 |
| 2013/0256646 | A1 * | 10/2013 | Fennimore | C07D 239/26 257/40 |
| 2013/0277654 | A1 * | 10/2013 | Seo | H01L 51/5016 257/40 |
| 2013/0320377 | A1 * | 12/2013 | Yamazaki | H01L 51/504 257/98 |
| 2013/0323869 | A1 * | 12/2013 | Inoue | H01L 51/0074 438/46 |
| 2013/0328037 | A1 * | 12/2013 | Oshiyama | C07F 9/5022 257/40 |
| 2013/0341602 | A1 * | 12/2013 | Hikime | H01L 51/0074 257/40 |
| 2014/0151660 | A1 * | 6/2014 | Kamtekar | C09D 165/00 257/40 |
| 2014/0306203 | A1 * | 10/2014 | Akino | H01L 51/0085 257/40 |
| 2014/0339524 | A1 * | 11/2014 | Shitagaki | H01L 51/5028 257/40 |
| 2014/0353654 | A1 | 12/2014 | Yamazaki et al. | |
| 2015/0014675 | A1 * | 1/2015 | Feldman | C07F 15/0033 257/40 |
| 2015/0076466 | A1 * | 3/2015 | Park | H01L 51/0085 257/40 |
| 2015/0137051 | A1 * | 5/2015 | Jung | C07F 15/0033 252/519.21 |
| 2015/0236278 | A1 * | 8/2015 | Bryman | H01L 51/0085 257/40 |
| 2015/0243909 | A1 * | 8/2015 | Feldman | C07F 15/0033 257/40 |
| 2016/0075718 | A1 | 3/2016 | Mitsumori et al. | |
| 2016/0181550 | A1 * | 6/2016 | Yamada | H01L 51/0085 257/40 |
| 2016/0372688 | A1 * | 12/2016 | Seo | C09K 11/06 |
| 2017/0025630 | A1 * | 1/2017 | Seo | H01L 27/3244 |
| 2017/0155072 | A1 | 6/2017 | Hashimoto et al. | |
| 2017/0338435 | A1 | 11/2017 | Seo et al. | |
| 2018/0006221 | A1 | 1/2018 | Seo et al. | |
| 2018/0053900 | A1 | 2/2018 | Eum et al. | |
| 2020/0185617 | A1 | 6/2020 | Eum et al. | |
| 2020/0185618 | A1 | 6/2020 | Eum et al. | |
| 2020/0350503 | A1 | 11/2020 | Seo et al. | |

FOREIGN PATENT DOCUMENTS

| | | | | |
|---|---|---|---|---|
| CN | 107851727 A | | 3/2018 | |
| EP | 3 239 136 A2 | | 11/2017 | |
| EP | 3 239 271 A1 | | 11/2017 | |
| EP | 3 660 006 A1 | | 6/2020 | |
| JP | 2004349224 A | * | 12/2004 | H05B 33/14 |
| JP | 2008147400 A | * | 6/2008 | H01L 51/50 |
| JP | 2012-129509 A | | 7/2012 | |
| WO | WO 2012/053627 A1 | | 4/2012 | |
| WO | WO-2013031794 A1 | * | 3/2013 | H01L 51/0085 |
| WO | WO-2015175130 A1 | * | 11/2015 | C07F 15/0033 |
| WO | WO 2016/105050 A1 | | 6/2016 | |
| WO | WO 2016/203350 A1 | | 12/2016 | |
| WO | WO 2017/013534 A1 | | 1/2017 | |

OTHER PUBLICATIONS

Kim et al. "Homoleptic Tris-Cyclometalated Iridium Complexes with Substituted o-Carboranes: Green Phosphorescent Emitters for Highly Efficient Solution-Processed Organic Light-Emitting Diodes" Inorg. Chem. 2016, 55, 909-917. (Year: 2016).*

Yokoyama, D., "Molecular Orientation in Small-Molecule Organic Light-Emitting Diodes," Journal of Materials Chemistry, Dec. 28, 2011, vol. 21, No. 48, pp. 19187-19202.

Liehm, P. et al., "Comparing the Emissive Dipole Orientation of Two Similar Phosphorescent Green Emitter Molecules in Highly Efficient Organic Light-Emitting Diodes," Applied Physics Letters, Dec. 17, 2012, vol. 101, No. 25, pp. 253304-1-253304-4.

Chinese Office Action (Application No. 201710741317.4) dated Nov. 24, 2020.

* cited by examiner

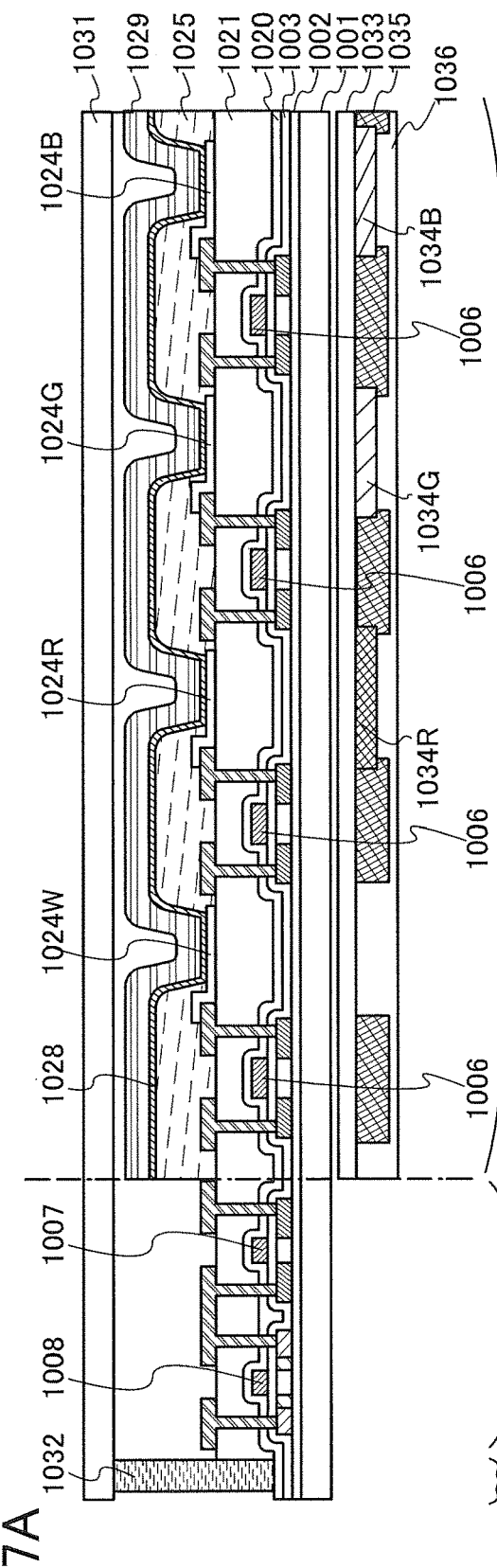
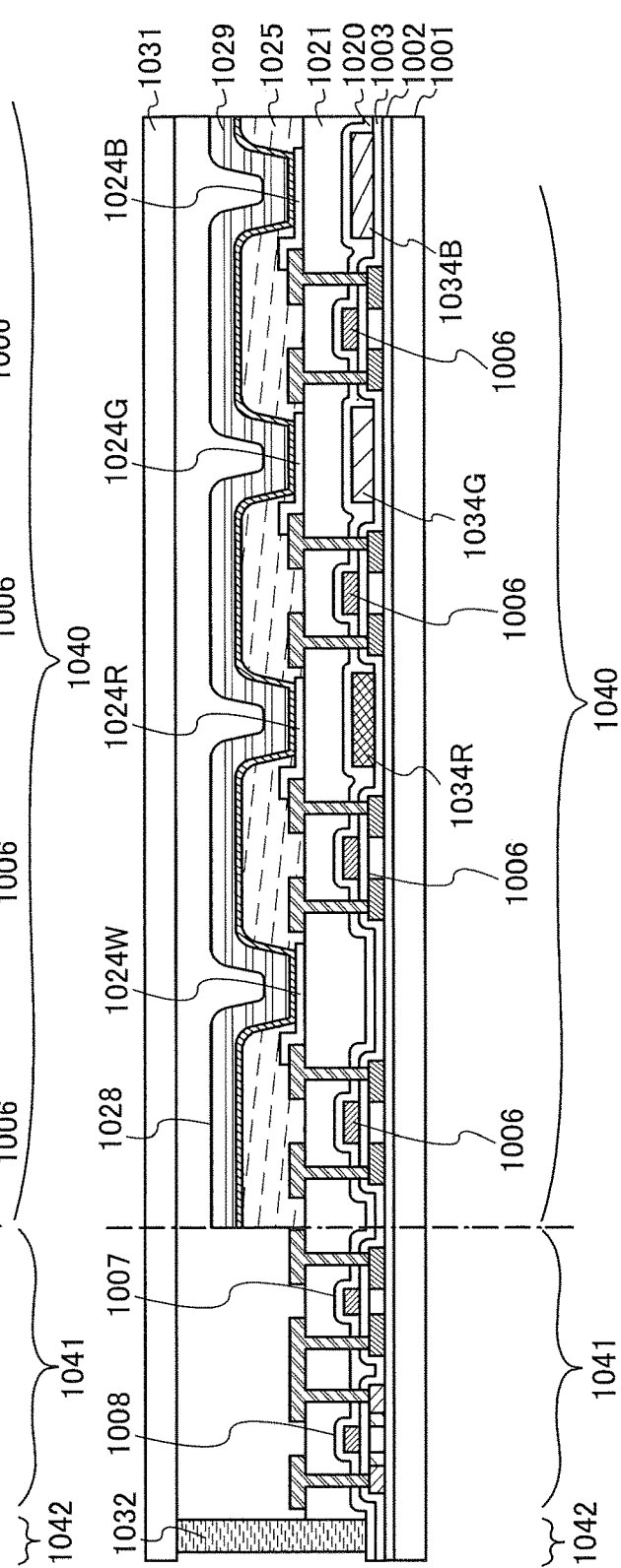
FIG. 7A
FIG. 7B

LIGHT-EMITTING ELEMENT, LIGHT-EMITTING DEVICE, ELECTRONIC DEVICE, LIGHTING DEVICE, AND ORGANOMETALLIC COMPLEX

BACKGROUND OF THE INVENTION

1. Field of the Invention

One embodiment of the present invention relates to a light-emitting element, a display module, a lighting module, a display device, a light-emitting device, an electronic device, and a lighting device. Note that one embodiment of the present invention is not limited to the above technical field. The technical field of one embodiment of the invention disclosed in this specification and the like relates to an object, a method, or a manufacturing method. Furthermore, one embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting device, a lighting device, a power storage device, a storage device, an imaging device, a method for driving any of them, and a method for manufacturing any of them.

2. Description of the Related Art

Light-emitting elements (organic EL elements) including organic compounds and utilizing electroluminescence (EL) have been put to more practical use. In the basic structure of such light-emitting elements, an organic compound layer containing a light-emitting material (an EL layer) is interposed between a pair of electrodes. Carriers are injected by application of voltage to the element, and recombination energy of the carriers is used, whereby light emission can be obtained from the light-emitting material.

Since such light-emitting elements are of self-light-emitting type, light-emitting elements have advantages over liquid crystal displays when used as pixels of a display in that visibility of pixels is high and backlight is not required. Displays including such light-emitting elements are also highly advantageous in that they can be thin and lightweight. Moreover, such a light-emitting element also has a feature that response speed is extremely fast.

In addition, displays including such light-emitting elements can be changed in shape relatively easily, which can significantly increase the flexibility in the design of displays and mobile devices.

In such light-emitting elements, light-emitting layers can be successively formed two-dimensionally, so that planar light emission can be obtained. This feature is difficult to realize with point light sources typified by incandescent lamps and LEDs or linear light sources typified by fluorescent lamps. Thus, light-emitting elements also have great potential as planar light sources, which can be applied to lighting devices and the like.

Displays or lighting devices including light-emitting elements can be suitably used for a variety of electronic devices as described above, and research and development of light-emitting elements have progressed for higher efficiency or longer lifetimes.

Patent Document 1 discloses a light-emitting element whose light extraction efficiency is improved by depositing light-emitting substances such that their orientations are aligned with each other to control the direction of light emission.

REFERENCE

Patent Document

[Patent Document 1] Japanese Published Patent Application No. 2012-129509

Non-Patent Document

[Non-Patent Document 1] D. Yokoyama, *Journal of Materials Chemistry*, 21, 19187, 2011.

[Non-Patent Document 2] P. Liehm, et.al, *Applied Physics Letters*, 101, 253304, 2012.

SUMMARY OF THE INVENTION

An object of one embodiment of the present invention is to provide a novel light-emitting element. Another object of one embodiment of the present invention is to provide a light-emitting element with high emission efficiency. Another object of one embodiment of the present invention is to provide light-emitting elements with a long lifetime. Another object of one embodiment of the present invention is to provide a novel organometallic complex. Another object of one embodiment of the present invention is to provide a novel organometallic complex with a large parameter of planarity.

Another object of one embodiment of the present invention is to provide a light-emitting device, an electronic device, and a display device each with low power consumption. Another object of one embodiment of the present invention is to provide a highly reliable light-emitting device, a highly reliable electronic device, and a highly reliable display device.

It is only necessary that at least one of the above-described objects be achieved in the present invention.

One embodiment of the present invention is a light-emitting element including a first electrode, a second electrode, and a layer including an organic compound. The layer including an organic compound is located between the first electrode and the second electrode. The layer including an organic compound includes a light-emitting layer. The light-emitting layer includes a tris iridium complex. On the assumption that there is a rectangle which covers the iridium complex and in which at least one atom of the iridium complex is located over each of four sides when the iridium complex is two-dimensionally seen from a direction of a C3 symmetry axis of the iridium complex, $A \times B/C^2$ is greater than or equal to 2.5, where A represents a maximum length of a long side of the rectangle, B represents a length of a short side of the rectangle when the length of the long side of the rectangle is A, and C represents a width in the direction of the C3 symmetry axis when the iridium complex is two-dimensionally seen from a normal direction of the C3 symmetry axis.

Another embodiment of the present invention is the light-emitting element with the above structure in which the iridium complex includes a ligand having a triazole skeleton or a ligand having an imidazole skeleton.

Another embodiment of the present invention is the light-emitting element with the above structure in which $A \times B/C^2$ is greater than or equal to 2.8.

Another embodiment of the present invention is the light-emitting element with the above structure in which A×B/C² is greater than or equal to 3.0.

Another embodiment of the present invention is a light-emitting device including the above-mentioned light-emitting element and a transistor or a substrate.

Another embodiment of the present invention is an electronic device including the above-mentioned light-emitting device and a sensor, an operation button, a speaker, or a microphone.

Another embodiment of the present invention is a lighting device including the above-mentioned light-emitting device and a housing.

Another embodiment of the present invention is an organometallic complex represented by the following structural formula.

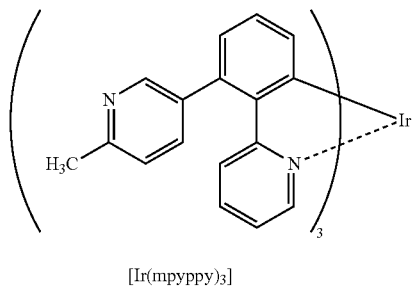

[Ir(mpyppy)₃]

Another embodiment of the present invention is an organometallic complex represented by the following structural formula.

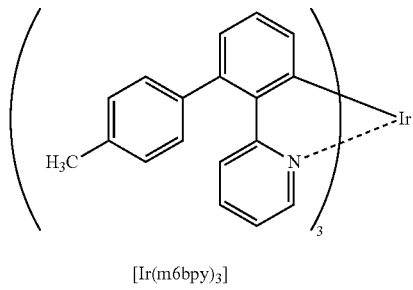

[Ir(m6bpy)₃]

Note that the light-emitting device in this specification includes, in its category, an image display device that uses a light-emitting element. The light-emitting device may include a module in which a light-emitting element is provided with a connector such as an anisotropic conductive film or a tape carrier package (TCP), a module in which a printed wiring board is provided at the end of a TCP, and a module in which an integrated circuit (IC) is directly mounted on a light-emitting element by a chip on glass (COG) method. The light-emitting device may also be included in lighting equipment and the like.

In one embodiment of the present invention, a novel light-emitting element can be provided. In another embodiment of the present invention, a light-emitting element with a long lifetime can be provided. In another object of one embodiment of the present invention, a light-emitting element with high emission efficiency can be provided. In another embodiment of the present invention, a novel organometallic complex can be provided. In another embodiment of the present invention, a novel organometallic complex with a large parameter of planarity can be provided.

In another embodiment of the present invention, a highly reliable light-emitting device, a highly reliable electronic device, and a highly reliable display device can be provided. In another embodiment of the present invention, a light-emitting device, an electronic device, and a display device each with low power consumption can be provided.

Note that the description of these effects does not preclude the existence of other effects. One embodiment of the present invention does not necessarily achieve all the effects listed above. Other effects will be apparent from and can be derived from the description of the specification, the drawings, the claims, and the like.

BRIEF DESCRIPTION OF THE DRAWINGS

FIGS. 7A and 7B are conceptual diagrams of an active matrix light-emitting device.

FIGS. 11A, 11B1, 11B2, 11C, and 11D each illustrate an electronic device.

DETAILED DESCRIPTION OF THE INVENTION

Embodiments and examples of the present invention will be described below with reference to the drawings. It will be readily appreciated by those skilled in the art that modes and details of the present invention can be modified in various ways without departing from the spirit and scope of the present invention. Thus, the present invention should not be construed as being limited to the description in the following embodiments and examples.

Figure 3A:
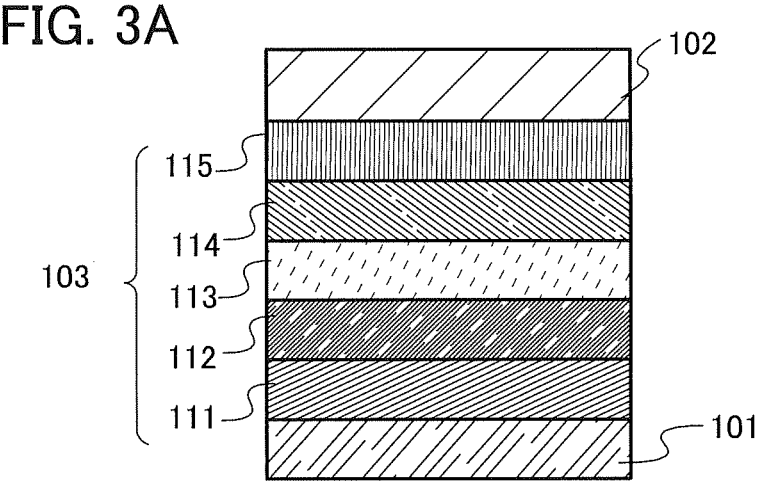
FIGS. 3A to 3C are each a conceptual diagram of a light-emitting element.

FIG. 3A illustrates a light-emitting element of one embodiment of the present invention. The light-emitting element of one embodiment of the present invention includes a first electrode 101, a second electrode 102, and an EL layer 103. The EL layer 103 includes a light-emitting layer 113. Note that the EL layer 103 may include other functional layers such as a hole-injection layer, a hole-transport layer, an electron-transport layer, and an electron-injection layer.

The light-emitting layer 113 of the light-emitting element of one embodiment of the present invention includes a tris iridium complex. It is preferable that the light-emitting layer 113 further include a host material and that the iridium complex be dispersed in the host material.

Here, the present inventors have found that it is possible to obtain high emission efficiency of the light-emitting element when an iridium complex with a structure having high planarity is used as the iridium complex.

Figure 1A:
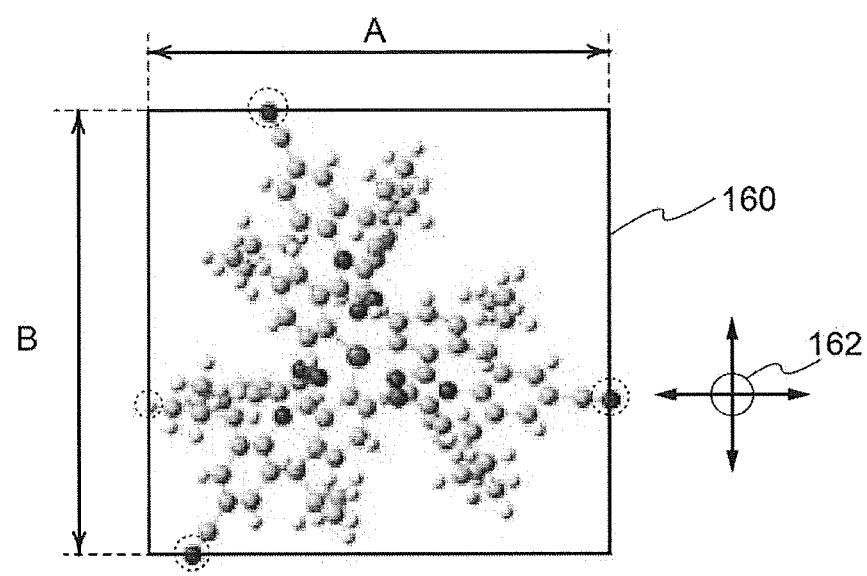
FIGS. 1A and 1B show a method for calculating a parameter of planarity.

A method for calculating the planarity of the iridium complex is described with reference to FIGS. 1A and 1B.

Figure 1B:
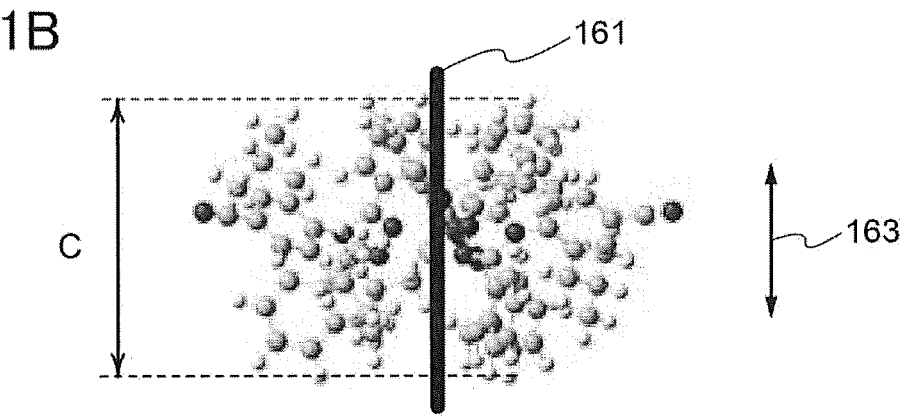

The iridium complex used in the light-emitting element of one embodiment of the present invention is a facial tris iridium complex; therefore, a C3 symmetry axis 161 exists (FIG. 1B). FIG. 1A illustrates the iridium complex which is seen two-dimensionally from a direction 163 of the C3 symmetry axis 161. In FIG. 1A, on the assumption that there is a rectangle 160 which covers the iridium complex and in which at least one atom (corresponding to an atom inside a dashed-line circle in FIG. 1A) of the iridium complex is located on each side, the lengths of a long side and a short side of the rectangle 160 are represented as A and B, respectively, when the length of the long side is maximized. FIG. 1B illustrates the iridium complex which is seen two-dimensionally from a normal direction 162 of the C3 symmetry axis 161. In FIG. 1B, a width (thickness) in the direction 163 of the C3 symmetry axis is represented as C. With the use of the three variables (A, B, and C), a calculation formula, $A \times B/C^2$, is obtained. A value obtained by the calculation formula $A \times B/C^2$ corresponds to a value which represents the planarity of the iridium complex. Note that the larger the value is, the higher the planarity is.

Here, the value of $A \times B/C^2$, which is a parameter of the planarity, was calculated for the following nine iridium complexes: tris{2-[5-(2-methylphenyl)-4-(3,3',5,5'-tetramethyl-1,1'-biphenyl-4-yl)-4H-1,2,4-triazol-3-yl-κN$^2$]phenyl-κC}iridium(III) (abbreviation: [Ir(mpptz-tetmb)$_3$]; Structural formula (100)); tris[2-(6-methyl-5-phenyl-4-pyrimidinyl-κN$^3$)phenyl-κC]iridium(III) (abbreviation: [Ir(mpppm)$_3$]; Structural formula (101)); tris{2-[1-(4-cyano-2,6-diisobutylphenyl)-1H-imidazol-2-yl-κN$^3$]phenyl-κC}iridium(III) (abbreviation: [Ir(pim-diBuCNp)$_3$]; Structural formula (102)); tris{4'-cyano-2',6'-dimethyl-3-[3-methyl-1-(2,4,6-trimethylphenyl)-1H-1,2,4-triazol-5-yl-κN$^4$]-1,1'-biphenyl-4-yl-κC}iridium(III) (abbreviation: [Ir(MdmCN5btz1-tmp)$_3$]; Structural formula (103)); tris{2-[4-(4-cyano-2,6-diisobutylphenyl)-5-(2-methylphenyl)-4H-1,2,4-triazol-3-yl-κN$^2$]phenyl-κC}iridium(III) (abbreviation: [Ir(mpptz-diBuCNp)$_3$]; Structural formula (104)); tris{2-[5-(2-methylphenyl)-4-(2,4,6-trimethylphenyl)-4H-1,2,4-triazol-3-yl-κN$^2$]phenyl-κC}iridium(III) (abbreviation: [Ir(mpptz-tmp)$_3$]; Structural formula (105)); tris{2-[5-(2-methylphenyl)-4-(2,6-diisopropylphenyl)-4H-1,2,4-triazol-3-yl-κN$^2$]phenyl-κC}iridium(III) (abbreviation: [Ir(mpptz-diPrp)$_3$]; Structural formula (106)); tris{2-[5-(2-methylphenyl)-4-(2,6-dimethylphenyl)-4H-1,2,4-triazol-3-yl-κN$^2$]phenyl-κC}iridium(III) (abbreviation: [Ir(mpptz-dmp)₃]; Structural formula (107)); and tris(2-phenylpyridinato-N,C²')iridium(III) (abbreviation: [Ir(ppy)₃]; Structural formula (108)).
The structural formulae (100) to (108) of the tris iridium complexes are shown below.
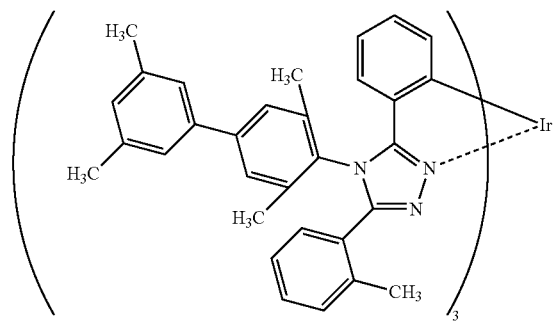
(100) Ir(mpptz-tetmb)₃
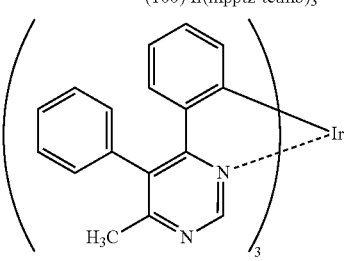
(101) Ir(mpppm)₃
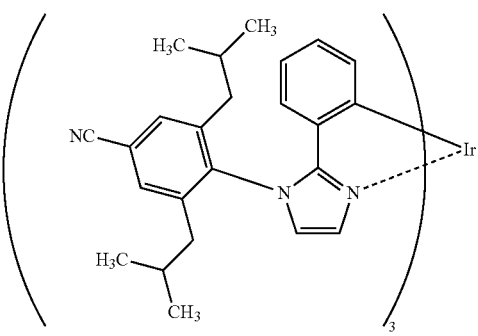
(102) Ir(pim-diBuCNp)₃
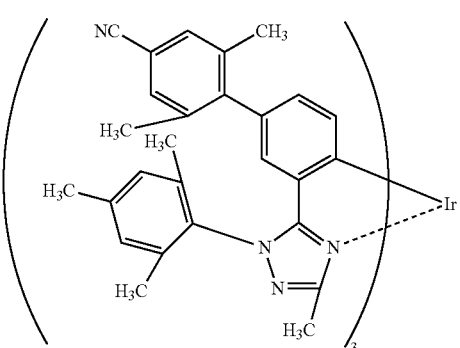
(103) Ir(MdmCN5btz1-tmp)₃
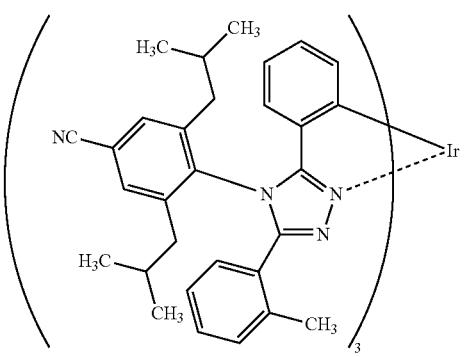
(104) Ir(mpptz-diBuCNp)₃
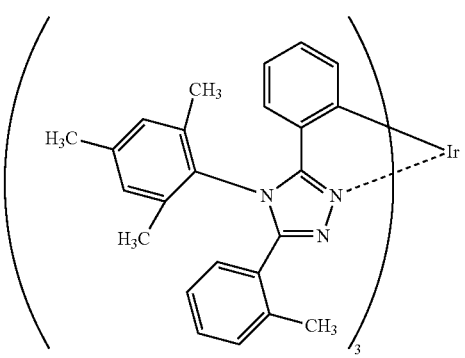
(105) Ir(mpptz-tmp)₃
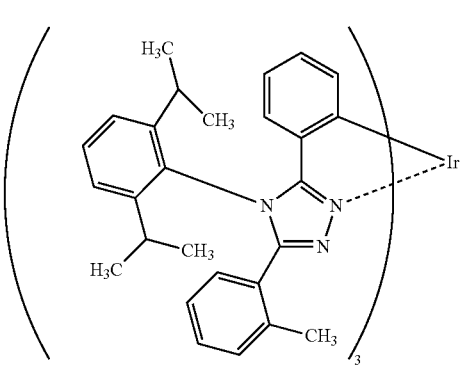
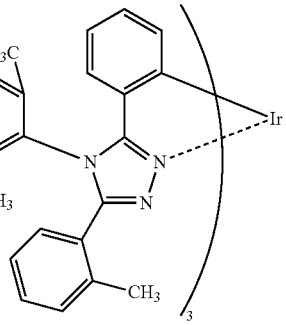
(107) Ir(mpptz-dmp)₃

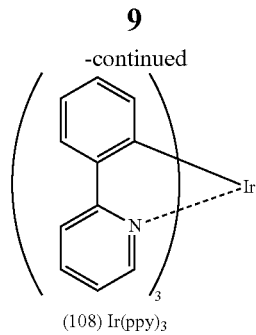

(108) Ir(ppy)₃

Note that the parameter of the planarity was obtained in such a manner that the values of A, B, and C were determined by the above method for a molecular structure which was optimized by molecular orbital calculations.

The molecular orbital calculations were performed with a high-performance computer (ICE X manufactured by SGI Japan, Ltd.), and Gaussian 09 was used as a quantum chemistry computational program. As a basis function, 6-311G(d,p) was used for hydrogen, carbon, and nitrogen atoms, and LanL2DZ was used for an iridium atom. The most stable structure in the singlet ground state was calculated using the density functional theory (DFT). As a functional, B3PW91 was used. By the above basis function, for example, the basis function of is represented with three Gaussian functions and the basis functions of 1s' and 1s" represented with one Gaussian function are considered for a hydrogen atom; the basis function 1s is represented with six Gaussian functions, the basis functions of 2s, $2p_x$, $2p_y$, and $2p_z$, represented with three Gaussian functions, and the basis functions of 2s', 2s'", $2p_x$', $2p_y$', $2p_z$', $2p_x$", $2p_y$", and $2p_z$" are considered for a carbon atom. Here, the variations in the size of the orbit are represented with a prime(s). Furthermore, to improve calculation accuracy, the p functions ($p_x$, $p_y$, and $p_z$) and the d functions ($d_{xy}$, $d_{yz}$, $d_{zx}$, $d_z^2$, and $d_{x^2-y^2}$) were added as polarization basis sets to a hydrogen atom and carbon and nitrogen atoms, respectively. Note that symmetry was C3. The results are shown in Table 1.

TABLE 1

| | A [Å] | B [Å] | C [Å] | A × B/C² [—] |
|---|---|---|---|---|
| Ir(mpptz-tetmb)₃ (100) | 25.4 | 22.5 | 10.4 | 5.3 |
| Ir(mpppm)₃ (101) | 15.9 | 14.6 | 7.3 | 4.3 |
| Ir(pim-diBuCNp)₃ (102) | 18.4 | 18.3 | 8.9 | 4.3 |
| Ir(MdmCN5btz1-tmp)₃ (103) | 19.9 | 17.5 | 10.1 | 3.4 |
| Ir(mpptz-diBuCNp)₃ (104) | 18.9 | 18.0 | 10.5 | 3.1 |
| Ir(mpptz-tmp)₃ (105) | 17.9 | 17.0 | 10.4 | 2.8 |
| Ir(mpptz-diPrp)₃ (106) | 16.3 | 15.5 | 10.4 | 2.4 |
| Ir(mpptz-dmp)₃ (107) | 16.5 | 15.3 | 10.4 | 2.4 |
| Ir(ppy)₃ (108) | 10.5 | 9.3 | 7.3 | 1.9 |

In this manner, although all the iridium complexes are of the tris type, the planarity significantly differs among the tris iridium complexes depending on their structures. Specifically, [Ir(ppy)₃] with a small parameter of planarity has a nearly spherical shape, whereas [Ir(mpptz-tetmb)₃] with a large parameter of planarity has high planarity. As described above, the inventors of the present invention have found that the light-emitting element with the iridium complex having a large parameter of planarity, i.e., high planarity, specifically, the iridium complex having a value of A×B/C² of larger than or equal to 2.5, emits light with extremely high emission efficiency.

For example, a light-emitting element which was formed using tris{2-[4-(4-cyano-2,6-diisobutylphenyl)-5-(2-methylphenyl)-4H-1,2,4-triazol-3-yl-κN²]phenyl-κC}iridium (III) (abbreviation: [Ir(mpptz-diBuCNp)₃]) in which the value was 3.1 achieved an extremely high external quantum efficiency of 33.8% even without any special light-extraction structure.

The planarity of typical tris iridium complexes and the external quantum efficiencies of light-emitting elements formed using the iridium complexes are listed in the following table. Note that the external quantum efficiency is calculated under assumption of Lambertian. A special structure for light extraction, e.g., a high refractive index substrate, is not used.

TABLE 2

| | A [Å] | B [Å] | C [Å] | A × B/C² [—] | External quantum efficiency (%) |
|---|---|---|---|---|---|
| Ir(pim-diBuCNp)₃ (102) | 18.4 | 18.3 | 8.9 | 4.3 | 33.8 |
| Ir(MdmCN5btz1-tmp)₃ (103) | 19.9 | 17.5 | 10.1 | 3.4 | 31.1 |
| Ir(mpptz-diBuCNp)₃ (104) | 18.9 | 18.0 | 10.5 | 3.1 | 34.5 |
| Ir(mpptz-tmp)₃ (105) | 17.9 | 17.0 | 10.4 | 2.8 | 29.3 |
| Ir(mpptz-diPrp)₃ (106) | 16.3 | 15.5 | 10.4 | 2.4 | 27.7 |

As shown in the above, there is a correlation between the planarity and the external quantum efficiency. In particular, the iridium complexes whose values of A×B/C², the parameters of planarity, are greater than or equal to 2.5 exhibit an extremely high external quantum efficiency of approximately 30%. The value of A×B/C² is preferably greater than or equal to 2.5, further preferably greater than or equal to 2.8, still further preferably greater than or equal to 3.0.

This is because the orientation of the iridium complex becomes high when the light-emitting layer is formed, owing to the high planarity of the iridium complex. The relationship between the orientation of a light-emitting substance and external quantum efficiency is described below.

One of factors which greatly influence external quantum efficiency is light extraction efficiency (χ). The light extraction efficiency (χ) is generally 20% to 30% in an organic EL element over a glass substrate, although it depends on the structure or stacked layers of a light-emitting device. However, the above value is based on the assumption that light emission is isotropic; therefore, this value changes when light emission is anisotropic.

Light emission of a light-emitting material is generated in the direction perpendicular to the transition dipole of a molecule. Accordingly, the light extraction efficiency (x) can be improved by controlling the orientation state of the molecule.

The inventors of the present invention estimated molecular orientation of the iridium complex from the light-emission state of the element. The radiation angle dependence of the emission intensity (spatial emission pattern) of the light-emitting element depends on the spatial distribution of a transition dipole of the light-emitting material. If this spatial distribution can be analyzed, the orientation state of the light-emitting element can be obtained. In this method, light emission of the light-emitting element is observed and analyzed; thus, as long as the light-emitting material emits light, it is possible to obtain the orientation state of the light-emitting material in the light-emitting layer even when the concentration of the material is low.

In practice, the measured angle dependence of the emission intensity and the angle dependence of the emission intensity calculated by assuming, with a device simulator, a parameter α (see Formula (1) below) which represents the orientation state of a light-emitting molecule are compared; in this manner, an appropriate value of the parameter α which represents the orientation state of a molecule can be estimated to obtain the orientation state of a light-emitting substance in a light-emitting element (see Non-Patent Document 2). The inventors of the present invention also focused their attention to the shape of the emission spectrum obtained by the device simulator, and compared the measured and calculated values of the shape of the emission spectrum and a change in the shape of the emission spectrum depending on the angle to predict appropriate values. As the emission intensity in the measurement and simulation, not the emission intensity at a particular wavelength but the integrated intensity of the emission spectrum is used. By these methods which the inventors of the present invention employed, the parameter α can be estimated highly accurately, unlike in the method disclosed in Non-Patent Document 2.

Figure 2:
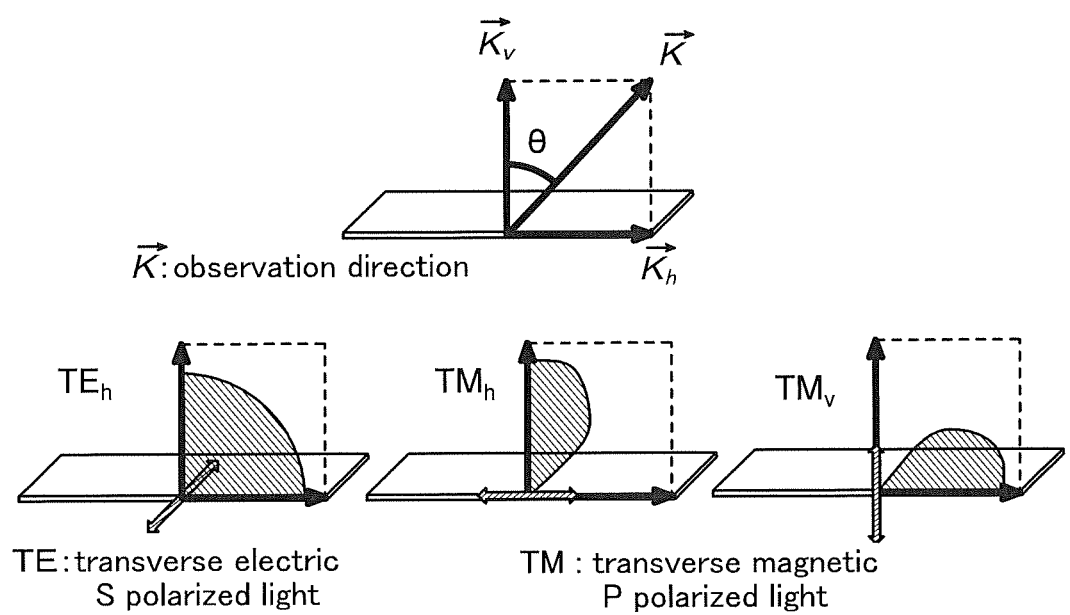
FIG. 2 shows a variation in emission intensity depending on the direction of a transition dipole moment and the observation angle.

Next, the orientation parameter α is described. FIG. 2 shows a relationship between the observation direction of a measurement device in measuring the spatial distribution of the emission intensity and vector components of a transition dipole moment over a substrate. Since a transition dipole moment is a vector, it can be synthesized and decomposed. An average transition dipole moment in the light-emitting material of the light-emitting layer can be decomposed into a component of the x-axis direction (TEh component), a component of the y-axis direction (TMh component), and a component of the z-axis direction (TMv component) which are orthogonal to one another.

Light is emitted from the molecule in the direction perpendicular to the transition dipole moment (a direction in a perpendicular plane) as described above. Among the components divided into the three directions, the TEh component and the TMh component (the x-axis direction and the y-axis direction) are transition dipole moments parallel to the substrate surface, and their emission directions are perpendicular to the substrate, so that light emission from the TEh component and the TMh component can be easily extracted. On the other hand, the TMv component (the z-axis direction) is a transition dipole moment perpendicular to the substrate surface and its emission direction is parallel to the substrate, so that light emission from the TMv component is not easily extracted.

In FIG. 2, a figure which extends from the center of an arrow that represents the vector of each component is a schematic figure which represents the emission intensity that is detected by the detector, when the direction of the detector is changed from front of the substrate (θ=0°) to parallel to the substrate (θ=90°). The vertical distance from the center is proportional to the intensity.

Since the detector is located in the direction in which light is emitted, the intensity of detected light of the TEh component (i.e., the vertical distance from the center of the arrow of the figure which extends from the center of the arrow in FIG. 2) is constant, even when the angle of the substrate is changed, and the figure which extends from the center of the arrow has a fan shape. On the other hand, the figures which extend from the centers of the arrows of the TMh component and the TMv component have distorted fan shapes, which indicates that the intensity of detected light is greatly changed depending on the angle θ of the detector to the substrate. As shown in FIG. 2, the TMh component has high intensity when θ is small (in a direction closer to the front direction of the substrate), whereas the TMv component has high intensity when θ is large (in a direction closer to the direction parallel to the substrate). In that case, the emission intensity measured by the measurement device (the emission intensity at a wavelength λ and at an angle θ: $I_\theta(\theta,\lambda)$) can be represented by Formula (1).

[Formula 1]

$$I_\lambda(\theta,\lambda)=\alpha \cdot I_{TMv}+(1-\alpha)\cdot(I_{TMh}+I_{TEh}) \qquad (1)$$

In the above formula, $I_{TMv}$, $I_{TMh}$, and $I_{TEh}$ represent spatial intensity distribution of light emitted from the transition dipoles arranged as shown in FIG. 2, and α represents the proportion of transition dipoles arranged perpendicular to the film surface (the TMv component). In addition, 1−α represents the proportion of transition dipoles arranged parallel to the film surface (the TMh and TEh components). That is, α can also be regarded as a parameter which represents the orientation of transition dipoles of light-emitting molecules.

In the above formula, when the transition dipoles are arranged only in the direction completely parallel to the substrate, the TMv component is eliminated and α is 0. In contrast, when the transition dipoles are arranged only in the direction perpendicular to the substrate, α is 1. When the directions of the transition dipoles are not the same, the directions of the transition dipoles are supposed to be isotropic, i.e., x-axis: y-axis: z-axis=1:1:1, so that the ratio of the component perpendicular to the substrate (the TMv component) to the components parallel to the substrate (the TMh and TEh components) is 1:2 and α is ⅓ (approximately 0.33).

As described above, $I_{TEh}$ is constant independent of the angle; however, $I_{TMh}$ and $I_{TMv}$ change depending on the angle (θ) of the substrate to the measurement device. Thus, by measuring the emission intensity while changing θ, α can be obtained from the change in $I_{TMh}$ and $I_{TMv}$ depending on θ.

In that case, $I_{TEh}$ which does not change depending on the angle hinders the measurement. The amplitude direction of an electric field of emitted light is the same as the direction of the transition dipole moment, and $I_{TEh}$ is an S-wave and $I_{TMv}$ and $I_{TMh}$ are P-waves. Thus, by disposing a linear polarizer in the direction perpendicular to the substrate surface, measurement can be performed under the condition where the TEh component is excluded.

The TMh component and the TMv component are compared. The emission direction of the TMh component is mainly perpendicular to the substrate and the emission direction of the TMv component is mainly parallel to the substrate; in a light-emitting element in which light emission is obtained from a solid, a large part of light emission from the TMv component is totally reflected and cannot be extracted to the outside. On the other hand, light emission from the TMh component is more easily extracted to the outside than light emission from the TMv component. Furthermore, in a light-emitting element in which the thickness is optically optimized, light emission from the TMh component whose emission direction is mainly perpendicular to the substrate is intensified through interference, so that the emission intensity of the TMh component is increased (thus, the emission efficiency is maximized). That is, unless the orientation parameter α is very close to 1, a difference between the emission intensity of the TMv component and that of the TMh component is very large in the light-emitting element in which the thickness is optically optimized. That is, in the light-emitting element in which the emission efficiency is maximized, most light emission which is observed depends on the TMh component. In the case where the difference between the emission intensity of the TMh component and that of the TMv component is large as described above, it is difficult to experimentally extract light emission from the component which has lower intensity (namely the TMv component) from the distribution of the emission intensity depending on the angle.

Thus, in this embodiment, the emission intensity in the front direction of the substrate is suppressed as much as possible by utilizing an interference effect (that is, light emission from the TMh component is reduced as much as possible by utilizing an interference effect), so that the parameter α can be easily obtained. For this purpose, an element in which the thickness is adjusted is prepared for measurement. Specifically, an element is fabricated and used for measurement, in which the luminance in the front direction is lowered by setting the distance between a light-emitting region and a cathode to nλ/2. In general, the thickness is adjusted in such a manner that the thickness of an electron-transport layer to which an alkali metal is added is increased. However, since there is a limitation on the conductivity of the film, the drive voltage might be increased or the carrier balance might be poor. Accordingly, in order to adjust the thickness, it is preferable to use a composite material of a material having a hole-transport property and a material having an acceptor property with respect to the material having a hole-transport property. It is preferable to use the composite material for a hole-injection layer in an EL layer or a layer between an electron-injection layer and a cathode.

As the material having a hole-transport property used for the composite material, any of a variety of organic compounds such as aromatic amine compounds, carbazole derivatives, aromatic hydrocarbons, and high molecular compounds (e.g., oligomers, dendrimers, or polymers) can be used. Note that the substance with a hole-transport property which is used for the composite material is preferably a substance having a hole mobility of $10^{-6}$ cm$^2$/Vs or more. Examples of organic compounds that can be used as the material having a hole-transport property in the composite material are specifically given below.

Examples of the material having a hole-transport property that can be used for the composite material include aromatic amine compounds such as N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B); carbazole derivatives such as 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl]-2,3,5,6-tetraphenylbenzene; and aromatic hydrocarbons such as 2-tent-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Other examples are pentacene, coronene, and the like. Examples of the aromatic hydrocarbon having a vinyl skeleton are 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

In particular, as the material having a hole-transport property, a dibenzothiophene derivative or a dibenzofuran derivative such as 4-[4-(9-phenyl-9H-fluoren-9-yl)phenyl]-6-phenyldibenzothiophene (abbreviation: DBTFLP-IV), 1,3,5-tri(dibenzothiophen-4-yl)-benzene (abbreviation: DBT3P-II), 4,4'-(biphenyl-2,2'-diyl)-bis-dibenzothiophene (abbreviation: oDBTBP-II), 2,8-diphenyl-4-[4-(9-phenyl-9H-fluoren-9-yl)phenyl]dibenzothiophene (abbreviation: DBTFLP-III), 4-[3-(triphenylen-2-yl)phenyl]dibenzothiophene (abbreviation: mDBTPTp-II), 3,6-di-(dibenzothiophen-4-yl)-9-phenyl-9H-carbazole (abbreviation: DBT2PC-II), 4-[3-(9,10-diphenyl-2-anthryl)phenyl]dibenzothiophene (abbreviation: 2mDBTPPA-II), 4-[3-(9,10-diphenyl-2-anthryl)phenyl]dibenzofuran (abbreviation: 2mDBFPPA-II), or 4-[4-(9-phenylanthracen-10-yl)phenyl]dibenzothiophene (abbreviation: mDBTPA-II), or a hydrocarbon compound in which a substituent is bonded to a naphthalene skeleton, a phenanthrene skeleton, or a triphenylene skeleton and in which the molecular weight is 350 to 2000, such as 1-[3,5-di(naphthalen-1-yl)phenyl]naphthalene (abbreviation: N3P), 9-[3,5-di(phenanthren-9-yl)phenyl]phenanthrene (abbreviation: Pn3P), 1,2,3,4-tetraphenylnaphthalene (abbreviation: P4N), 2-[3,5-di-(naphthalen-2-yl)-phenyl]-naphthalene (abbreviation: bN3P), or 9,9'-(biphenyl-3,3'-diyl)-di-phenanthrene (abbreviation: mPnBP) can be used. A composite material including such a material exhibits no absorption ranging from a visible light region to a near-infrared region. The measurement results of a light-emitting element containing the composite material almost correspond to the calculation results, that is, α can be accurately obtained.

Other examples are high molecular compounds such as poly(N-vinylcarbazole) (abbreviation: PVK), poly(-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: poly-TPD).

As examples of the substance having an acceptor property, 7,7,8,8-tetracyano-2,3,5,6-tetrafluoroquinodimethane (abbreviation: $F_4$-TCNQ), chloranil, and the like can be given. In addition, a transition metal oxide can be given. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable since their electron-accepting property is high. Among these, molybdenum oxide is especially preferable because it is stable in the air, has a low hygroscopic property, and is easy to handle.

The composite material has high conductivity and thus has an advantage in that the drive voltage is unlikely to be increased and the carrier balance can be kept even when the thickness of a film containing the composite material is large.

As described above, a light-emitting element with a partly special structure is used for the measurement. However, by forming a light-emitting layer having a structure similar to that of a general light-emitting element, the evaluation results of the orientation state can also be applied to the orientation state of a light-emitting element with an ordinary structure.

Such a light-emitting element is made to emit light and a linear polarizer is disposed in the direction perpendicular to the substrate; in this manner, the angle dependence of the emission intensity is measured. The emission intensity may be represented as an intensity at a certain wavelength but is preferably represented as a value obtained by integrating the emission spectrum intensity in one embodiment of the present invention, because a more accurate examination can be performed.

This experimental value is compared with a calculation result obtained by an organic device simulator (a semiconducting emissive thin film optics simulator, namely setfos, produced by Cybernet Systems Co., Ltd.), so that a of the light-emitting element can be obtained. In this calculation, the spectrum shape of a light-emitting material, the thickness of a stacked structure, the refractive index, the extinction efficiency, and the position and the width of a light-emitting region are input to calculate the emission intensity (spectrum) depending on the angle θ, which corresponds to an input given parameter α.

Note that the position of the light-emitting region cannot be measured and is thus assumed. The position of the light-emitting region can be assumed empirically in consideration of a carrier-transport property or the like of the light-emitting layer. However, the following method is preferable to a method of fixing the position of the light-emitting region to one position in the thickness direction: first, a light-emitting position where the recombination probability is supposed to be the highest (e.g., the vicinity of the interface between a hole-transport layer and the light-emitting layer when, for example, an electron-transport property of the light-emitting layer is higher than a hole-transport property thereof) is fixed, and calculation is performed assuming that the light-emitting region spreads such that the recombination probability is decreased exponentially from the light-emitting position. Through this method, favorable calculation results of the spectrum shape close to the measured one can be obtained.

The light extraction efficiency in each orientation state is discussed. As compared with the case where the transition dipoles have a random orientation ($\alpha=\frac{1}{3}\approx 0.33$), transition dipoles of ⅓ of molecules which have been perpendicular to the substrate in a random orientation are parallel to the substrate in the case where the transition dipoles have an orientation completely parallel to the substrate ($\alpha=0$). Therefore, the proportion of the transition dipoles parallel to the substrate surface is 1.5 times the proportion in the random orientation.

As described above, most light emission observed in the optimized light-emitting element is derived from emission components of molecules in the horizontal orientation, and light emission from molecules in the perpendicular orientation (i.e., the TMv component) is relatively weak so as to be negligible. In other words, it is suggested that, in the case of the random orientation, light emission from ⅓ of molecules is not extracted substantially. On the other hand, in the case of $\alpha=0$, the proportion of transition dipoles parallel to the substrate is 1.5 times the proportion in the random orientation as described above, so that the proportion of molecules contributing to observed light emission and the light extraction efficiency are also approximately 1.5 times those in the random orientation.

When a light-emitting material (iridium complex) that has a small value of a calculated by the above method is used in the above manner, the amount of light which can be extracted to the outside can be increased as compared to that in the case of random orientation, which facilitates fabrication of a light-emitting element with favorable light extraction efficiency.

The values of the planarity of the above-described tris iridium complexes, the values of external quantum efficiency of the light-emitting elements formed using the iridium complexes, and the orientation parameter α are listed in the following table.

TABLE 3

| | A [Å] | B [Å] | C [Å] | A × B/C$^2$ [−] | External quantum efficiency (%) | Orientation parameter a |
|---|---|---|---|---|---|---|
| Ir(mpptz-diBuCNp)$_3$ (104) | 18.9 | 18.0 | 10.5 | 3.1 | 35.6 | 0.15 |
| Ir(mpptz-tmp)$_3$ (105) | 17.9 | 17.0 | 10.4 | 2.8 | 29.3 | 0.22 |
| Ir(mpptz-diPrp)$_3$ (106) | 16.3 | 15.5 | 10.4 | 2.4 | 27.7 | 0.27 |

As shown in the table, there is also a relationship between the planarity and the orientation, which indicates that the tris iridium complex with high planarity has high orientation; as a result, improved external quantum efficiency is obtained. When the light-emitting element includes the light-emitting layer in which the orientation parameter α of the iridium complex is lower than or equal to 0.25, the light-emitting element achieves extremely high emission efficiency easily.

<<Light-Emitting Element>>

Next, an example of a light-emitting element of one embodiment of the present invention is described in detail below with reference to FIG. 3A.

In this embodiment, the light-emitting element includes a pair of electrodes (the first electrode 101 and the second electrode 102), and the EL layer 103 provided between the first electrode 101 and the second electrode 102. Note that the first electrode 101 functions as an anode and the second electrode 102 functions as a cathode.

To function as an anode, the first electrode 101 is preferably formed using any of metals, alloys, conductive compounds having a high work function (specifically, a work function of 4.0 eV or more), mixtures thereof, and the like. Specific examples are indium oxide-tin oxide (ITO: indium tin oxide), indium oxide-tin oxide containing silicon or silicon oxide, indium oxide-zinc oxide, indium oxide containing tungsten oxide and zinc oxide (IWZO), and the like. Films of these electrically conductive metal oxides are usually formed by a sputtering method but may be formed by application of a sol-gel method or the like. For example, indium oxide-zinc oxide is deposited by a sputtering method using a target obtained by adding 1 wt % to 20 wt % of zinc oxide to indium oxide. A film of indium oxide containing tungsten oxide and zinc oxide (IWZO) can be formed by a sputtering method using a target in which tungsten oxide and zinc oxide are added to indium oxide at 0.5 wt % to 5 wt % and 0.1 wt % to 1 wt %, respectively. Other examples are gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride), and the like. Graphene can also be used. Note that when a composite material described later is used for a layer which is in contact with the first electrode 101 in the EL layer 103, an electrode material can be selected regardless of its work function.

The stacked-layer structure of the EL layer 103 can be formed by combining a hole-injection layer, a hole-transport layer, a light-emitting layer, an electron-transport layer, an electron-injection layer, a carrier-blocking layer, an intermediate layer, and the like as appropriate. In this embodiment, the EL layer 103 has a structure in which a hole-injection layer 111, a hole-transport layer 112, a light-emitting layer 113, an electron-transport layer 114, and an electron-injection layer 115 are stacked in this order over the first electrode 101. Specific examples of the materials forming the layers are given below.

The hole-injection layer 111 is a layer containing a substance having a high hole-injection property. The hole-injection layer 111 can be formed using molybdenum oxide, vanadium oxide, ruthenium oxide, tungsten oxide, manganese oxide, or the like. Alternatively, the hole-injection layer 111 can be formed using a phthalocyanine-based compound such as phthalocyanine (abbreviation: $H_2Pc$) or copper phthalocyanine (abbreviation: CuPc), an aromatic amine compound such as 4,4'-bis[N-(4-diphenylaminophenyl)-N-phenylamino]biphenyl (abbreviation: DPAB) or N,N'-bis{4-[bis(3-methylphenyl)amino]phenyl}-N,N'-diphenyl-(1,1'-biphenyl)-4,4'-diamine (abbreviation: DNTPD), a high molecule such as poly(3,4-ethylenedioxythiophene)/poly(styrenesulfonic acid) (PEDOT/PSS), 7,7,8,8-tetracyano-2,3,5,6-tetrafluoroquinodimethane (abbreviation: $F_4$-TCNQ), chloranil, or the like.

Alternatively, a composite material in which a substance having a hole-transport property contains a substance having an acceptor property can be used for the hole-injection layer 111. Note that the use of the composite material in which a substance having a hole-transport property contains a substance having an acceptor property enables selection of a material used to faun an electrode regardless of its work function. In other words, besides a material having a high work function, a material having a low work function can be used for the first electrode 101. As examples of the substance having an acceptor property, 7,7,8,8-tetracyano-2,3,5,6-tetrafluoroquinodimethane (abbreviation: $F_4$-TCNQ), chloranil, and the like can be given. In addition, a transition metal oxide can be given. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable since their electron-accepting property is high. Among these, molybdenum oxide is especially preferable because it is stable in the air, has a low hygroscopic property, and is easy to handle.

As the substance having a hole-transport property which is used for the composite material, any of a variety of organic compounds such as aromatic amine compounds, carbazole derivatives, aromatic hydrocarbons, and high molecular compounds (e.g., oligomers, dendrimers, or polymers) can be used. Note that the substance with a hole-transport property which is used for the composite material is preferably a substance having a hole mobility of $10^{-6}$ $cm^2/Vs$ or more. Organic compounds that can be used as the substance having a hole-transport property in the composite material are specifically given below.

Examples of the substance having a hole-transport property that can be used for the composite material include aromatic amine compounds such as N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B); carbazole derivatives such as 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl]-2,3,5,6-tetraphenylbenzene; and aromatic hydrocarbons such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Other examples are pentacene, coronene, and the like. Examples of the aromatic hydrocarbon having a vinyl skeleton are 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

Other examples are high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: poly-TPD).

By providing the hole-injection layer 111, a high hole-injection property can be achieved to allow a light-emitting element to be driven at a low voltage.

The hole-transport layer 112 is a layer containing a substance having a hole-transport property. Examples of the substance having a hole-transport property are aromatic amine compounds such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), and 4-phenyl-4'-(9-phenylfluoren-9-yl)triphenylamine (abbreviation: BPAFLP). The substances listed here have high hole-transport properties and are mainly ones that have a hole mobility of $10^{-6}$ cm$^2$/Vs or higher. An organic compound given as an example of the substance having a hole-transport property in the composite material described above can also be used for the hole-transport layer 112. Note that the layer that contains a substance having a hole-transport property is not limited to a single layer, and may be a stack of two or more layers including any of the above substances.

It is preferable that the light-emitting layer 113 include the tris iridium complex whose parameter of planarity (A×B/C$^2$) calculated in the above manner is high, specifically, greater than or equal to 2.5. For example, tris{2-[5-(2-methylphenyl)-4-(3,3',5,5'-tetramethyl-1,1'-biphenyl-4-yl)-4H-1,2,4-triazol-3-yl-κN$^2$]phenyl-κC}iridium(III) (abbreviation: [Ir(mpptz-tetmb)$_3$]; Structural formula (100)); tris[2-(6-methyl-5-phenyl-4-pyrimidinyl-κN$^3$)phenyl-κC]iridium (III) (abbreviation: [Ir(mpppm)$_3$]; Structural formula (101)); tris{2-[1-(4-cyano-2,6-diisobutylphenyl)-1H-imidazol-2-yl-κN$^3$]phenyl-κC}iridium(III) (abbreviation: [Ir(pim-diBuCNp)$_3$]; Structural formula (102)); tris{4'-cyano-2',6'-dimethyl-3-[3-methyl-1-(2,4,6-trimethylphenyl)-1H-1,2,4-triazol-5-yl-κN$^4$]-1,1'-biphenyl-4-yl-κC}iridium(III) (abbreviation: [Ir(MdmCN5btz1-tmp)$_3$]; Structural formula (103)); tris{2-[4-(4-cyano-2,6-diisobutylphenyl)-5-(2-methylphenyl)-4H-1,2,4-triazol-3-yl-κN$^2$]phenyl-κC}iridium (III) (abbreviation: [Ir(mpptz-diBuCNp)$_3$]; Structural formula (104)); tris{2-[5-(2-methylphenyl)-4-(2,4,6-trimethylphenyl)-4H-1,2,4-triazol-3-yl-κN$^2$]phenyl-κC}iridium(III) (abbreviation: [Ir(mpptz-tmp)$_3$]); Structural formula (105)); and the like are particularly preferable. Since the light-emitting layer with the iridium complex can emit phosphorescence with high efficiency, the light-emitting element can achieve high external quantum efficiency.

Note that a layer which includes a fluorescent substance and emits fluorescence, a layer which includes a phosphorescent substance and emits phosphorescence, and a layer which includes a thermally activated delayed fluorescent (TADF) substance and emits TADF can be included as light-emitting layers in the light-emitting element. Note that the light-emitting layer may be formed of a single layer or a plurality of layers. In the case where the light-emitting layer formed of a plurality of layers is formed, a layer containing a phosphorescent substance and a layer containing a fluorescent substance may be stacked. In that case, an exciplex described later is preferably utilized for the layer containing the phosphorescent substance.

As the fluorescent substance, any of the following substances can be used, for example. Fluorescent substances other than those given below can also be used. Examples of the fluorescent substance are 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N'N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and the like. Condensed aromatic diamine compounds typified by pyrenediamine compounds such as 1,6FLPAPrn and 1,6mMemFLPAPrn are particularly preferable because of their high hole-trapping properties, high emission efficiency, and high reliability.

Examples of a material which can be used as a phosphorescent substance in the light-emitting layer 113 are as follows: organometallic iridium complexes having a 4H-triazole skeleton, such as tris{2-[5(2-methylphenyl)-4-(2,6-dimethylphenyl)-4H-1,2,4-triazol-3-yl-κN$^2$]phenyl-κC}iridium(III) (abbreviation: [Ir(mpptz-dmp)$_3$]), tris(5-methyl-3,4-diphenyl-4H-1,2,4-triazolato)iridium(III) (abbreviation: Ir(Mptz)$_3$), and tris[4-(3-biphenyl)-5-isopropyl-3-phenyl-4H-1,2,4-triazolato]iridium(III) (abbreviation: [Ir(iPrptz-3b)$_3$]); organometallic iridium complexes having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: Ir(Prptz1-Me)$_3$); organometallic iridium complexes having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and organometallic iridium complexes in which a phenylpyridine derivative having an electron-withdrawing group is a ligand, such as bis[2-(4',6'-difluorophenyl)pyridinato-N,C²']iridium(III) tetrakis(1-pyrazolyl)borate (abbreviation: FIr6), bis[2-(4',6'-difluorophenyl)pyridinato-N,C²']iridium(III) picolinate (abbreviation: FIrpic), bis{2-[3',5'-bis(trifluoromethyl)phenyl]pyridinato-N,C²'}iridium(III) picolinate (abbreviation: [Ir(CF₃ppy)₂(pic)]), and bis[2-(4',6'-difluorophenyl)pyridinato-N,C²']iridium(III) acetylacetonate (abbreviation: FIr(acac)). These are compounds emitting blue phosphorescence and have an emission peak at 440 nm to 520 nm.

For example, organometallic iridium complexes having a pyrimidine skeleton, such as tris(4-methyl-6-phenylpyrimidinato)iridium(III) (abbreviation: [Ir(mppm)₃]), tris(4-t-butyl-6-phenylpyrimidinato)iridium(III) (abbreviation: [Ir(t-Buppm)₃]), (acetylacetonato)bis(6-methyl-4-phenylpyrimidinato)iridium(III) (abbreviation: [Ir(mppm)₂(acac)]), (acetylacetonato)bis(6-tert-butyl-4-phenylpyrimidinato)iridium(III) (abbreviation: [Ir(tBuppm)₂(acac)]), (acetylacetonato)bis[6-(2-norbornyl)-4-phenylpyrimidinato]iridium(III) (abbreviation: [Ir(nbppm)₂(acac)]), (acetylacetonato)bis[5-methyl-6-(2-methylphenyl)-4-phenylpyrimidinato]iridium(III) (abbreviation: [Ir(mpmppm)₂(acac)]), and (acetylacetonato)bis(4,6-diphenylpyrimidinato)iridium(III) (abbreviation: [Ir(dppm)₂(acac)]); organometallic iridium complexes having a pyrazine skeleton, such as (acetylacetonato)bis(3,5-dimethyl-2-phenylpyrazinato)iridium(III) (abbreviation: [Ir(mppr-Me)₂(acac)]) and (acetylacetonato)bis(5-isopropyl-3-methyl-2-phenylpyrazinato)iridium(III) (abbreviation: [Ir(mppr-iPr)₂(acac)]); organometallic iridium complexes having a pyridine skeleton, such as tris(2-phenylpyridinato-N,C²')iridium(III) (abbreviation: [Ir(ppy)₃]), bis(2-phenylpyridinato-N,C²')iridium(III) acetylacetonate (abbreviation: [Ir(ppy)₂(acac)]), bis(benzo[h]quinolinato)iridium(III) acetylacetonate (abbreviation: [Ir(bzq)₂(acac)]), tris(benzo[h]quinolinato)iridium(III) (abbreviation: [Ir(bzq)₃]), tris(2-phenylquinolinato-N,C²')iridium(III) (abbreviation: [Ir(pq)₃]), and bis(2-phenylquinolinato-N,C²')iridium(III) acetylacetonate (abbreviation: [Ir(pq)₂(acac)]); and a rare earth metal complex such as tris(acetylacetonato) (monophenanthroline)terbium(III) (abbreviation: [Tb(acac)₃(Phen)]) can be given. These are mainly compounds emitting green phosphorescence and have an emission peak at 500 nm to 600 nm. Note that an organometallic iridium complex having a pyrimidine skeleton has distinctively high reliability and emission efficiency and is thus especially preferable.

For example, organometallic iridium complexes having a pyrimidine skeleton, such as (diisobutyrylmethanato)bis[4,6-bis(3-methylphenyl)pyrimidinato]iridium(III) (abbreviation: [Ir(5mdppm)₂(dibm)]), bis[4,6-bis(3-methylphenyl)pyrimidinato] (dipivaloylmethanato)iridium(III) (abbreviation: [Ir(5mdppm)₂(dpm)]), and bis[4,6-di(naphthalen-1-yl)pyrimidinato] (dipivaloylmethanato)iridium(III) (abbreviation: [Ir(d1npm)₂(dpm)]); organometallic iridium complexes having a pyrazine skeleton, such as (acetylacetonato)bis(2,3,5-triphenylpyrazinato)iridium(III) (abbreviation: [Ir(tppr)₂(acac)]), bis(2,3,5-triphenylpyrazinato) (dipivaloylmethanato)iridium(III) (abbreviation: [Ir(tppr)₂(dpm)]), and (acetylacetonato)bis[2,3-bis(4-fluorophenyl)quinoxalinato]iridium(III) (abbreviation: [Ir(Fdpq)₂(acac)]); organometallic iridium complexes having a pyridine skeleton, such as tris(1-phenylisoquinolinato-N,C²')iridium(III) (abbreviation: [Ir(piq)₃]) and bis(1-phenylisoquinolinato-N,C²')iridium(III) acetylacetonate (abbreviation: [Ir(piq)₂(acac)]); platinum complexes such as 2,3,7,8,12,13,17,18-octaethyl-21H,23H-porphyrinplatinum(II) (abbreviation: [PtOEP]); and rare earth metal complexes such as tris(1,3-diphenyl-1,3-propanedionato) (monophenanthroline)europium(III) (abbreviation: [Eu(DBM)₃(Phen)]) and tris[1-(2-thenoyl)-3,3,3-trifluoroacetonato] (monophenanthroline)europium(III) (abbreviation: [Eu(TTA)₃(Phen)]) can be given. These are compounds emitting red phosphorescence and have an emission peak at 600 nm to 700 nm. Further, the organometallic iridium complexes having a pyrazine skeleton can provide red light emission with favorable chromaticity.

Phosphorescent materials other than those given above may be used.

Examples of the TADF material include a fullerene, a derivative thereof, an acridine, derivative thereof, and an eosin derivative. Furthermore, a metal-containing porphyrin, such as a porphyrin containing magnesium (Mg), zinc (Zn), cadmium (Cd), tin (Sn), platinum (Pt), indium (In), or palladium (Pd) can be used. Examples of the metal-containing porphyrin are a protoporphyrin-tin fluoride complex (SnF₂(Proto IX)), a mesoporphyrin-tin fluoride complex (SnF₂(Meso IX)), a hematoporphyrin-tin fluoride complex (SnF₂(Hemato IX)), a coproporphyrin tetramethyl ester-tin fluoride complex (SnF₂(Copro III-4Me)), an octaethylporphyrin-tin fluoride complex (SnF₂(OEP)), an etioporphyrin-tin fluoride complex (SnF₂(Etio I)), and an octaethylporphyrin-platinum chloride complex (PtCl₂OEP), which are represented by structural formulae shown below.

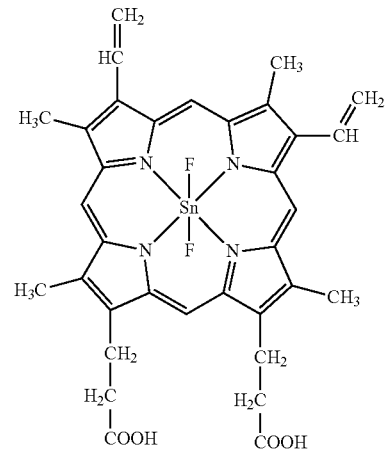

SnF₂(Proto IX)

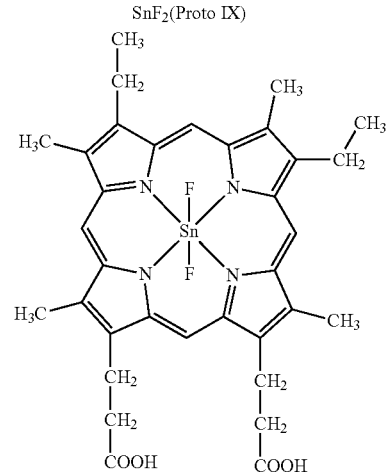

SnF₂(Meso IX)

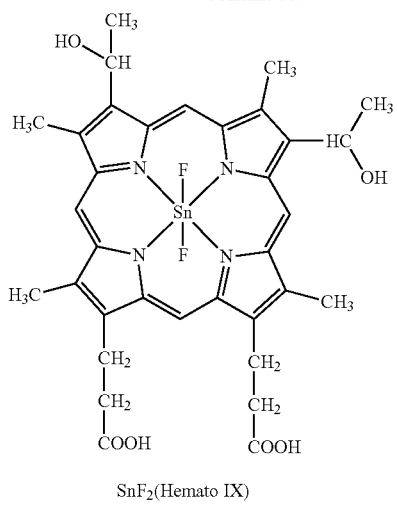

SnF₂(Hemato IX)

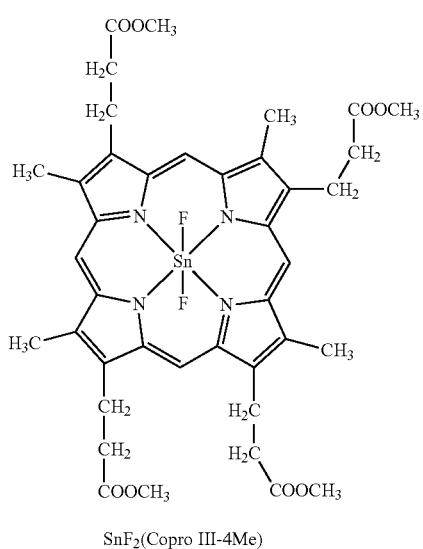

SnF₂(Copro III-4Me)

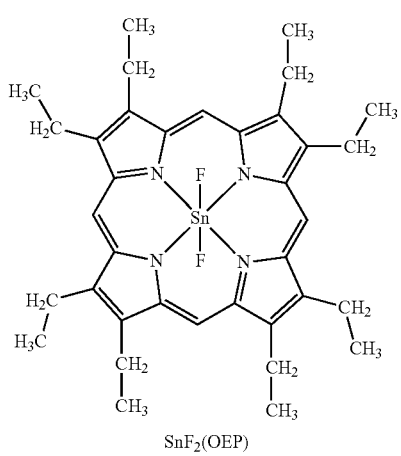

SnF₂(OEP)

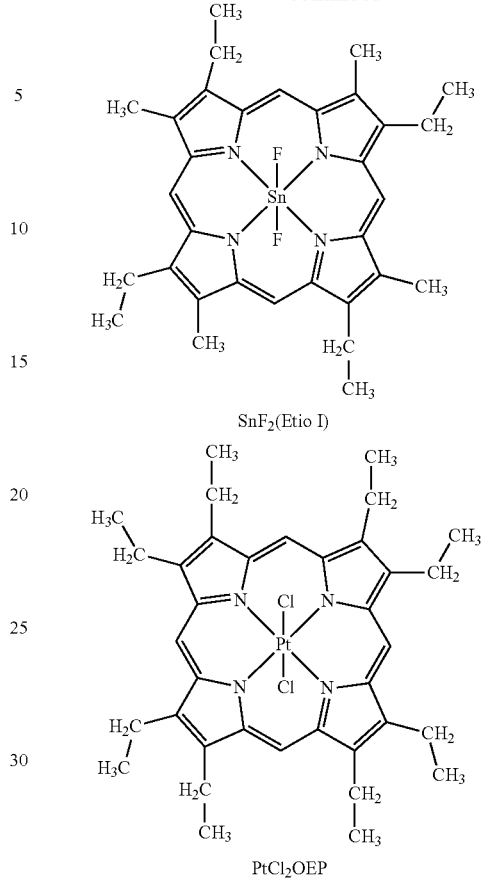

SnF₂(Etio I)

PtCl₂OEP

Alternatively, a heterocyclic compound having both of a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazine-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) shown in the following structural formulae, can be used. The heterocyclic compound is preferable because of having the π-electron rich heteroaromatic ring and the π-electron deficient heteroaromatic ring, for which the electron-transport property and the hole-transport property are high. Note that a substance in which the π-electron rich heteroaromatic ring is directly bonded to the π-electron deficient heteroaromatic ring is particularly preferably used because the donor property of the π-electron rich heteroaromatic ring and the acceptor property of the π-electron deficient heteroaromatic ring are both increased, the energy difference between the S₁ level and the T₁ level becomes small, and thus thermally activated delayed fluorescence can be obtained with high efficiency. Note that an aromatic ring to which an electron-withdrawing group such as a cyano group is bonded may be used instead of the π-electron deficient heteroaromatic ring.
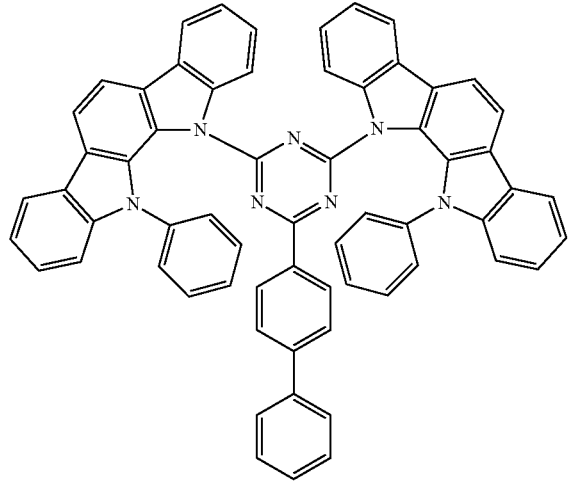
PIC-TRZ
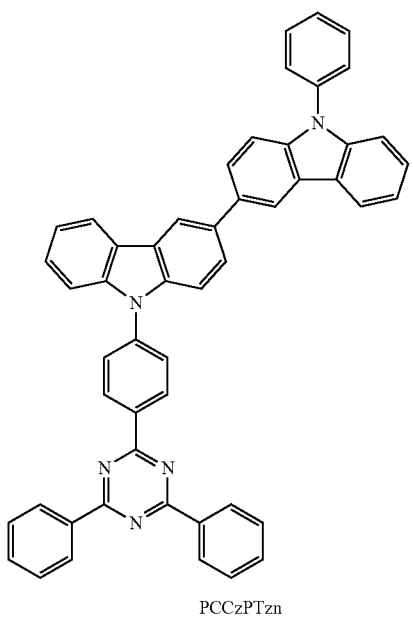
PCCzPTzn
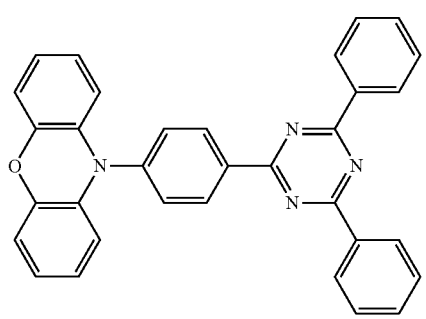
PXZ-TRZ
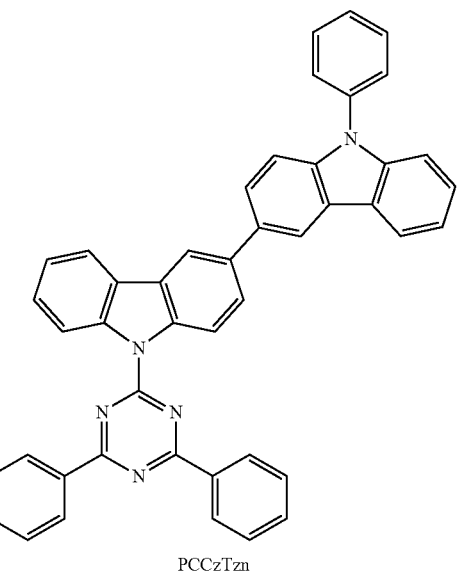
PCCzTzn
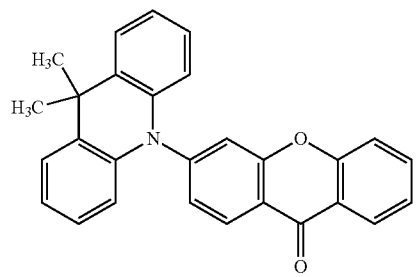
ACRXTN
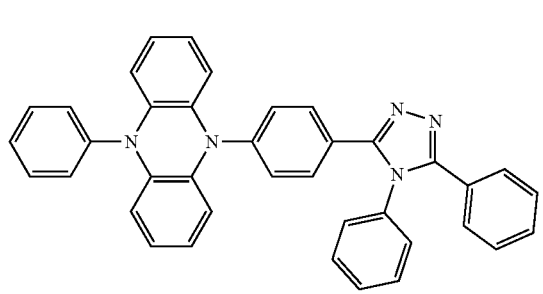
PPZ-3TPT
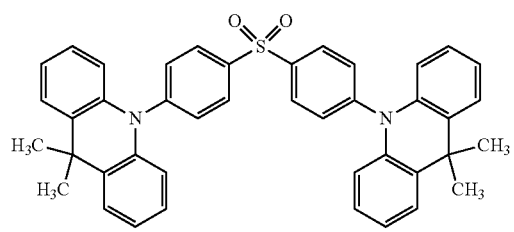
DMAC-DPS -continued

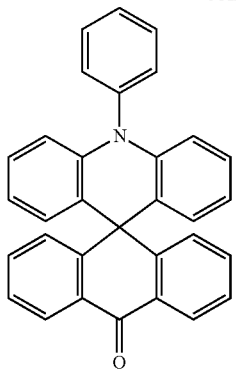

ACRSA

In the case of using a fluorescent substance, materials that can be suitably used as the host material in the light-emitting layer are materials having an anthracene skeleton such as 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), and 9-phenyl-10-{4-(9-phenyl-9H-fluoren-9-yl)biphenyl-4'-yl}anthracene (abbreviation: FLPPA). The use of a substance having an anthracene skeleton as the host material for the fluorescent substance makes it possible to obtain a light-emitting layer with high emission efficiency and high durability. In particular, CzPA, cgDBCzPA, 2mBnfPPA, and PCzPA are preferable because of their excellent characteristics.

In the case where a material other than the above-mentioned materials is used as a host material, various carrier-transport materials, such as a material having an electron-transport property or a material having a hole-transport property, can be used.

Examples of the material with an electron-transport property are a metal complex such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ); a heterocyclic compound having a polyazole skeleton such as 2-(4-biphenylyl)-5-(4-tent-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), or 2-[3-(dibenzothiophen-4-yl)phenyl]-1-phenyl-1H-benzimidazole (abbreviation: mDBTBIm-II); a heterocyclic compound having a diazine skeleton such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), or 4,6-bis[3-(4-dibenzothienyl)phenyl]pyrimidine (abbreviation: 4,6mDBTP2Pm-II); and a heterocyclic compound having a pyridine skeleton such as 3,5-bis[3-(9H-carbazol-9-yl)phenyl]pyridine (abbreviation: 35DCzPPy) or 1,3,5-tri[3-(3-pyridyl)phenyl]benzene (abbreviation: TmPyPB). Among the above materials, a heterocyclic compound having a diazine skeleton and a heterocyclic compound having a pyridine skeleton have high reliability and are thus preferable. Specifically, a heterocyclic compound having a diazine (pyrimidine or pyrazine) skeleton has a high electron-transport property to contribute to a reduction in drive voltage.

Examples of materials with a hole-transport property are a compound having an aromatic amine skeleton such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), or N-phenyl-N-[4-(9-phenyl-9H-carbazol-3-yl)phenyl]spiro-9,9'-bifluoren-2-amine (abbreviation: PCBASF); a compound having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP); a compound having a thiophene skeleton such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), or 4-[4-(9-phenyl-9H-fluoren-9-yl)phenyl]-6-phenyldibenzothiophene (abbreviation: DBTFLP-IV); and a compound having a furan skeleton such as 4,4',4''-(benzene-1,3,5-triyl)tri(dibenzofuran) (abbreviation: DBF3P-II) or 4-{3-[3-(9-phenyl-9H-fluoren-9-yl)phenyl]phenyl}dibenzofuran (abbreviation: mmDBFFLBi-II). Among the above materials, a compound having an aromatic amine skeleton and a compound having a carbazole skeleton are preferable because these compounds are highly reliable and have high hole-transport properties to contribute to a reduction in drive voltage. Hole-transport materials can be selected from a variety of substances as well as from the hole-transport materials given above.

In the case of using a fluorescent substance as a light-emitting substance, materials having an anthracene skeleton such as 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), and 9-phenyl-10-{4-(9-phenyl-9H-fluoren-9-yl)-biphenyl-4'-yl}-anthracene (abbreviation: FLPPA) are preferably used. The use of a substance having an anthracene skeleton as the host material for the fluorescent substance makes it possible to obtain a light-emitting layer with high emission efficiency and high durability. In particular, CzPA, cgDBCzPA, 2mBnfPPA, and PCzPA are preferable because of their excellent characteristics.

Note that the host material may be a mixture of a plurality of kinds of substances, and in the case of using a mixed host material, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The ratio of the content of the material having a hole-transport property to the content of the material having an electron-transport property may be 1:9 to 9:1.

These mixed host materials may form an exciplex. When a combination of these materials is selected so as to form an exciplex that exhibits light emission whose wavelength overlaps the wavelength of a lowest-energy-side absorption band of the fluorescent substance, the phosphorescent substance, or the TADF material, energy is transferred smoothly and light emission can be obtained efficiently. Such a structure is preferable in that drive voltage can be reduced.

The light-emitting layer 113 having the above-described structure can be formed by co-evaporation by a vacuum evaporation method, or a gravure printing method, an offset printing method, an inkjet method, a spin coating method, a dip coating method, or the like using a mixed solution.

The electron-transport layer 114 contains a substance with an electron-transport property. As the substance with an electron-transport property, the materials having an electron-transport property or having an anthracene skeleton, which are described above as materials for the host material, can be used.

A layer for controlling transport of electron carriers may be provided between the electron-transport layer and the light-emitting layer. This is a layer formed by addition of a small amount of a substance having a high electron-trapping property to a material having a high electron-transport property as described above, and the layer is capable of adjusting carrier balance by suppressing transport of electron carriers. Such a structure is very effective in preventing a problem caused when electrons pass through the light-emitting layer, such as a reduction in element lifetime.

In addition, an electron-injection layer 115 may be provided in contact with the second electrode 102, between the electron-transport layer 114 and the second electrode 102. For the electron-injection layer 115, an alkali metal, an alkaline earth metal, or a compound thereof, such as lithium fluoride (LiF), cesium fluoride (CsF), or calcium fluoride ($CaF_2$), can be used. For example, a layer that is formed using a substance having an electron-transport property and contains an alkali metal, an alkaline earth metal, or a compound thereof can be used. An electride may also be used for the electron-injection layer 115. Examples of the electride include a substance in which electrons are added at high concentration to calcium oxide-aluminum oxide. Note that a layer which is formed using a substance having an electron-transport property and contains an alkali metal or an alkaline earth metal is preferably used for the electron-injection layer 115, in which case electrons are efficiently injected from the second electrode 102.

Figure 3B:
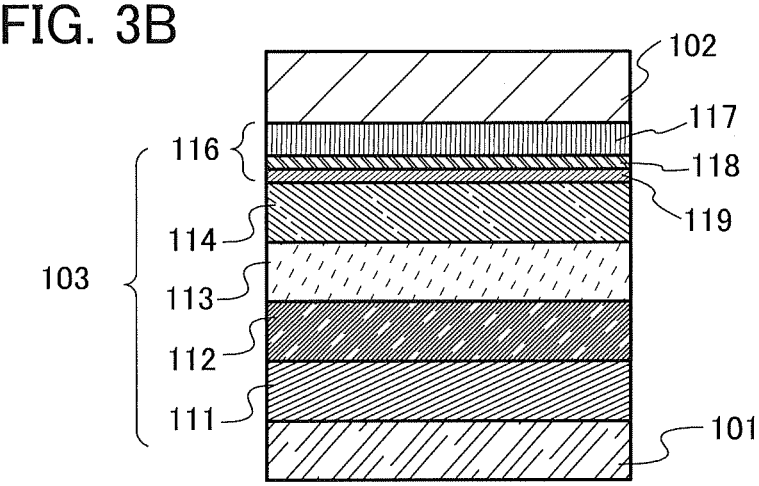

Instead of the electron-injection layer 115, a charge-generation layer 116 may be provided (FIG. 3B). The charge-generation layer 116 refers to a layer capable of injecting holes into a layer in contact with the cathode side of the charge-generation layer 116 and electrons into a layer in contact with the anode side thereof when a potential is applied. The charge-generation layer 116 includes at least a p-type layer 117. The p-type layer 117 is preferably formed using any of the composite materials given above as examples of materials that can be used for the hole-injection layer 111. The p-type layer 117 may be formed by stacking a film containing the above-described acceptor material as a material included in the composite material and a film containing the above-described hole-transport material. When a potential is applied to the p-type layer 117, electrons are injected into the electron-transport layer 114 and holes are injected into the second electrode 102 serving as a cathode; thus, the light-emitting element operates. When a layer containing organic compounds of one embodiment of the present invention exists in the electron-transport layer 114 so as to be in contact with the charge-generation layer 116, a luminance decrease due to accumulation of driving time of the light-emitting element can be suppressed, and thus, the light-emitting element can have a long lifetime.

Note that the charge-generation layer 116 preferably includes either an electron-relay layer 118 or an electron-injection buffer layer 119 or both in addition to the p-type layer 117.

The electron-relay layer 118 contains at least the substance having an electron-transport property and has a function of preventing an interaction between the electron-injection buffer layer 119 and the p-type layer 117 and smoothly transferring electrons. The LUMO level of the substance with an electron-transport property contained in the electron-relay layer 118 is preferably between the LUMO level of an acceptor substance in the p-type layer 117 and the LUMO level of a substance contained in a layer of the electron-transport layer 114 in contact with the charge-generation layer 116. As a specific value of the energy level, the LUMO level of the substance having an electron-transport property in the electron-relay layer 118 is preferably higher than or equal to −5.0 eV, more preferably higher than or equal to −5.0 eV and lower than or equal to −3.0 eV. Note that as the substance having an electron-transport property in the electron-relay layer 118, a phthalocyanine-based material or a metal complex having a metal-oxygen bond and an aromatic ligand is preferably used.

A substance having a high electron-injection property can be used for the electron-injection buffer layer 119. For example, an alkali metal, an alkaline earth metal, a rare earth metal, or a compound thereof (e.g., an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate)) can be used.

In the case where the electron-injection buffer layer 119 contains the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound of the above metal (e.g., an alkali metal compound (including an oxide such as lithium oxide, a halide, and a carbonate such as lithium carbonate or cesium carbonate), an alkaline earth metal compound (including an oxide, a halide, and a carbonate), and a rare earth metal compound (including an oxide, a halide, and a carbonate)). Note that as the substance having an electron-transport property, a material similar to the above-described material used for the electron-transport layer 114 can be used.

For the second electrode 102, any of metals, alloys, electrically conductive compounds, and mixtures thereof which have a low work function (specifically, a work function of 3.8 eV or less), and the like can be used. Specific examples of such a cathode material are elements belonging to Groups 1 and 2 of the periodic table, such as alkali metals (e.g., lithium (Li) and cesium (Cs)), magnesium (Mg), calcium (Ca), and strontium (Sr), alloys thereof (e.g., MgAg and AlLi), rare earth metals such as europium (Eu) and ytterbium (Yb), and alloys thereof. However, when the electron-injection layer is provided between the second electrode 102 and the electron-transport layer, for the second electrode 102, any of a variety of conductive materials such as Al, Ag, ITO, or indium oxide-tin oxide containing silicon or silicon oxide can be used regardless of the work function. Films of these conductive materials can be formed by a dry method such as a vacuum evaporation method or a sputtering method, an inkjet method, a spin coating method, or the like. In addition, the films of these conductive materials may be formed by a wet method using a sol-gel method, or by a wet method using paste of a metal material.

Further, any of a variety of methods can be used for forming the EL layer 103, regardless of a dry method or a wet method. For example, a vacuum evaporation method, a gravure printing method, an offset printing method, a screen printing method, an inkjet method, a spin coating method, or the like may be used.

Here, a method for forming an EL layer 786 by a droplet discharge method is described with reference to FIGS. 4A to 4D. FIGS. 4A to 4D are cross-sectional views illustrating the method for forming the EL layer 786.

Figure 4A:
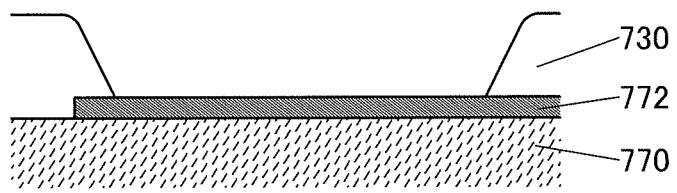
FIGS. 4A to 4D illustrate an example of a method for manufacturing a light-emitting element.
Figure 4B:
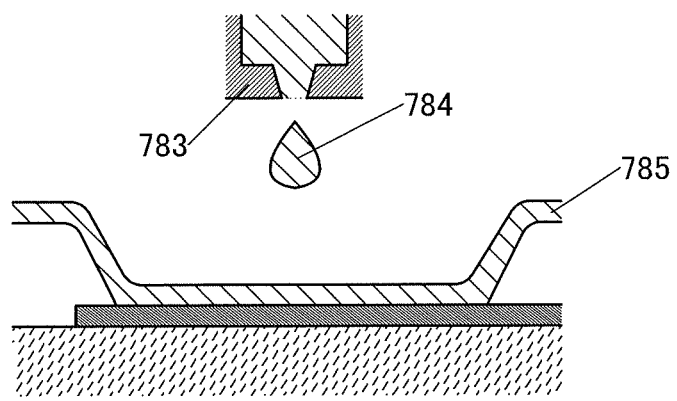

First, a conductive film 772 is formed over a planarization insulating film 770, and an insulating film 730 is formed to cover part of the conductive film 772 (see FIG. 4A).

Then, a droplet 784 is discharged to an exposed portion of the conductive film 772, which is an opening of the insulating film 730, from a droplet discharge apparatus 783, so that a layer 785 containing a composition is formed. The droplet 784 is a composition containing a solvent and is attached to the conductive film 772 (see FIG. 4B).

Note that the step of discharging the droplet 784 may be performed under reduced pressure.

Figure 4C:
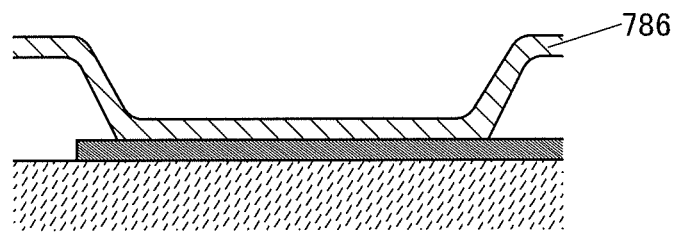

Next, the solvent is removed from the layer 785 containing a composition, and the resulting layer is solidified to form the EL layer 786 (see FIG. 4C).

The solvent may be removed by drying or heating.

Figure 4D:
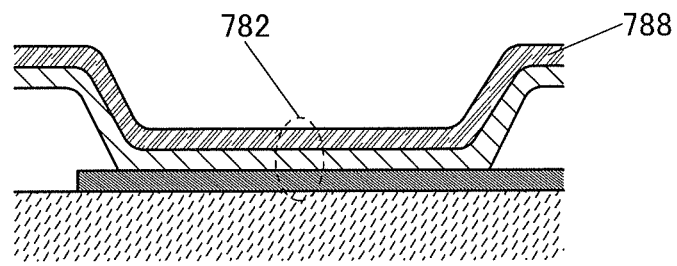

Next, a conductive film 788 is formed over the EL layer 786; thus, a light-emitting element 782 is completed (see FIG. 4D).

When the EL layer 786 is formed by a droplet discharge method as described above, the composition can be selectively discharged; accordingly, waste of material can be reduced. Furthermore, a lithography process or the like for shaping is not needed, and thus, the process can be simplified and cost reduction can be achieved.

The droplet discharge method described above is a general term for a means including a nozzle equipped with a composition discharge opening or a means to discharge droplets such as a head having one or a plurality of nozzles.

Figure 5:
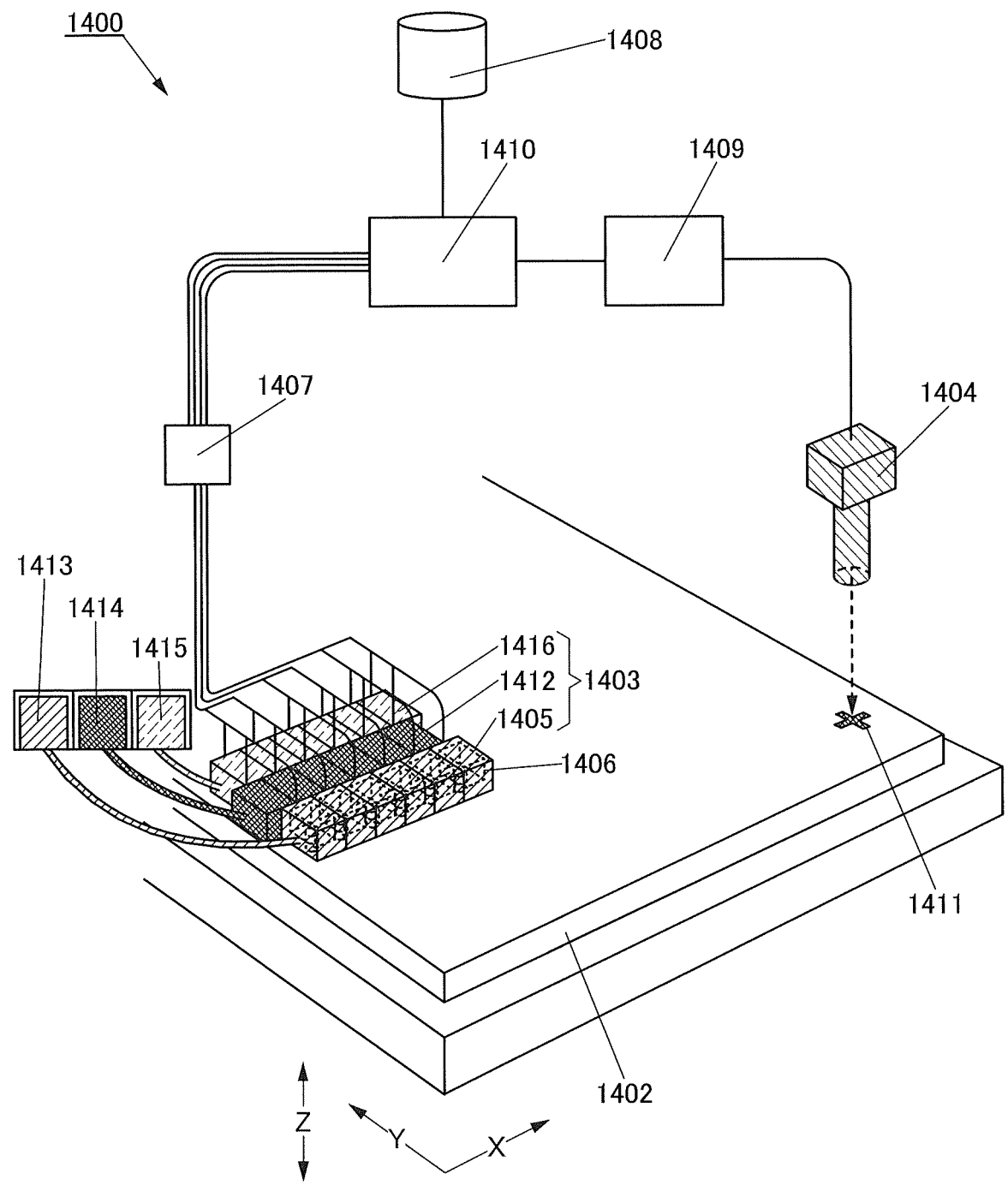
FIG. 5 illustrates an example of a manufacturing apparatus of a light-emitting element.

Next, a droplet discharge apparatus used for the droplet discharge method is described with reference to FIG. 5. FIG. 5 is a conceptual diagram illustrating a droplet discharge apparatus 1400.

The droplet discharge apparatus 1400 includes a droplet discharge means 1403. In addition, the droplet discharge means 1403 is equipped with a head 1405, a head 1412, and a head 1416.

The heads 1405 and 1412 are connected to a control means 1407, and this control means 1407 is controlled by a computer 1410; thus, a preprogrammed pattern can be drawn.

The drawing may be conducted at a timing, for example, based on a marker 1411 formed over a substrate 1402. Alternatively, the reference point may be determined on the basis of an outer edge of the substrate 1402. Here, the marker 1411 is detected by an imaging means 1404 and converted into a digital signal by an image processing means 1409. Then, the digital signal is recognized by the computer 1410, and then, a control signal is generated and transmitted to the control means 1407.

An image sensor or the like using a charge coupled device (CCD) or a complementary metal-oxide-semiconductor (CMOS) can be used as the imaging means 1404. Note that information about a pattern to be formed over the substrate 1402 is stored in a storage medium 1408, and a control signal is transmitted to the control means 1407 based on the information, so that each of the heads 1405, 1412, and 1416 of the droplet discharge means 1403 can be individually controlled. A material to be discharged is supplied to the heads 1405, 1412, and 1416 from material supply sources 1413, 1414, and 1415, respectively, through pipes.

Inside each of the heads 1405, 1412, and 1416, a space as indicated by a dotted line 1406 to be filled with a liquid material and a nozzle which is a discharge outlet are provided. Although it is not shown, an inside structure of the head 1412 is similar to that of the head 1405. When the nozzle sizes of the heads 1405 and 1412 are different from each other, different materials with different widths can be discharged simultaneously. Each head can discharge and draw a plurality of light-emitting materials. In the case of drawing over a large area, the same material can be simultaneously discharged to be drawn from a plurality of nozzles in order to improve throughput. When a large substrate is used, the heads 1405, 1412, and 1416 can freely scan the substrate in the directions indicated by arrows X, Y, and Z in FIG. 5, and a region in which a pattern is drawn can be freely set. Thus, a plurality of the same patterns can be drawn over one substrate.

A step of discharging the composition may be performed under reduced pressure. Also, a substrate may be heated when the composition is discharged. After discharging the composition, either drying or baking or the both is performed. Both the drying and baking are heat treatments but different in purpose, temperature, and time period. The steps of drying and baking are performed under normal pressure or under reduced pressure by laser irradiation, rapid thermal annealing, heating using a heating furnace, or the like. Note that the timing of the heat treatment and the number of times of the heat treatment are not particularly limited. The temperature for performing each of the steps of drying and baking in a favorable manner depends on the materials of the substrate and the properties of the composition.

In the above-described manner, the EL layer 786 can be formed with the droplet discharge apparatus.

In the case where the EL layer 786 is formed with the droplet discharge apparatus, the EL layer 786 can be formed by a wet method using a composition in which a variety of materials are dissolved in a solvent. In that case, the following various organic solvents can be used to form a coating composition: benzene, toluene, xylene, mesitylene, tetrahydrofuran, dioxane, ethanol, methanol, n-propanol, isopropanol, n-butanol, t-butanol, acetonitrile, dimethylsulfoxide, dimethylformamide, chloroform, methylene chloride, carbon tetrachloride, ethyl acetate, hexane, cyclohexane, and the like. In particular, less polar benzene derivatives such as benzene, toluene, xylene, and mesitylene are preferable because a solution with a suitable concentration can be obtained and the material contained in ink can be prevented from deteriorating due to oxidation or the like. Furthermore, to achieve a uniform film or a film with a uniform thickness, a solvent with a boiling point of 100° C. or higher is preferably used, and more preferably, toluene, xylene, or mesitylene is used.

Note that the above-described structure can be combined with any of the structures in this embodiment.

The electrode may be formed by a wet method using sol-gel method, or by a wet method using a paste of a metal material. Further, the electrode may be formed by a dry method such as a sputtering method or a vacuum evaporation method.

Light emission from the light-emitting element is extracted out through one or both of the first electrode 101 and the second electrode 102. Therefore, one or both of the first electrode 101 and the second electrode 102 are formed as a light-transmitting electrode.

The structure of the layers provided between the first electrode 101 and the second electrode 102 is not limited to the above-described structure. Preferably, a light-emitting region where holes and electrons recombine is positioned away from the first electrode 101 and the second electrode 102 so that quenching due to the proximity of the light-emitting region and a metal used for electrodes and carrier-injection layers can be prevented.

Furthermore, in order that transfer of energy from an exciton generated in the light-emitting layer can be suppressed, preferably, the hole-transport layer and the electron-transport layer which are in contact with the light-emitting layer 113, particularly a carrier-transport layer in contact with a side closer to the recombination region in the light-emitting layer 113, are formed using a substance having a wider band gap than the light-emitting substance of the light-emitting layer or the emission center substance included in the light-emitting layer.

Next, an embodiment of a light-emitting element with a structure in which a plurality of light-emitting units are stacked (this type of light-emitting element is also referred to as a stacked light-emitting element) is described with reference to FIG. 3C. This light-emitting element includes a plurality of light-emitting units between an anode and a cathode. One light-emitting unit has the same structure as the EL layer 103 illustrated in FIG. 3A. In other words, the light-emitting element illustrated in FIG. 3A or 3B includes a single light-emitting unit, and the light-emitting element illustrated in FIG. 3C includes a plurality of light-emitting units.

Figure 3C:
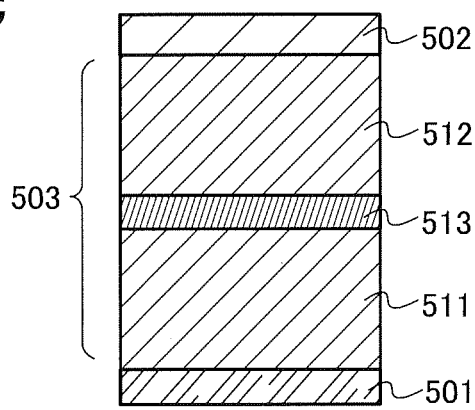

In FIG. 3C, a first light-emitting unit 511 and a second light-emitting unit 512 are stacked between a first electrode 501 and a second electrode 502, and a charge-generation layer 513 is provided between the first light-emitting unit 511 and the second light-emitting unit 512. The first electrode 501 and the second electrode 502 correspond, respectively, to the first electrode 101 and the second electrode 102 illustrated in FIG. 3A, and the materials given in the description for FIG. 3A can be used. Furthermore, the first light-emitting unit 511 and the second light-emitting unit 512 may have the same structure or different structures.

The charge-generation layer 513 has a function of injecting electrons into one of the light-emitting units and injecting holes into the other of the light-emitting units when a voltage is applied between the first electrode 501 and the second electrode 502. That is, in FIG. 3C, the charge-generation layer 513 injects electrons into the first light-emitting unit 511 and holes into the second light-emitting unit 512 when a voltage is applied so that the potential of the first electrode becomes higher than the potential of the second electrode.

The charge-generation layer 513 preferably has a structure similar to the structure of the charge-generation layer 116 described with reference to FIG. 3B. The composite material of an organic compound and a metal oxide has a high carrier-injection property and a high carrier-transport property; thus, low-voltage driving and low-current driving can be achieved. Note that when a surface of a light-emitting unit on the anode side is in contact with the charge-generation layer 513, the charge-generation layer 513 can also serve as a hole-injection layer of the light-emitting unit; thus, a hole-injection layer is not necessarily formed in the light-emitting unit.

In the case where the electron-injection buffer layer 119 is provided, the electron-injection buffer layer serves as the electron-injection layer in the light-emitting unit on the anode side and the light-emitting unit does not necessarily further need an electron-injection layer.

The light-emitting element including two light-emitting units is described with reference to FIG. 3C; however, the present invention can be similarly applied to a light-emitting element in which three or more light-emitting units are stacked. With a plurality of light-emitting units partitioned by the charge-generation layer 513 between a pair of electrodes as in the light-emitting element according to this embodiment, it is possible to provide an element which can emit light with high luminance with the current density kept low and has a long lifetime. Moreover, a light-emitting device of low power consumption, which can be driven at a low voltage, can be achieved.

When light-emitting units have different emission colors, light emission of desired color can be obtained as a whole light-emitting element. For example, it is easy to enable a light-emitting element having two light-emitting units to emit white light as the whole element when the emission colors of the first light-emitting unit are red and green and the emission color of the second light-emitting unit is blue.

<<Micro Optical Resonator (Microcavity) Structure>>

A light-emitting element with a microcavity structure is formed with the use of a reflective electrode and a semi-transmissive and semi-reflective electrode as the pair of electrodes. The reflective electrode and the semi-transmissive and semi-reflective electrode correspond to the first electrode and the second electrode described above. The light-emitting element with a microcavity structure includes at least an EL layer between the reflective electrode and the semi-transmissive and semi-reflective electrode. The EL layer includes at least a light-emitting layer functioning as a light-emitting region.

Light emitted from the light-emitting layer included in the EL layer is reflected and resonated by the reflective electrode and the semi-transmissive and semi-reflective electrode. Note that the reflective electrode has a visible light reflectivity of 40% to 100%, preferably 70% to 100% and a resistivity of $1\times10^{-2}$ Ωcm or lower. In addition, the semi-transmissive and semi-reflective electrode has a visible light reflectivity of 20% to 80%, preferably 40% to 70%, and a resistivity of $1\times10^{-2}$ Ωcm or lower.

In the light-emitting element, by changing the thicknesses of the transparent conductive film, the composite material, the carrier-transport material, and the like, the optical path length between the reflective electrode and the semi-transmissive and semi-reflective electrode can be changed. Thus, light with a wavelength that is resonated between the reflective electrode and the semi-transmissive and semi-reflective electrode can be intensified while light with a wavelength that is not resonated therebetween can be attenuated.

Note that light that is emitted from the light-emitting layer and reflected back by the reflective electrode (first reflected light) considerably interferes with light that directly enters the semi-transmissive and semi-reflective electrode from the light-emitting layer (first incident light). For this reason, the optical path length between the reflective electrode and the light-emitting layer is preferably adjusted to $(2n-1)\lambda/4$ (n is a natural number of 1 or larger and $\lambda$ is a wavelength of a color to be amplified). In that case, the phases of the first reflected light and the first incident light can be aligned with each other and the light emitted from the light-emitting layer can be further amplified.

Note that in the above structure, the EL layer may be formed of a plurality of light-emitting layers or may be a single light-emitting layer. The tandem light-emitting element described above may be combined with the EL layer; for example, a light-emitting element may have a structure in which a plurality of EL layers is provided, a charge-generation layer is provided between the EL layers, and each EL layer is formed of a plurality of light-emitting layers or a single light-emitting layer.

«Light-Emitting Device»

Figure 6A:
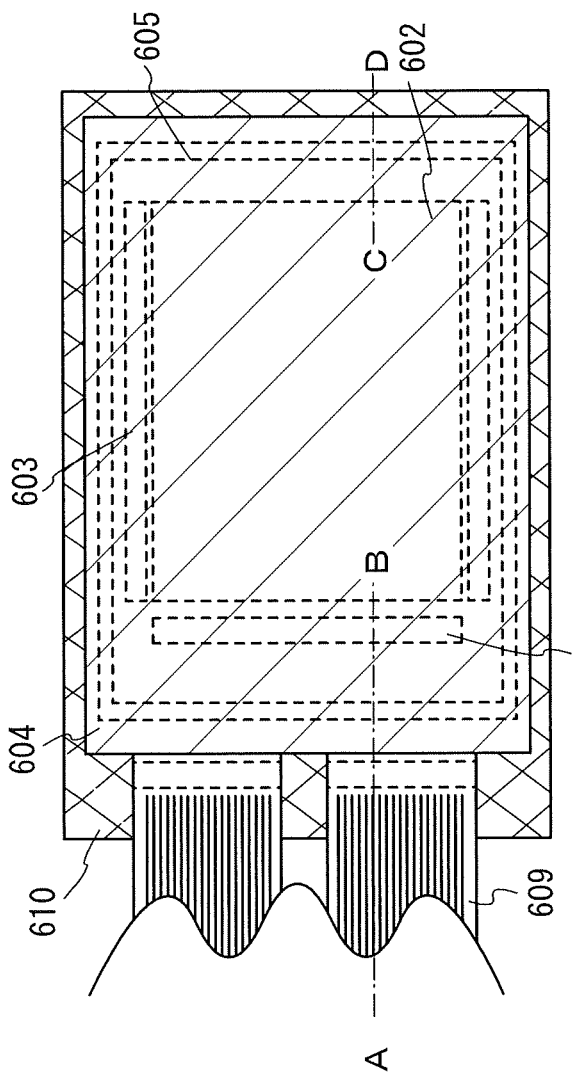
FIGS. 6A and 6B are conceptual diagrams of an active matrix light-emitting device.
Figure 6B:
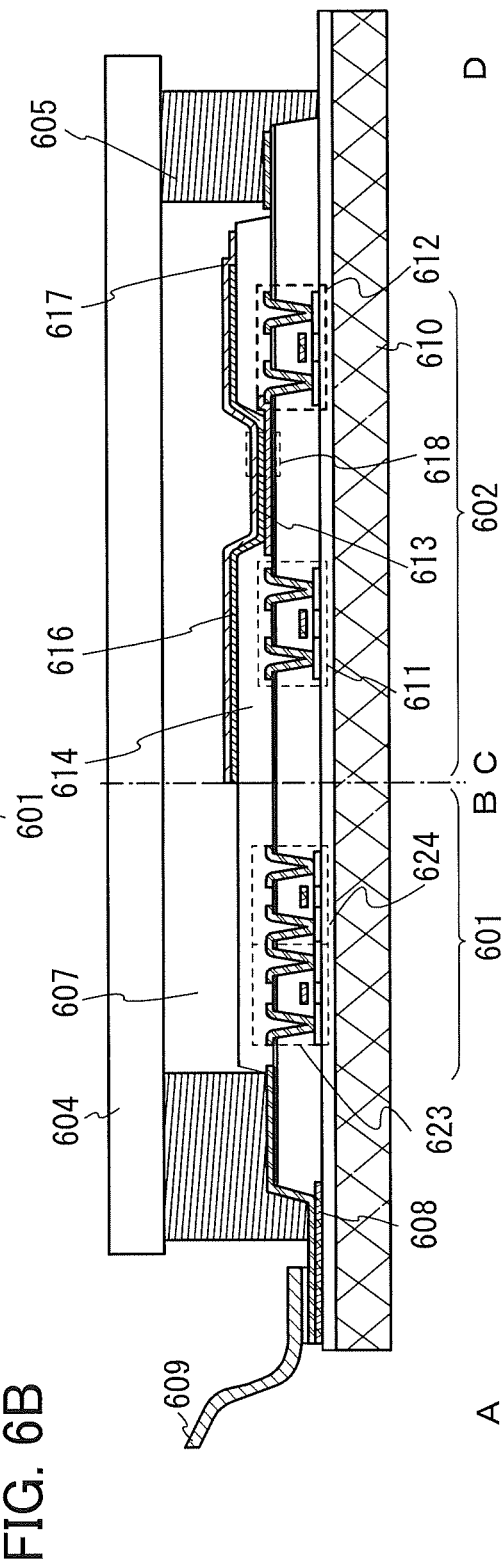

A light-emitting device of one embodiment of the present invention will be described with reference to FIGS. 6A and 6B. Note that FIG. 6A is a top view of the light-emitting device and FIG. 6B is a cross-sectional view taken along the lines A-B and C-D in FIG. 6A. The light-emitting device includes a driver circuit portion (source line driver circuit) 601, a pixel portion 602, and a driver circuit portion (gate line driver circuit) 603 which are illustrated with dotted lines. Furthermore, reference numeral 604 denotes a sealing substrate and reference numeral 605 denotes a sealant. A portion surrounded by the sealant 605 is a space 607.

Note that a lead wiring 608 is a wiring for transmitting signals to be input to the source line driver circuit 601 and the gate line driver circuit 603 and for receiving a video signal, a clock signal, a start signal, a reset signal, and the like from an FPC (flexible printed circuit) 609 functioning as an external input terminal. Although only the FPC is illustrated here, a printed wiring board (PWB) may be attached to the FPC. The light-emitting device in this specification includes, in its category, not only the light-emitting device itself but also the light-emitting device provided with the FPC or the PWB.

Next, a cross-sectional structure is described with reference to FIG. 6B. The driver circuit portion and the pixel portion are formed over an element substrate 610. Here, the source line driver circuit 601, which is the driver circuit portion, and one pixel of the pixel portion 602 are illustrated.

In the source line driver circuit 601, a CMOS circuit is formed in which an n-channel FET 623 and a p-channel FET 624 are combined. The driver circuit may be formed using various circuits such as a CMOS circuit, a PMOS circuit, or an NMOS circuit. Although a driver-integrated type where the driver circuit is formed over the substrate is described in this embodiment, a driver circuit is not necessarily formed over a substrate; a driver circuit may be formed outside a substrate.

The pixel portion 602 includes a plurality of pixels including a switching FET 611, a current controlling FET 612, and a first electrode 613 electrically connected to a drain of the current controlling FET 612. One embodiment of the present invention is not limited to this structure. The pixel portion may include three or more FETs and a capacitor in combination.

The kind and crystallinity of a semiconductor used for the FETs is not particularly limited; an amorphous semiconductor or a crystalline semiconductor may be used. Examples of the semiconductor used for the FETs include Group 13 semiconductor, Group 14 semiconductor, compound semiconductor, oxide semiconductor, and organic semiconductor materials. Oxide semiconductors are particularly preferable. Examples of the oxide semiconductor include an In—Ga oxide and an In—M—Zn oxide (M is Al, Ga, Y, Zr, La, Ce, or Nd). Note that an oxide semiconductor material that has an energy gap of 2 eV or more, preferably 2.5 eV or more, more preferably 3 eV or more is preferably used, in which case the off-state current of the transistors can be reduced.

Note that an insulator 614 is formed so as to cover an end portion of the first electrode 613. The insulator 614 can be formed using a positive photosensitive acrylic resin film here.

In order to improve the coverage, the insulator 614 is formed to have a curved surface with curvature at its upper or lower end portion. For example, in the case where a positive photosensitive acrylic resin is used for a material of the insulator 614, only the upper end portion of the insulator 614 preferably has a curved surface with a curvature radius (0.2 μm to 3 μm). Moreover, either a negative photosensitive resin or a positive photosensitive resin can be used for the insulator 614.

An EL layer 616 and a second electrode 617 are formed over the first electrode 613. The first electrode 613, the EL layer 616, and the second electrode 617 correspond, respectively, to the first electrode 101, the EL layer 103, and the second electrode 102 in FIG. 3A or 3B, and correspond, respectively, to the first electrode 501, the EL layer 503, and the second electrode 502 in FIG. 3C.

The EL layer 616 preferably contains an organometallic complex. The organometallic complex is preferably used as an emission center substance in the light-emitting layer.

The sealing substrate 604 is attached using the sealant 605 to the element substrate 610; thus, a light-emitting element 618 is provided in the space 607 surrounded by the element substrate 610, the sealing substrate 604, and the sealant 605. The space 607 is filled with filler, and may be filled with an inert gas (e.g., nitrogen or argon), the sealant 605, or the like. It is preferable that the sealing substrate be provided with a recessed portion and a drying agent be provided in the recessed portion, in which case deterioration due to influence of moisture can be suppressed.

An epoxy-based resin or glass frit is preferably used for the sealant 605. A material used for them is desirably a material which does not transmit moisture or oxygen as much as possible. As the element substrate 610 and the sealing substrate 604, for example, a glass substrate, a quartz substrate, or a plastic substrate formed of fiber reinforced plastic (FRP), polyvinyl fluoride (PVF), polyester, or acrylic can be used.

Note that in this specification and the like, a transistor or a light-emitting element can be formed using any of a variety of substrates, for example. The type of a substrate is not limited to a certain type. As the substrate, a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, a base material film, or the like can be used, for example. As an example of a glass substrate, a barium borosilicate glass substrate, an aluminoborosilicate glass substrate, a soda lime glass substrate, or the like can be given. Examples of the flexible substrate, the attachment film, the base material film, or the like are as follows: plastic typified by polyethylene terephthalate (PET), polyethylene naphthalate (PEN), and polyether sulfone (PES). Another example is a synthetic resin such as acrylic. Alternatively, polytetrafluoroethylene (PTFE), polypropylene, polyester, polyvinyl fluoride, polyvinyl chloride, or the like can be used. Alternatively, polyamide, polyimide, aramid, epoxy, an inorganic film formed by evaporation, paper, or the like can be used. Specifically, the use of semiconductor substrates, single crystal substrates, SOI substrates, or the like enables the manufacture of small-sized transistors with a small variation in characteristics, size, shape, or the like and with high current capability. A circuit using such transistors achieves lower power consumption of the circuit or higher integration of the circuit.

Alternatively, a flexible substrate may be used as the substrate, and the transistor or the light-emitting element may be provided directly over the flexible substrate. Still alternatively, a separation layer may be provided between a substrate and the transistor or between the substrate and the light-emitting element. The separation layer can be used when part or the whole of a semiconductor device formed over the separation layer is separated from the substrate and transferred onto another substrate. In such a case, the transistor can be transferred to a substrate having low heat resistance or a flexible substrate as well. For the above separation layer, a stack including inorganic films, which are a tungsten film and a silicon oxide film, or an organic resin film of polyimide or the like formed over a substrate can be used, for example.

In other words, a transistor or a light-emitting element may be formed using one substrate, and then transferred to another substrate. Examples of the substrate to which the transistor or the light-emitting element is transferred include, in addition to the above-described substrates over which transistors can be formed, a paper substrate, a cellophane substrate, an aramid film substrate, a polyimide film substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, and a rubber substrate. When such a substrate is used, a transistor with excellent properties or a transistor with low power consumption can be formed, a device with high durability and high heat resistance can be provided, or a reduction in weight or thickness can be achieved.

FIGS. 7A and 7B each illustrate an example of a light-emitting device in which full color display is achieved by forming a light-emitting element exhibiting white light emission and using coloring layers (color filters) and the like. In FIG. 7A, a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition 1025, an EL layer 1028, a second electrode 1029 of the light-emitting elements, a sealing substrate 1031, a sealant 1032, and the like are illustrated.

In FIG. 7A, coloring layers (a red coloring layer 1034R, a green coloring layer 1034G, and a blue coloring layer 1034B) are provided on a transparent base material 1033. A black layer (a black matrix) 1035 may be additionally provided. The transparent base material 1033 provided with the coloring layers and the black layer is positioned and fixed to the substrate 1001. Note that the coloring layers and the black layer are covered with an overcoat layer 1036. In FIG. 7A, light emitted from some of the light-emitting layers does not pass through the coloring layers, while light emitted from the others of the light-emitting layers passes through the coloring layers. Since light which does not pass through the coloring layers is white and light which passes through any one of the coloring layers is red, blue, or green, an image can be displayed using pixels of the four colors.

FIG. 7B illustrates an example in which the coloring layers (the red coloring layer 1034R, the green coloring layer 1034G, and the blue coloring layer 1034B) are formed between the gate insulating film 1003 and the first interlayer insulating film 1020. As in this structure, the coloring layers may be provided between the substrate 1001 and the sealing substrate 1031.

Figure 8:
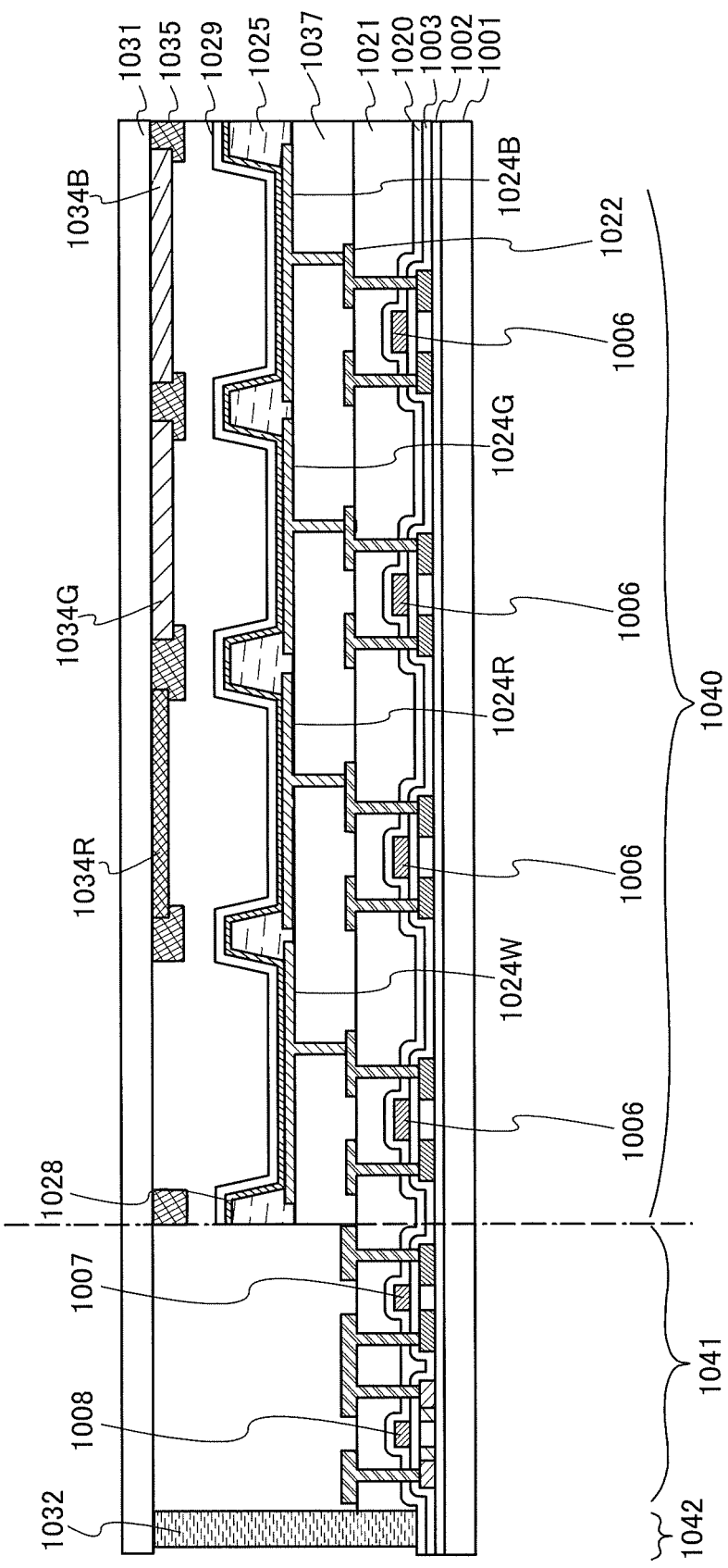
FIG. 8 is a conceptual diagram of an active matrix light-emitting device.

The above-described light-emitting device has a structure in which light is extracted from the substrate 1001 side where the FETs are formed (a bottom emission structure), but may have a structure in which light is extracted from the sealing substrate 1031 side (a top emission structure). FIG. 8 is a cross-sectional view of a light-emitting device having a top emission structure. In that case, a substrate which does not transmit light can be used as the substrate 1001. The process up to the step of forming of a connection electrode which connects the FET and the anode of the light-emitting element is performed in a manner similar to that of the light-emitting device having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film, or can be formed using any other various materials.

The first electrodes 1024W, 1024R, 1024G, and 1024B of the light-emitting elements each function as an anode here, but may function as a cathode. Furthermore, in the case of the light-emitting device having a top emission structure as illustrated in FIG. 8, the first electrodes are preferably reflective electrodes. The EL layer 1028 is formed to have a structure similar to the structure of the EL layer 103 in FIG. 3A or 3B or the EL layer 503 in FIG. 3C, with which white light emission can be obtained.

In the case of a top emission structure as illustrated in FIG. 8, sealing can be performed with the sealing substrate 1031 on which the coloring layers (the red coloring layer 1034R, the green coloring layer 1034G, and the blue coloring layer 1034B) are provided. The sealing substrate 1031 may be provided with the black layer (the black matrix) 1035 which is positioned between pixels. The coloring layers (the red coloring layer 1034R, the green coloring layer 1034G, and the blue coloring layer 1034B) and the black layer may be covered with the overcoat layer. Note that a light-transmitting substrate is used as the sealing substrate 1031.

Although an example in which full color display is performed using four colors of red, green, blue, and white is shown here, there is no particular limitation and full color display using three colors of red, green, and blue or four colors of red, green, blue, and yellow may be performed.

Figure 9A:
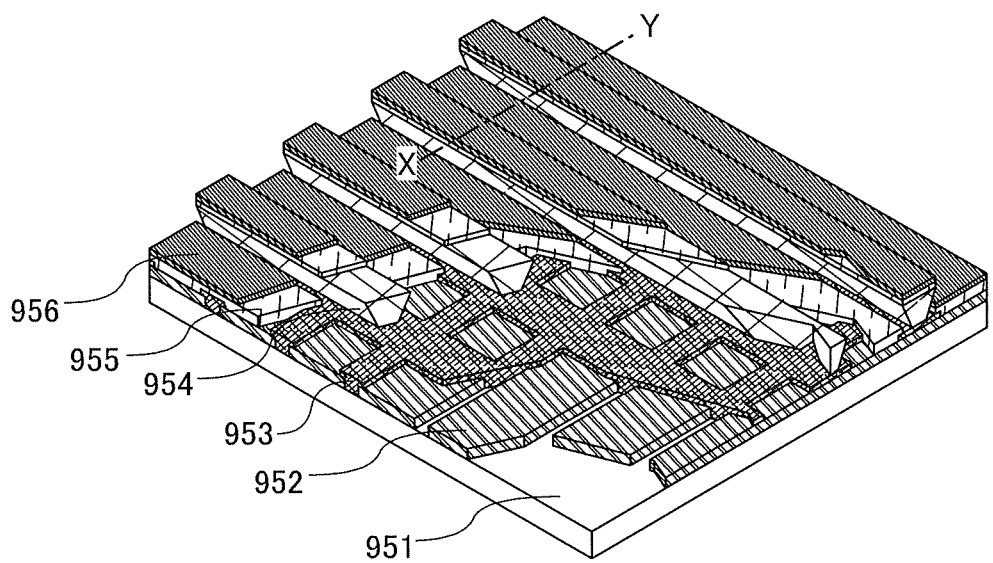
FIGS. 9A and 9B are conceptual diagrams of a passive matrix light-emitting device.
Figure 9B:
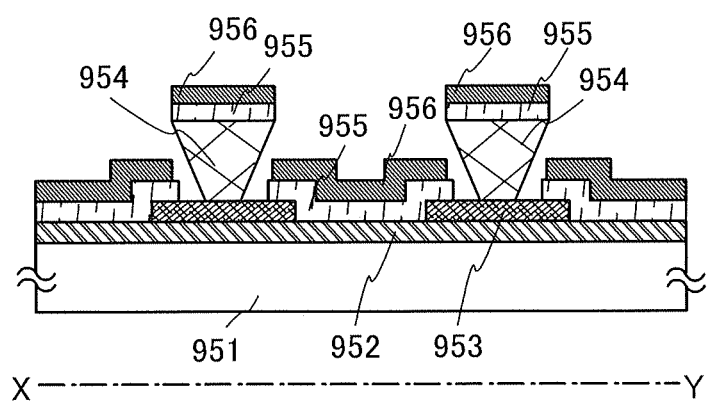

FIGS. 9A and 9B illustrate a passive matrix light-emitting device of one embodiment of the present invention. FIG. 9A is a perspective view of a light-emitting device, and FIG. 9B is a cross-sectional view taken along the line X-Y of FIG. 9A. In FIGS. 9A and 9B, an EL layer 955 is provided between an electrode 952 and an electrode 956 over a substrate 951. An end portion of the electrode 952 is covered with an insulating layer 953. A partition layer 954 is provided over the insulating layer 953. Sidewalls of the partition layer 954 are aslope such that the distance between the sidewalls is gradually narrowed toward the surface of the substrate. That is, a cross section in a short side direction of the partition layer 954 is a trapezoidal shape, and a lower side (the side facing the same direction as the plane direction of the insulating layer 953 and touching the insulating layer 953) is shorter than an upper side (the side facing the same direction as the plane direction of the insulating layer 953, and not touching the insulating layer 953). By providing the partition layer 954 in this manner, defects of the light-emitting element due to static charge and the like can be prevented.

Since many minute light-emitting elements arranged in a matrix can be controlled with the FETs formed in the pixel portion, the above-described light-emitting device can be suitably used as a display device for displaying images.

«Lighting Device»

Figure 10A:
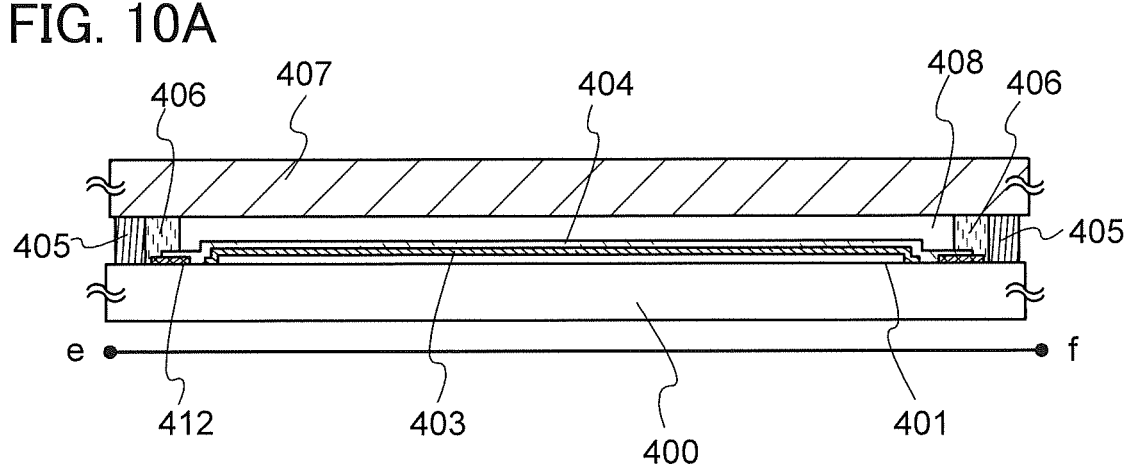
FIGS. 10A and 10B illustrate a lighting device.
Figure 10B:
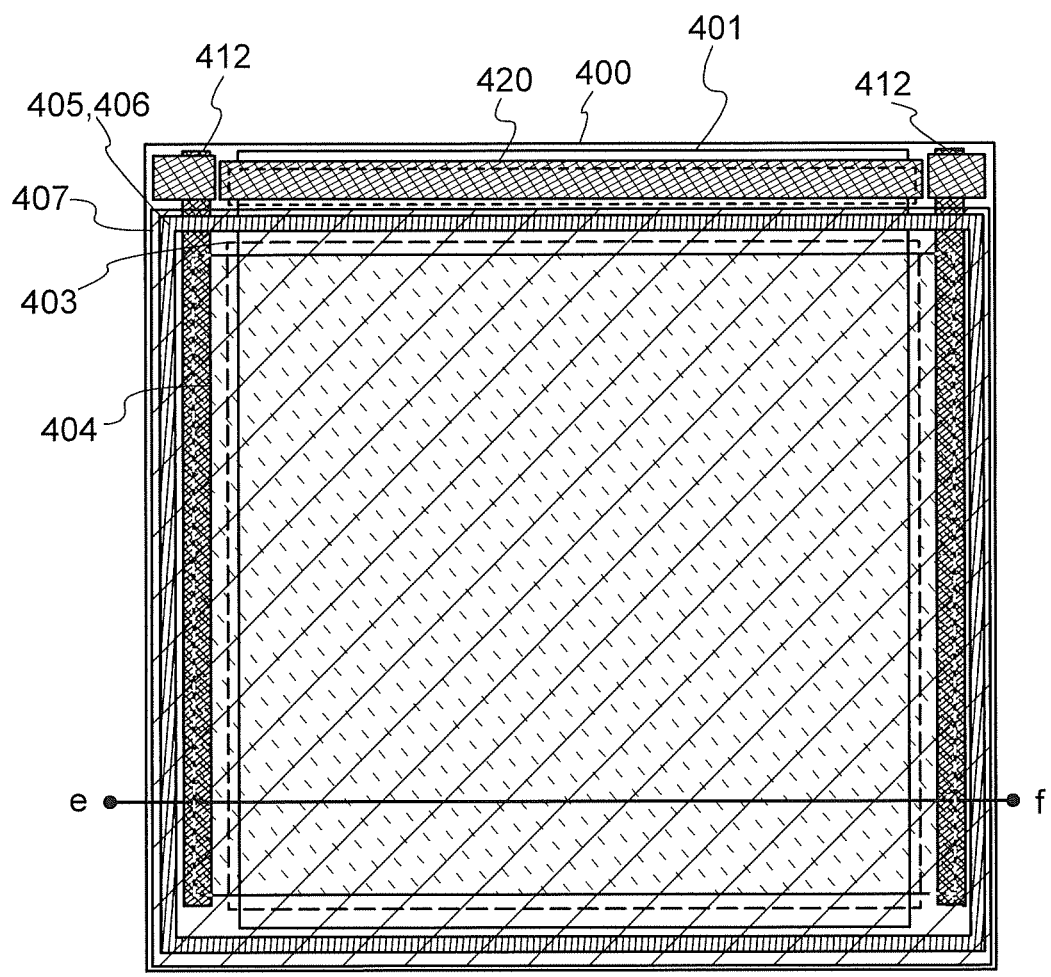

A lighting device of one embodiment of the present invention is described with reference to FIGS. 10A and 10B. FIG. 10B is a top view of the lighting device, and FIG. 10A is a cross-sectional view taken along the line e-f in FIG. 10B.

In the lighting device, a first electrode 401 is formed over a substrate 400 which is a support and has a light-transmitting property. The first electrode 401 corresponds to the first electrode 101 in FIGS. 3A and 3B. When light is extracted through the first electrode 401 side, the first electrode 401 is formed using a material having a light-transmitting property.

A pad 412 for applying voltage to a second electrode 404 is provided over the substrate 400.

An EL layer 403 is formed over the first electrode 401. The EL layer 403 corresponds to, for example, the EL layer 103 in FIGS. 3A and 3B or the EL layer 503 in FIG. 3C. For these structures, the corresponding description can be referred to.

The second electrode 404 is formed to cover the EL layer 403. The second electrode 404 corresponds to the second electrode 102 in FIG. 3A. The second electrode 404 contains a material having high reflectivity when light is extracted through the first electrode 401 side. The second electrode 404 is connected to the pad 412, whereby voltage is applied thereto.

A light-emitting element is formed with the first electrode 401, the EL layer 403, and the second electrode 404. The light-emitting element is fixed to a sealing substrate 407 with sealants 405 and 406 and sealing is performed, whereby the lighting device is completed. It is possible to use only either the sealant 405 or the sealant 406. In addition, the inner sealant 406 can be mixed with a desiccant that enables moisture to be adsorbed, which results in improved reliability.

When part of the pad 412 and part of the first electrode 401 are extended to the outside of the sealants 405 and 406, the extended parts can function as external input terminals. An IC chip 420 mounted with a converter or the like may be provided over the external input terminals.

«Display Device»

An example of a display panel that can be used for a display portion or the like in a display device including the semiconductor device of one embodiment of the present invention will be described below with reference to FIG. 18 and FIG. 19. The display panel exemplified below includes both a reflective liquid crystal element and a light-emitting element and can display an image in both the transmissive mode and the reflective mode.

<Structure Example of Display Panel>

Figure 18:
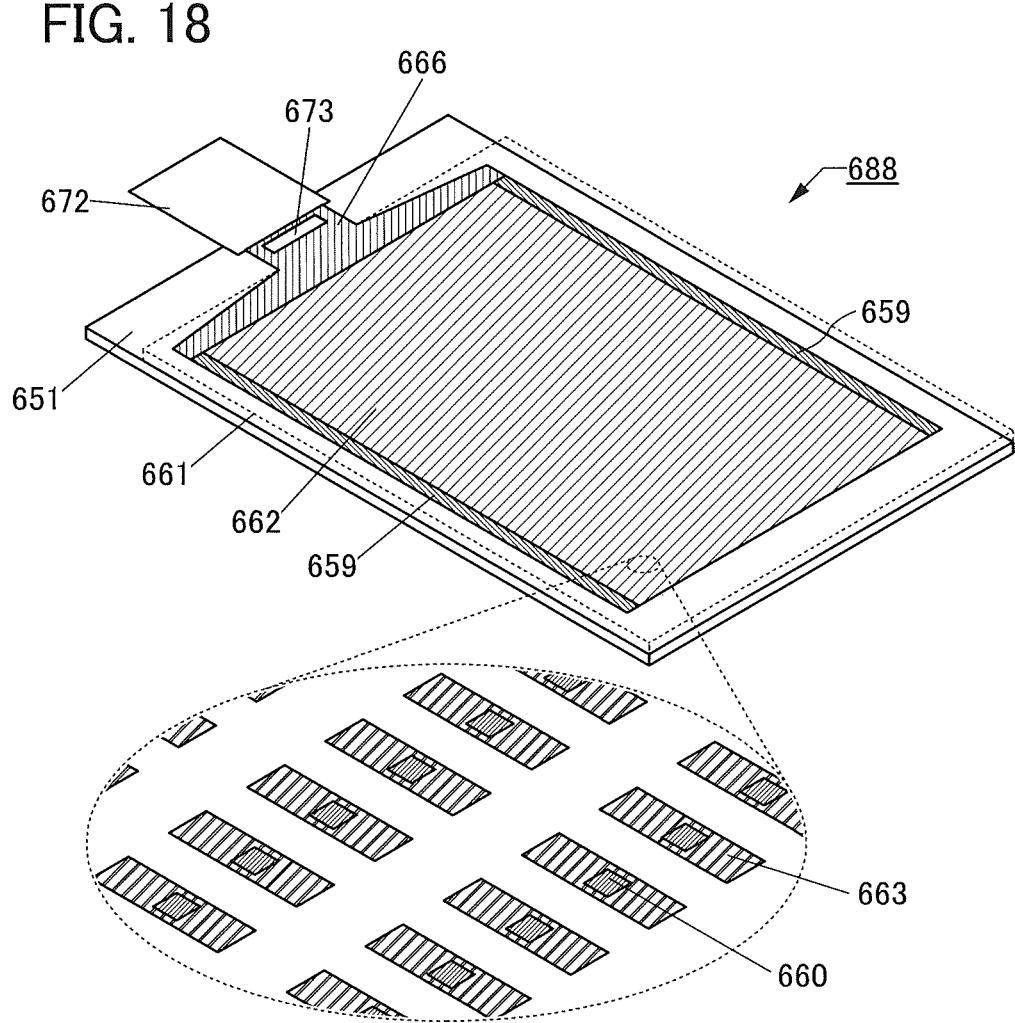
FIG. 18 illustrates a structure example of a display panel.

FIG. 18 is a schematic perspective view illustrating a display panel 688 of one embodiment of the present invention. In the display panel 688, a substrate 651 and a substrate 661 are attached to each other. In FIG. 18, the substrate 661 is denoted by a dashed line.

The display panel 688 includes a display portion 662, a circuit 659, a wiring 666, and the like. The substrate 651 is provided with the circuit 659, the wiring 666, a conductive film 663 which serves as a pixel electrode, and the like. In the example of FIG. 18, an IC 673 and an FPC 672 are mounted on the substrate 651. Thus, the structure illustrated in FIG. 18 can be referred to as a display module including the display panel 688, the FPC 672, and the IC 673.

As the circuit 659, for example, a circuit functioning as a scan line driver circuit can be used.

The wiring 666 has a function of supplying a signal or electric power to the display portion 662 or the circuit 659. The signal or electric power is input to the wiring 666 from the outside through the FPC 672 or from the IC 673.

FIG. 18 shows an example in which the IC 673 is provided on the substrate 651 by a chip on glass (COG) method or the like. As the IC 673, an IC functioning as a scan line driver circuit, a signal line driver circuit, or the like can be used. Note that it is possible that the IC 673 is not provided when, for example, the display panel 688 includes circuits serving as a scan line driver circuit and a signal line driver circuit and when the circuits serving as a scan line driver circuit and a signal line driver circuit are provided outside and a signal for driving the display panel 688 is input through the FPC 672. Alternatively, the IC 673 may be mounted on the FPC 672 by a chip on film (COF) method or the like.

FIG. 18 also shows an enlarged view of part of the display portion 662. The conductive films 663 included in a plurality of display elements are arranged in a matrix in the display portion 662. The conductive film 663 has a function of reflecting visible light and serves as a reflective electrode of a liquid crystal element 640 described later.

As illustrated in FIG. 18, the conductive film 663 has an opening. A light-emitting element 660 is positioned closer to the substrate 651 than the conductive film 663 is. Light is emitted from the light-emitting element 660 to the substrate 661 side through the opening in the conductive film 663. When the light-emitting element of one embodiment of the present invention is used as the light-emitting element 660, a display panel with a long lifetime can be provided. A display panel including a light-emitting element with high emission efficiency can be provided. Furthermore, when the light-emitting element of one embodiment of the present invention is used as the light-emitting element 660, a display panel including a blue light-emitting element with high emission efficiency can be provided.

<Cross-Sectional Structure Example>

Figure 19:
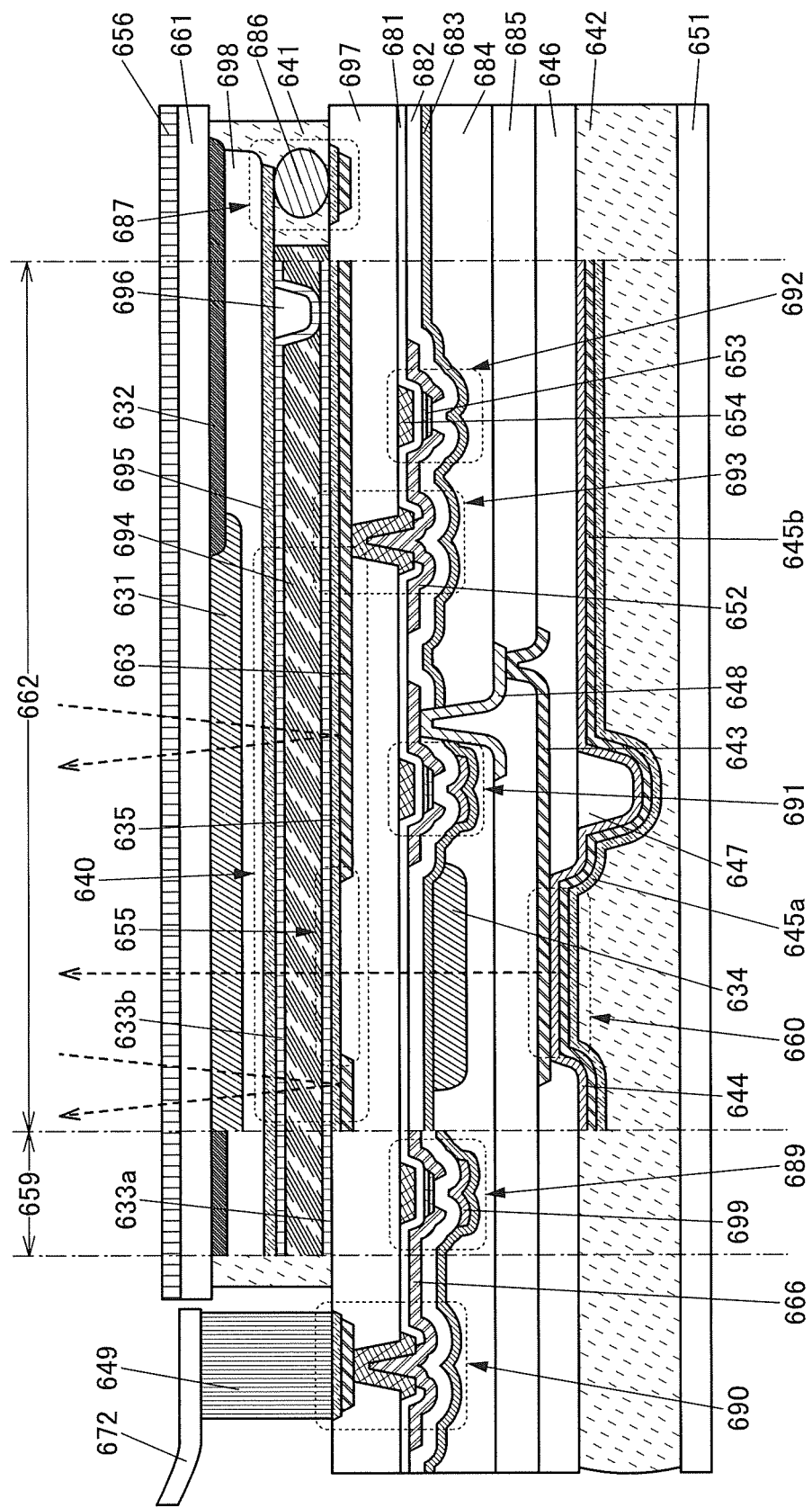
FIG. 19 illustrates a structure example of a display panel.

FIG. 19 shows an example of cross sections of part of a region including the FPC 672, part of a region including the circuit 659, and part of a region including the display portion 662 of the display panel illustrated in FIG. 18.

The display panel includes an insulating film 697 between the substrates 651 and 661. The display panel also includes the light-emitting element 660, a transistor 689, a transistor 691, a transistor 692, a coloring layer 634, and the like between the substrate 651 and the insulating film 697. Furthermore, the display panel includes the liquid crystal element 640, a coloring layer 631, and the like between the insulating film 697 and the substrate 661. The substrate 661 and the insulating film 697 are bonded with an adhesive layer 641. The substrate 651 and the insulating film 697 are bonded with an adhesive layer 642.

The transistor 692 is electrically connected to the liquid crystal element 640 and the transistor 691 is electrically connected to the light-emitting element 660. Since the transistors 691 and 692 are formed on a surface of the insulating film 697 that is on the substrate 651 side, the transistors 691 and 692 can be formed through the same process.

The substrate 661 is provided with the coloring layer 631, a light-blocking film 632, an insulating film 698, a conductive film 695 serving as a common electrode of the liquid crystal element 640, an alignment film 633b, an insulating film 696, and the like. The insulating film 696 serves as a spacer for holding a cell gap of the liquid crystal element 640.

Insulating layers such as an insulating film 681, an insulating film 682, an insulating film 683, an insulating film 684, and an insulating film 685 are provided on the substrate 651 side of the insulating film 697. Part of the insulating film 681 functions as a gate insulating layer of each transistor. The insulating films 682, 683, and 684 are provided to cover each transistor. The insulating film 685 is provided to cover the insulating film 684. The insulating films 684 and 685 each function as a planarization layer. Note that here, the three insulating layers, the insulating films 682, 683, and 684, are provided to cover the transistors and the like; however, one embodiment of the present invention is not limited to this example, and four or more insulating layers, a single insulating layer, or two insulating layers may be provided. The insulating film 684 functioning as a planarization layer is not necessarily provided.

The transistors 689, 691, and 692 each include a conductive film 654 part of which functions as a gate, a conductive film 652 part of which functions as a source or a drain, and a semiconductor film 653. Here, a plurality of layers obtained by processing the same conductive film are shown with the same hatching pattern.

The liquid crystal element 640 is a reflective liquid crystal element. The liquid crystal element 640 has a stacked structure of a conductive film 635, a liquid crystal layer 694, and the conductive film 695. In addition, the conductive film 663 which reflects visible light is provided in contact with the surface of the conductive film 635 that faces the substrate 651. The conductive film 663 includes an opening 655. The conductive films 635 and 695 contain a material that transmits visible light. In addition, an alignment film 633a is provided between the liquid crystal layer 694 and the conductive film 635 and the alignment film 633b is provided between the liquid crystal layer 694 and the conductive film 695. A polarizing plate 656 is provided on an outer surface of the substrate 661.

In the liquid crystal element 640, the conductive film 663 has a function of reflecting visible light and the conductive film 695 has a function of transmitting visible light. Light entering from the substrate 661 side is polarized by the polarizing plate 656, passes through the conductive film 695 and the liquid crystal layer 694, and is reflected by the conductive film 663. Then, the light passes through the liquid crystal layer 694 and the conductive film 695 again and reaches the polarizing plate 656. In this case, the alignment of the liquid crystal is controlled with a voltage that is applied between the conductive film 663 and the conductive film 695, and thus optical modulation of light can be controlled. That is, the intensity of light emitted through the polarizing plate 656 can be controlled. Light excluding light in a particular wavelength region is absorbed by the coloring layer 631, and thus, red light is emitted, for example.

The light-emitting element 660 is a bottom-emission light-emitting element. The light-emitting element 660 has a structure in which a conductive film 643, an EL layer 644, and a conductive film 645b are stacked in this order from the insulating film 697 side. In addition, a conductive film 645a is provided to cover the conductive film 645b. The conductive film 645b contains a material reflecting visible light, and the conductive films 643 and 645a contain a material transmitting visible light. Light is emitted from the light-emitting element 660 to the substrate 661 side through the coloring layer 634, the insulating film 697, the opening 655, the conductive film 695, and the like.

Here, as illustrated in FIG. 19, the conductive film 635 transmitting visible light is preferably provided for the opening 655. Accordingly, the liquid crystal layer 694 is aligned in a region overlapping with the opening 655 as well as in the other regions, so that undesired light leakage due to an alignment defect of the liquid crystal in the boundary portion of these regions can be prevented.

As the polarizing plate 656 provided on an outer surface of the substrate 661, a linear polarizing plate or a circularly polarizing plate can be used. An example of the circularly polarizing plate is a stack including a linear polarizing plate and a quarter-wave retardation plate. Such a structure can reduce reflection of external light. The cell gap, alignment, drive voltage, and the like of the liquid crystal element used as the liquid crystal element 640 are controlled depending on the kind of the polarizing plate so that a desirable contrast can be obtained.

In addition, an insulating film 647 is provided on the insulating film 646 covering an end portion of the conductive film 643. The insulating film 647 has a function as a spacer for preventing the insulating film 697 and the substrate 651 from getting closer than necessary. In the case where the EL layer 644 or the conductive film 645a is formed using a blocking mask (metal mask), the insulating film 647 may have a function of preventing the blocking mask from being in contact with a surface on which the EL layer 644 or the conductive film 645a is formed. Note that the insulating film 647 is not necessarily provided.

One of a source and a drain of the transistor 691 is electrically connected to the conductive film 643 of the light-emitting element 660 through a conductive film 648.

One of a source and a drain of the transistor 692 is electrically connected to the conductive film 663 through a connection portion 693. The conductive films 663 and 635 are in contact with and electrically connected to each other. Here, in the connection portion 693, the conductive layers provided on both surfaces of the insulating film 697 are connected to each other through an opening in the insulating film 697.

A connection portion 690 is provided in a region of the substrate 651 that does not overlap the substrate 661. The connection portion 690 is electrically connected to the FPC 672 through a connection layer 649. The connection portion 690 has a structure similar to that of the connection portion 693. On the top surface of the connection portion 690, a conductive layer obtained by processing the same conductive film as the conductive film 635 is exposed. Thus, the connection portion 690 and the FPC 672 can be electrically connected to each other through the connection layer 649.

A connection portion 687 is provided in part of a region where the adhesive layer 641 is provided. In the connection portion 687, the conductive layer obtained by processing the same conductive film as the conductive film 635 is electrically connected to part of the conductive film 695 with a connector 686. Accordingly, a signal or a potential input from the FPC 672 connected to the substrate 651 side can be supplied to the conductive film 695 formed on the substrate 661 side through the connection portion 687.

As the connector 686, a conductive particle can be used, for example. As the conductive particle, a particle of an organic resin, silica, or the like coated with a metal material can be used. It is preferable to use nickel or gold as the metal material because contact resistance can be reduced. It is also preferable to use a particle coated with layers of two or more kinds of metal materials, such as a particle coated with nickel and further with gold. As the connector 686, a material capable of elastic deformation or plastic deformation is preferably used. As illustrated in FIG. 19, the connector 686 which is the conductive particle has a shape that is vertically crushed in some cases. With the crushed shape, the contact area between the connector 686 and a conductive layer electrically connected to the connector 686 can be increased, thereby reducing contact resistance and suppressing the generation of problems such as disconnection.

The connector 686 is preferably provided so as to be covered with the adhesive layer 641. For example, the connectors 686 are provided in the adhesive layer 641 before curing of the adhesive layer 641.

FIG. 19 illustrates an example of the circuit 659 in which the transistor 689 is provided.

In FIG. 19, as a structure example of the transistors 689 and 691, the semiconductor film 653 where a channel is formed is provided between two gates. One gate is formed using the conductive film 654 and the other gate is formed using a conductive film 699 overlapping with the semiconductor film 653 with the insulating film 682 provided therebetween. Such a structure enables the control of threshold voltages of a transistor. In that case, the two gates may be connected to each other and supplied with the same signal to operate the transistor. Such a transistor can have higher field-effect mobility and thus have higher on-state current than other transistors. Consequently, a circuit capable of high-speed operation can be obtained. Furthermore, the area occupied by a circuit portion can be reduced. The use of the transistor having a high on-state current can reduce signal delay in wirings and can reduce display unevenness even in a display panel that has an increased number of wirings with an increase in size or resolution.

Note that the transistor included in the circuit 659 and the transistor included in the display portion 662 may have the same structure. A plurality of transistors included in the circuit 659 may have the same structure or different structures. A plurality of transistors included in the display portion 662 may have the same structure or different structures.

A material through which impurities such as water and hydrogen do not easily diffuse is preferably used for at least one of the insulating films 682 and 683 which cover the transistors. That is, the insulating film 682 or the insulating film 683 can function as a barrier film. Such a structure can effectively suppress the diffusion of the impurities into the transistors from the outside, and a highly reliable display panel can be provided.

The insulating film 698 is provided on the substrate 661 side to cover the coloring layer 631 and the light-blocking film 632. The insulating film 698 may have a function as a planarization layer. The insulating film 698 enables the conductive film 695 to have an almost flat surface, resulting in a uniform alignment state of the liquid crystal layer 694.

An example of the method for manufacturing the display panel 688 is described. For example, the conductive film 635, the conductive film 663, and the insulating film 697 are formed in order over a support substrate provided with a separation layer, and the transistor 691, the transistor 692, the light-emitting element 660, and the like are formed. Then, the substrate 651 and the support substrate are bonded with the adhesive layer 642. After that, separation is performed at the interface between the separation layer and each of the insulating film 697 and the conductive film 635, whereby the support substrate and the separation layer are removed. Separately, the coloring layer 631, the light-blocking film 632, the conductive film 695, and the like are formed over the substrate 661 in advance. Then, the liquid crystal is dropped onto the substrate 651 or 661 and the substrates 651 and 661 are bonded with the adhesive layer 641, whereby the display panel 688 can be manufactured.

A material for the separation layer can be selected such that separation at the interface with the insulating film 697 and the conductive film 635 occurs. In particular, it is preferable that a stack of a layer including a high-melting-point metal material, such as tungsten, and a layer including an oxide of the metal material be used as the separation layer, and a stack of a plurality of layers, such as a silicon nitride layer, a silicon oxynitride layer, and a silicon nitride oxide layer be used as the insulating film 697 over the separation layer. The use of the high-melting-point metal material for the separation layer can increase the formation temperature of a layer formed in a later step, which reduces impurity concentration and achieves a highly reliable display panel.

As the conductive film 635, an oxide or a nitride such as a metal oxide, a metal nitride, or an oxide semiconductor with reduced resistance is preferably used. In the case of using an oxide semiconductor, a material in which at least one of the concentrations of hydrogen, boron, phosphorus, nitrogen, and other impurities and the number of oxygen vacancies is made to be higher than those in a semiconductor layer of a transistor is used for the conductive film 635.

<Components>

The above components will be described below. Note that the description of the structures having functions similar to those described above is omitted.

[Adhesive Layer]

As the adhesive layer, a variety of curable adhesives such as a reactive curable adhesive, a thermosetting adhesive, an anaerobic adhesive, and a photocurable adhesive such as an ultraviolet curable adhesive can be used. Examples of these adhesives include an epoxy resin, an acrylic resin, a silicone resin, a phenol resin, a polyimide resin, an imide resin, a polyvinyl chloride (PVC) resin, a polyvinyl butyral (PVB) resin, and an ethylene vinyl acetate (EVA) resin. In particular, a material with low moisture permeability, such as an epoxy resin, is preferred. Alternatively, a two-component type resin may be used. Further alternatively, an adhesive sheet or the like may be used.

Furthermore, the resin may include a drying agent. For example, a substance that adsorbs moisture by chemical adsorption, such as an oxide of an alkaline earth metal (e.g., calcium oxide or barium oxide), can be used. Alternatively, a substance that adsorbs moisture by physical adsorption, such as zeolite or silica gel, may be used. The drying agent is preferably included because it can prevent impurities such as moisture from entering the element, thereby improving the reliability of the display panel.

In addition, it is preferable to mix a filler with a high refractive index or light-scattering member into the resin, in which case light extraction efficiency can be enhanced. For example, titanium oxide, barium oxide, zeolite, zirconium, or the like can be used.

[Connection Layer]

As the connection layer, an anisotropic conductive film (ACF), an anisotropic conductive paste (ACP), or the like can be used.

[Coloring Layer]

Examples of the material that can be used for the coloring layers include a metal material, a resin material, and a resin material containing a pigment or dye.

[Light-Blocking Layer]

Examples of the material that can be used for the light-blocking layer include carbon black, titanium black, a metal, a metal oxide, and a composite oxide containing a solid solution of a plurality of metal oxides. The light-blocking layer may be a film containing a resin material or a thin film of an inorganic material such as a metal. Stacked films containing the material of the coloring layer can also be used for the light-blocking layer. For example, a stacked-layer structure of a film containing a material for a coloring layer that transmits light of a certain color and a film containing a material for a coloring layer that transmits light of another color can be employed. The coloring layer and the light-blocking layer are preferably formed using the same material so that the same manufacturing apparatus can be used and the process can be simplified.

The above is the description of the components.

<Manufacturing Method Example>

A manufacturing method example of a display panel using a flexible substrate is described.

Here, layers including a display element, a circuit, a wiring, an electrode, optical members such as a coloring layer and a light-blocking layer, an insulating layer, and the like, are collectively referred to as an element layer. The element layer includes, for example, a display element, and may additionally include a wiring electrically connected to the display element or an element such as a transistor used in a pixel or a circuit.

In addition, here, a flexible member that supports the element layer at the time when the display element is completed (the manufacturing process is finished) is referred to as a substrate. For example, a substrate includes an extremely thin film with a thickness greater than or equal to 10 mn and less than or equal to 300 μm.

As a method for forming an element layer over a flexible substrate provided with an insulating surface, typically, the following two methods can be employed. One of them is to form an element layer directly on the substrate. The other method is to form an element layer over a support substrate that is different from the substrate and then to separate the element layer from the support substrate to be transferred to the substrate. Although not described in detail here, in addition to the above two methods, there is a method in which an element layer is formed over a substrate that does not have flexibility and the substrate is thinned by polishing or the like to have flexibility.

In the case where a material of the substrate has a resistance to heat applied in the forming process of the element layer, it is preferable that the element layer be formed directly on the substrate, in which case a manufacturing process can be simplified. At this time, the element layer is preferably formed in a state where the substrate is fixed to the supporting base, in which case transfer thereof in an apparatus and between apparatuses can be easy.

In the case of employing the method in which the element layer is formed over the supporting base and then transferred to the substrate, first, a separation layer and an insulating layer are stacked over the supporting base, and then the element layer is formed over the insulating layer. Next, the element layer is separated from the supporting base and then transferred to the substrate. At this time, a material may be selected so that the separation occurs at an interface between the supporting base and the separation layer, at an interface between the separation layer and the insulating layer, or in the separation layer. In this method, a high heat resistant material is preferably used for the supporting base or the separation layer, in which case the upper limit of the temperature applied when the element layer is formed can be increased, and an element layer including a more highly reliable element can be formed.

For example, it is preferable that a stack of a layer containing a high-melting-point metal material, such as tungsten, and a layer containing an oxide of the metal material be used as the separation layer, and a stack of a plurality of layers, such as a silicon oxide layer, a silicon nitride layer, a silicon oxynitride layer, and a silicon nitride oxide layer be used as the insulating layer over the separation layer.

The element layer and the supporting base can be separated by applying mechanical power, by etching the separation layer, by injecting a liquid into the separation interface, or the like. Alternatively, separation may be performed by heating or cooling two layers of the separation interface by utilizing a difference in thermal expansion coefficient.

The separation layer is not necessarily provided in the case where the separation can be performed at an interface between the supporting base and the insulating layer.

For example, glass and an organic resin such as polyimide can be used as the supporting base and the insulating layer, respectively. In that case, a separation trigger may be formed by, for example, locally heating part of the organic resin with laser light or the like, or by physically cutting part of or making a hole through the organic resin with a sharp tool, and separation may be performed at an interface between the glass and the organic resin. As the above-described organic resin, a photosensitive material is preferably used because an opening or the like can be easily formed. The above-described laser light preferably has a wavelength region, for example, from visible light to ultraviolet light. For example, light having a wavelength greater than or equal to 200 nm and less than or equal to 400 nm, preferably greater than or equal to 250 nm and less than or equal to 350 nm can be used. In particular, an excimer laser having a wavelength of 308 nm is preferably used because the productivity is increased. Alternatively, a solid-state UV laser (also referred to as a semiconductor UV laser), such as a UV laser having a wavelength of 355 nm which is the third harmonic of an Nd:YAG laser, may be used.

Alternatively, a heat generation layer may be provided between the supporting base and the insulating layer formed of an organic resin, and separation may be performed at an interface between the heat generation layer and the insulating layer by heating the heat generation layer. For the heat generation layer, a material that generates heat when current flows therethrough, a material that generates heat when it absorbs light, a material that generates heat when applied with a magnetic field, and other various materials can be used. For example, a material for the heat generation layer can be selected from a semiconductor, a metal, and an insulator.

In the above-described methods, the insulating layer formed of an organic resin can be used as a substrate after the separation.

The above is the description of the manufacturing method of a flexible display panel.

At least part of the above structure can be implemented in appropriate combination with any of the other structures described in this specification.

«Electronic Device»

Examples of an electronic device of one embodiment of the present invention are described. Examples of the electronic device include a television device (also referred to as a television or a television receiver), a monitor of a computer or the like, a digital camera, a digital video camera, a digital photo frame, a mobile phone (also referred to as a mobile telephone or a mobile phone device), a portable game console, a portable information terminal, an audio reproducing device, and a large-sized game machine such as a pachinko machine. Specific examples of these electronic devices are described below.

Figure 11A:
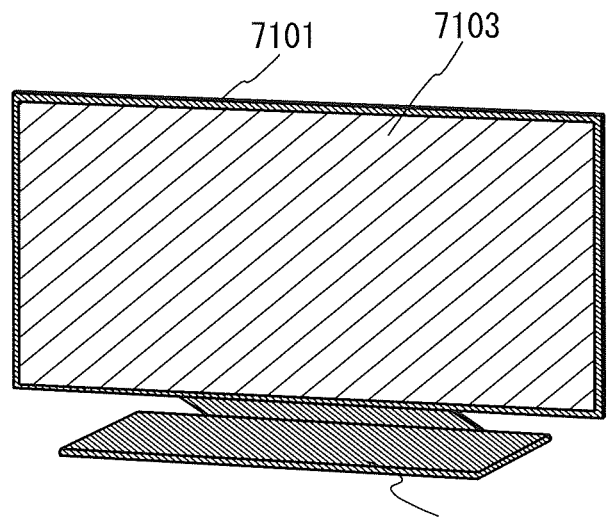
Figure 11A:
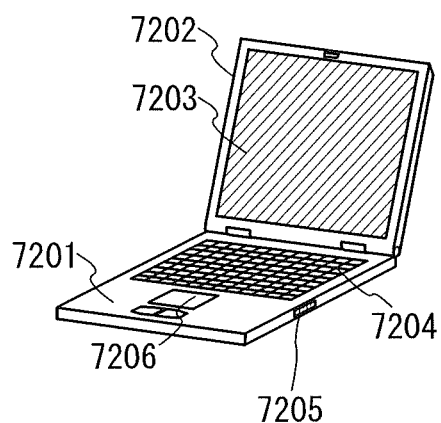
Figure 11A:
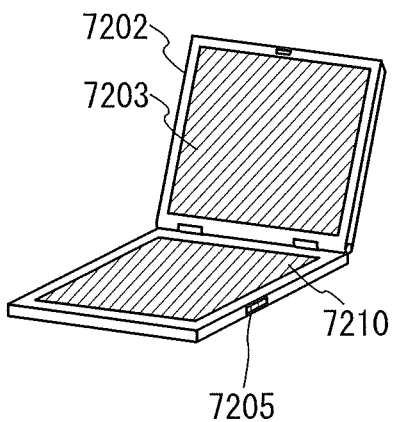

FIG. 11A illustrates an example of a television device. In the television device, a display portion 7103 is incorporated in a housing 7101. In addition, here, the housing 7101 is supported by a stand 7105. Images can be displayed on the display portion 7103, and in the display portion 7103, light-emitting elements are arranged in a matrix.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, a general television broadcast can be received. Moreover, when the display device is connected to a communication network with or without wires via the modem, one-way (from a sender to a receiver) or two-way (between a sender and a receiver or between receivers) information communication can be performed.

FIG. 11B1 illustrates a computer, which includes a main body 7201, a housing 7202, a display portion 7203, a keyboard 7204, an external connection port 7205, a pointing device 7206, and the like. Note that this computer is manufactured by using light-emitting elements arranged in a matrix in the display portion 7203. The computer illustrated in FIG. 11B1 may have a structure illustrated in FIG. 11B2. The computer illustrated in FIG. 11B2 is provided with a second display portion 7210 instead of the keyboard 7204 and the pointing device 7206. The second display portion 7210 is a touch panel, and input can be performed by operation of display for input on the second display portion 7210 with a finger or a dedicated pen. The second display portion 7210 can also display images other than the display for input. The display portion 7203 may also be a touch panel. Connecting the two screens with a hinge can prevent troubles; for example, the screens can be prevented from being cracked or broken while the computer is being stored or carried.

Figure 11C:
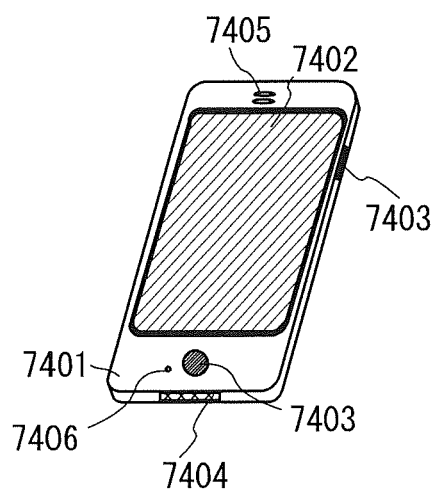
Figure 11D:
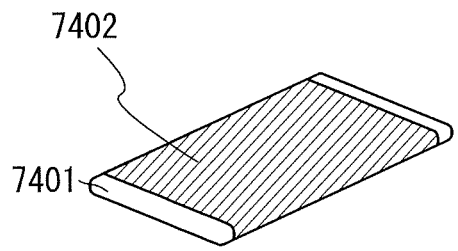

FIGS. 11C and 11D illustrate an example of a portable information terminal. The portable information terminal is provided with a display portion 7402 incorporated in a housing 7401, operation buttons 7403, an external connection port 7404, a speaker 7405, a microphone 7406, and the like. Note that the portable information terminal has the display portion 7402 including light-emitting elements arranged in a matrix.

Information can be input to the portable information terminal illustrated in FIGS. 11C and 11D by touching the display portion 7402 with a finger or the like. In that case, operations such as making a call and creating e-mail can be performed by touching the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or creating e-mail, a text input mode mainly for inputting text is selected for the display portion 7402 so that text displayed on a screen can be input. In that case, it is preferable to display a keyboard or number buttons on almost the entire screen of the display portion 7402.

When a detection device including a sensor such as a gyroscope sensor or an acceleration sensor for sensing inclination is provided inside the portable information terminal, screen display of the display portion 7402 can be automatically changed by determining the orientation of the portable information terminal (whether the portable information terminal is placed horizontally or vertically).

The screen modes are switched by touching the display portion 7402 or operating the operation buttons 7403 of the housing 7401. Alternatively, the screen modes can be switched depending on kinds of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed within a specified period while a signal sensed by an optical sensor in the display portion 7402 is sensed, the screen mode may be controlled so as to be switched from the input mode to the display mode.

The display portion 7402 may also function as an image sensor. For example, an image of a palm print, a fingerprint, or the like is taken by touch on the display portion 7402 with the palm or the finger, whereby personal authentication can be performed. Furthermore, by providing a backlight or a sensing light source which emits near-infrared light in the display portion, an image of a finger vein, a palm vein, or the like can be taken.

Note that in the above electronic devices, any of the structures described in this specification can be combined as appropriate.

The display portion preferably includes a light-emitting element of one embodiment of the present invention. The light-emitting element can have high emission efficiency. In addition, the light-emitting element can be driven with low drive voltage. Thus, the electronic device including the light-emitting element of one embodiment of the present invention can have low power consumption.

Figure 12:
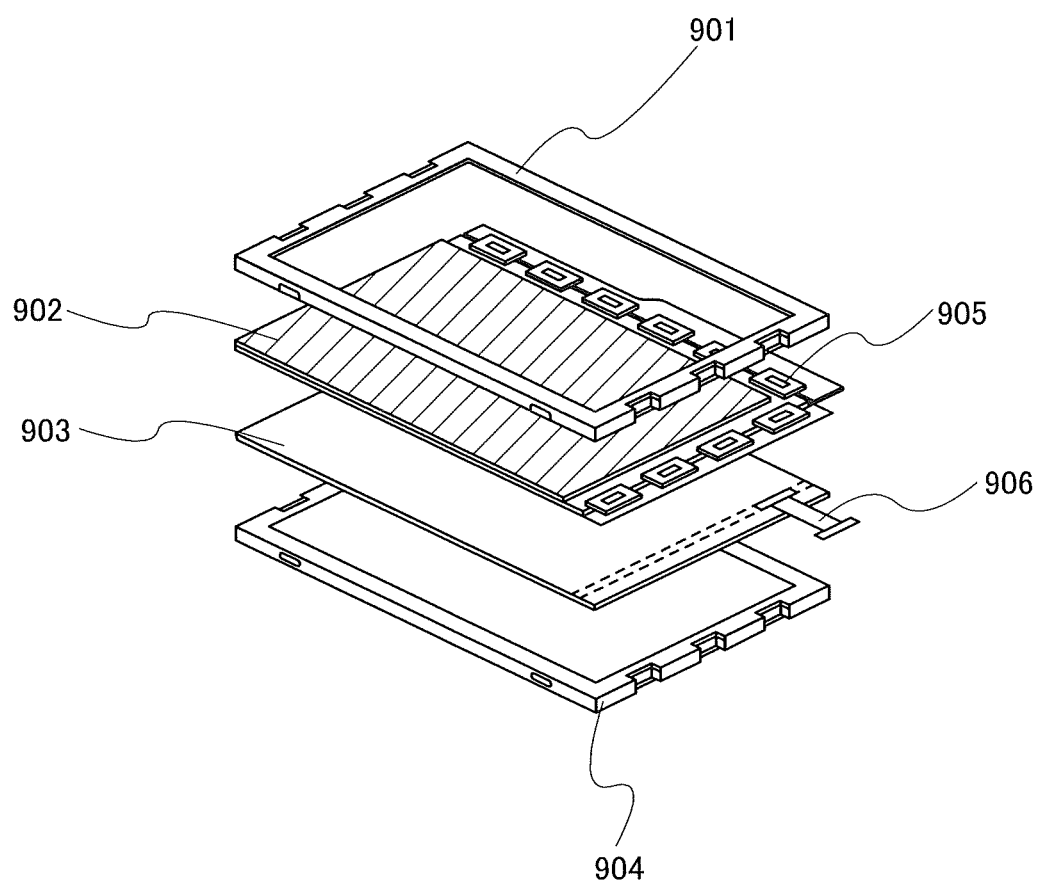
FIG. 12 illustrates a light source device.

FIG. 12 illustrates an example of a liquid crystal display device including the light-emitting element for a backlight. The liquid crystal display device illustrated in FIG. 12 includes a housing 901, a liquid crystal layer 902, a backlight unit 903, and a housing 904. The liquid crystal layer 902 is connected to a driver IC 905. The light-emitting element is used for the backlight unit 903, to which current is supplied through a terminal 906.

As the light-emitting element, a light-emitting element of one embodiment of the present invention is preferably used. By including the light-emitting element, the backlight of the liquid crystal display device can have low power consumption.

Figure 13:
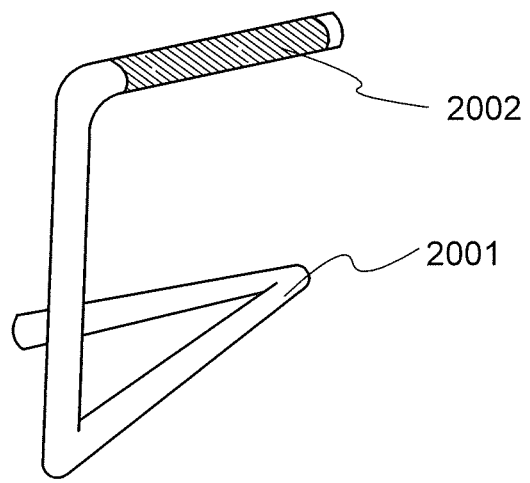
FIG. 13 illustrates a lighting device.

FIG. 13 illustrates an example of a desk lamp of one embodiment of the present invention. The desk lamp illustrated in FIG. 13 includes a housing 2001 and a light source 2002, and a lighting device including a light-emitting element is used as the light source 2002.

Figure 14:
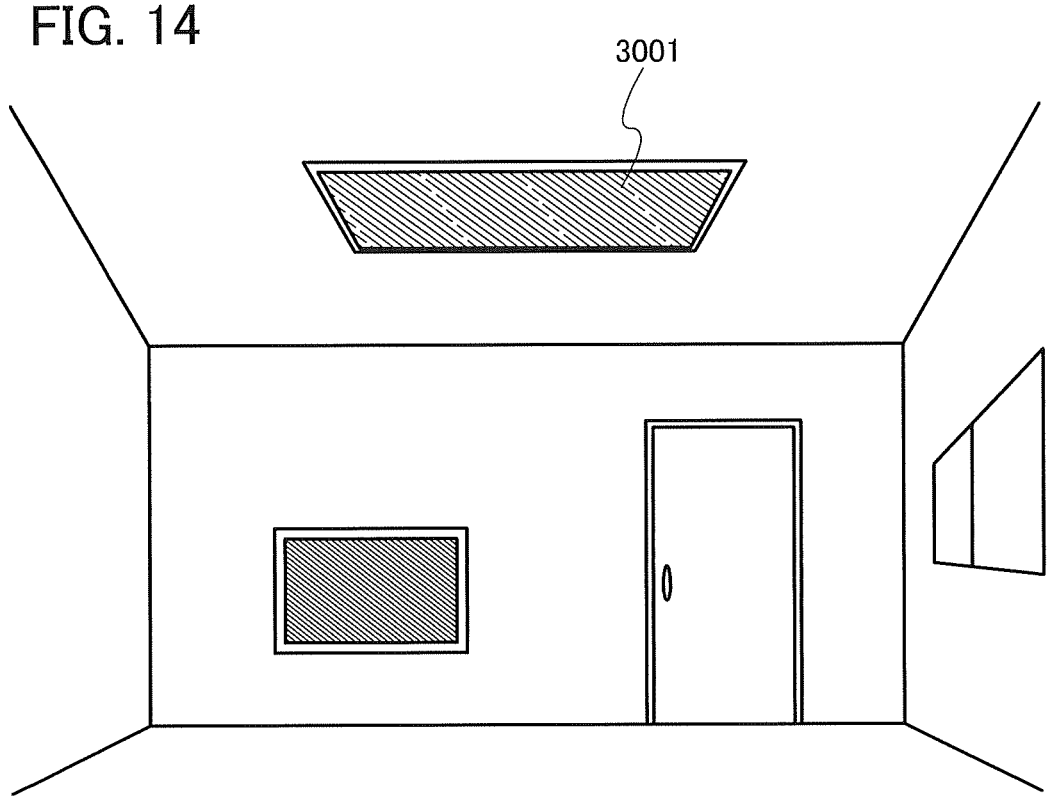
FIG. 14 illustrates a lighting device.

FIG. 14 illustrates an example of an indoor lighting device 3001. The light-emitting element of one embodiment of the present invention is preferably used in the lighting device 3001.

Figure 15:
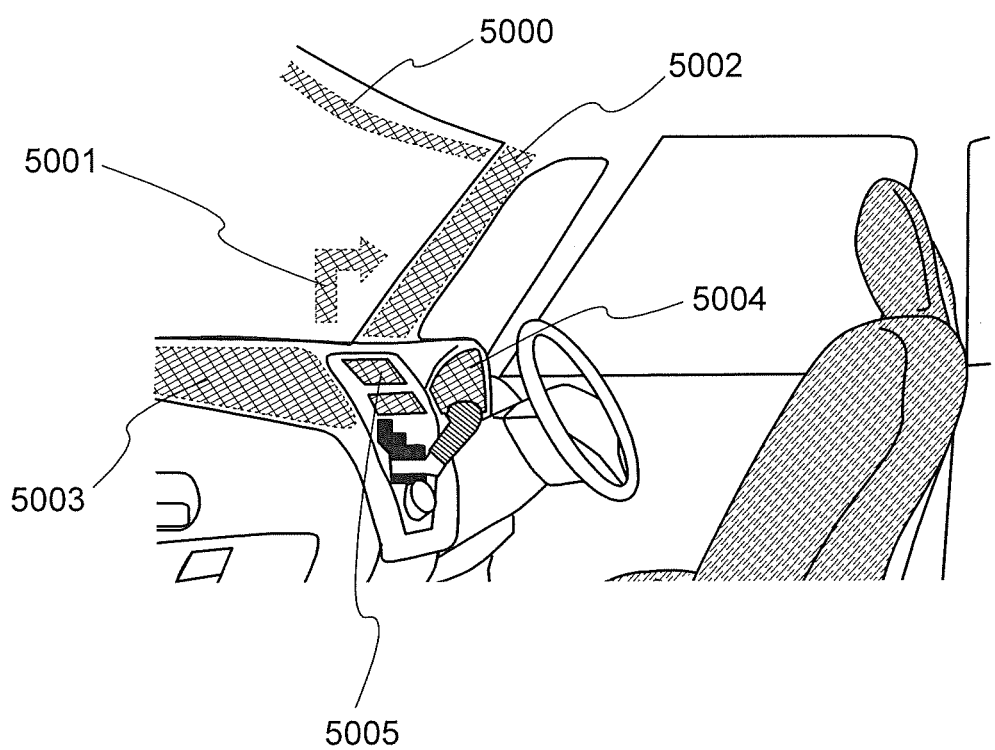
FIG. 15 illustrates car-mounted display devices and lighting devices.

An automobile of one embodiment of the present invention is illustrated in FIG. 15. In the automobile, light-emitting elements are used for a windshield and a dashboard. Display regions 5000 to 5005 are preferably formed by using the light-emitting elements of one embodiment of the present invention. This suppresses power consumption of the display regions 5000 to 5005, showing suitability for use in an automobile.

The display regions 5000 and 5001 are display devices which are provided in the automobile windshield and which include the light-emitting elements. When a first electrode and a second electrode are formed of electrodes having light-transmitting properties in these light-emitting elements, what is called a see-through display device, through which the opposite side can be seen, can be obtained. Such see-through display devices can be provided even in the windshield of the automobile, without hindering the vision. Note that in the case where a transistor for driving the light-emitting element is provided, a transistor having a light-transmitting property, such as an organic transistor using an organic semiconductor material or a transistor using an oxide semiconductor, is preferably used.

The display region 5002 is a display device which is provided in a pillar portion and which includes the light-emitting element. The display region 5002 can compensate for the view hindered by the pillar portion by showing an image taken by an imaging unit provided in the car body. Similarly, the display region 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see makes it possible for the driver to confirm safety easily and comfortably.

The display region 5004 and the display region 5005 can provide a variety of kinds of information such as navigation information, a speedometer, a tachometer, a mileage, a fuel meter, a gearshift indicator, and air-condition setting. The content or layout of the display can be changed freely by a user as appropriate. Note that such information can also be shown by the display regions 5000 to 5003. The display regions 5000 to 5005 can also be used as lighting devices.

Figure 16A:
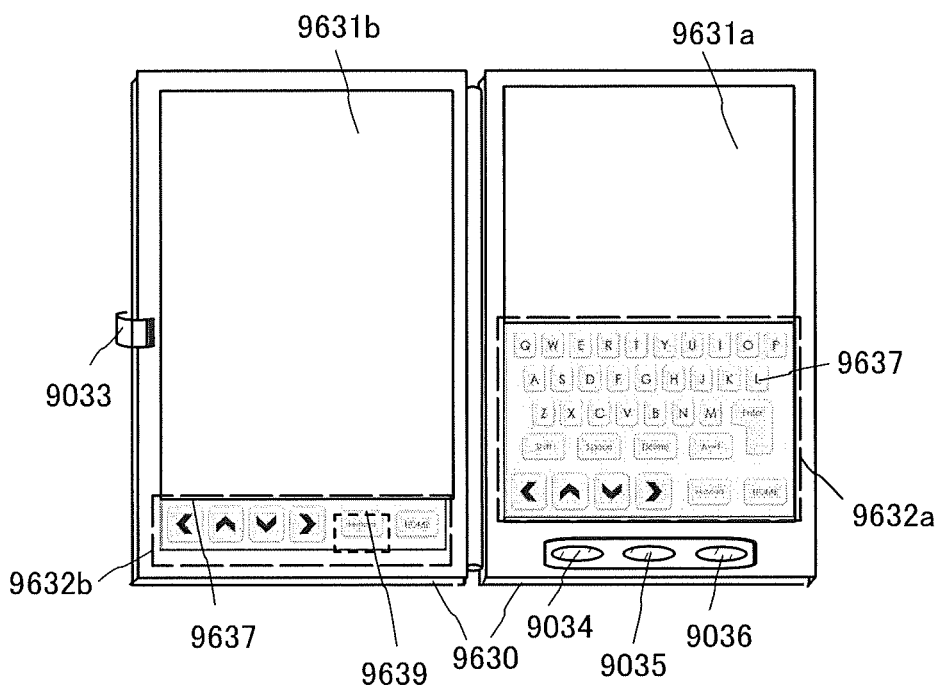
FIGS. 16A to 16C illustrate an electronic device.
Figure 16B:
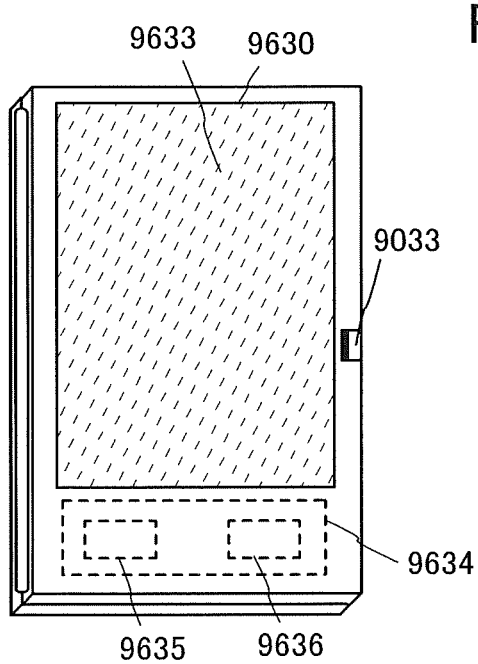

FIGS. 16A and 16B illustrate an example of a foldable tablet terminal. In FIG. 16A, the tablet terminal is opened, and includes a housing 9630, a display portion 9631a, a display portion 9631b, a switch 9034 for switching display modes, a power switch 9035, a switch 9036 for switching to power-saving mode, and a fastener 9033. Note that in the tablet terminal, one or both of the display portion 9631a and the display portion 9631b are formed using a light-emitting device which includes the light-emitting element of one embodiment of the present invention.

Part of the display portion 9631a can be a touch panel region 9632a and data can be input when a displayed operation key 9637 is touched. Although a structure in which a half region in the display portion 9631a has only a display function and the other half region has a touch panel function is illustrated as an example, the structure of the display portion 9631a is not limited thereto. The whole region in the display portion 9631a may have a touch panel function. For example, the display portion 9631a can display keyboard buttons in the whole region to be a touch panel, and the display portion 9631b can be used as a display screen.

Like the display portion 9631a, part of the display portion 9631b can be a touch panel region 9632b. When a switching button 9639 for showing/hiding a keyboard on the touch panel is touched with a finger, a stylus, or the like, the keyboard can be displayed on the display portion 9631b.

Touch input can be performed in the touch panel region 9632a and the touch panel region 9632b at the same time.

The switch 9034 for switching display modes can switch the display between portrait mode, landscape mode, and the like, and between monochrome display and color display, for example. The switch 9036 for switching to power-saving mode can control display luminance to be optimal in accordance with the amount of external light in use of the tablet terminal which is sensed by an optical sensor incorporated in the tablet terminal. Another sensing device including a sensor for sensing inclination, such as a gyroscope sensor or an acceleration sensor, may be incorporated in the tablet terminal, in addition to the optical sensor.

Note that FIG. 16A illustrates an example in which the display portion 9631a and the display portion 9631b have the same display area; however, without limitation thereon, one of the display portions may be different from the other display portion in size and display quality. For example, one display panel may be capable of higher-definition display than the other display panel.

FIG. 16B illustrates the tablet terminal which is folded. The tablet terminal in this embodiment includes the housing 9630, a solar cell 9633, a charge and discharge control circuit 9634, a battery 9635, and a DCDC converter 9636. Note that in FIG. 16B, an example in which the charge and discharge control circuit 9634 includes the battery 9635 and the DCDC converter 9636 is illustrated.

Since the tablet terminal can be folded, the housing 9630 can be closed when the tablet terminal is not used. As a result, the display portion 9631a and the display portion 9631b can be protected; thus, a tablet terminal which has excellent durability and excellent reliability in terms of long-term use can be provided.

In addition, the tablet terminal illustrated in FIGS. 16A and 16B can have a function of displaying a variety of kinds of data (e.g., a still image, a moving image, and a text image), a function of displaying a calendar, a date, the time, or the like on the display portion, a touch-input function of operating or editing the data displayed on the display portion by touch input, a function of controlling processing by a variety of kinds of software (programs), and the like.

The solar cell 9633 provided on a surface of the tablet terminal can supply power to the touch panel, the display portion, a video signal processing portion, or the like. Note that the solar cell 9633 is preferably provided on one or two surfaces of the housing 9630, in which case the battery 9635 can be charged efficiently.

Figure 16C:
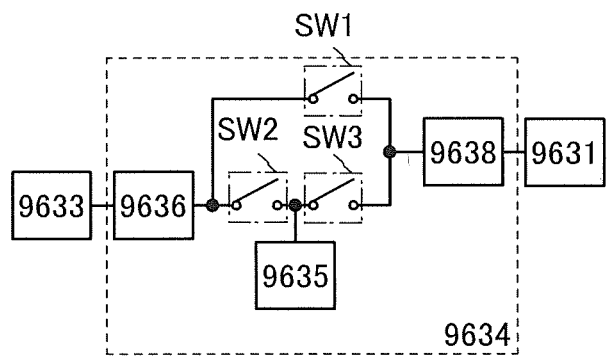

The structure and the operation of the charge and discharge control circuit 9634 illustrated in FIG. 16B are described with reference to a block diagram in FIG. 16C. FIG. 16C illustrates the solar cell 9633, the battery 9635, the DCDC converter 9636, a converter 9638, switches SW1 to SW3, and the display portion 9631. The battery 9635, the DCDC converter 9636, the converter 9638, and the switches SW1 to SW3 correspond to the charge and discharge control circuit 9634 illustrated in FIG. 16B.

First, an example of the operation in the case where power is generated by the solar cell 9633 using external light is described. The voltage of power generated by the solar cell is raised or lowered by the DCDC converter 9636 so that the power has a voltage for charging the battery 9635. Then, when power supplied from the battery 9635 charged by the solar cell 9633 is used for the operation of the display portion 9631, the switch SW1 is turned on and the voltage of the power is raised or lowered by the converter 9638 so as to be voltage needed for the display portion 9631. In addition, when display on the display portion 9631 is not performed, the switch SW1 is turned off and the switch SW2 is turned on so that charge of the battery 9635 may be performed.

Although the solar cell 9633 is described as an example of a power generation means, the power generation means is not particularly limited, and the battery 9635 may be charged by another power generation means such as a piezoelectric element or a thermoelectric conversion element (Peltier element). The battery 9635 may be charged by a non-contact power transmission module capable of performing charging by transmitting and receiving power wirelessly (without contact), or any of the other charge means used in combination, and the power generation means is not necessarily provided.

One embodiment of the present invention is not limited to the tablet terminal having the shape illustrated in FIGS. 16A to 16C as long as the display portion 9631 is included.

Figure 17A:
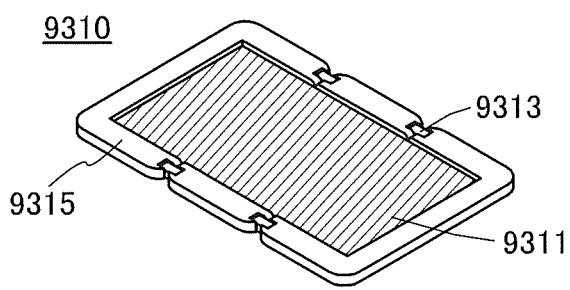
FIGS. 17A to 17C illustrate an electronic device.
Figure 17B:
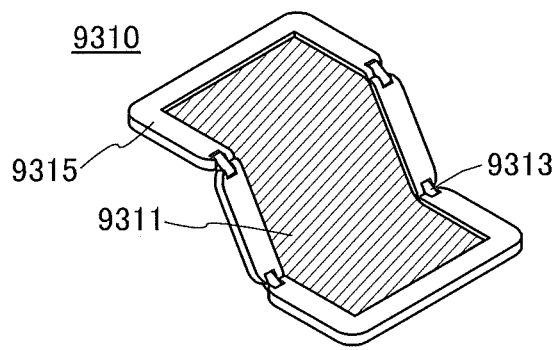
Figure 17C:
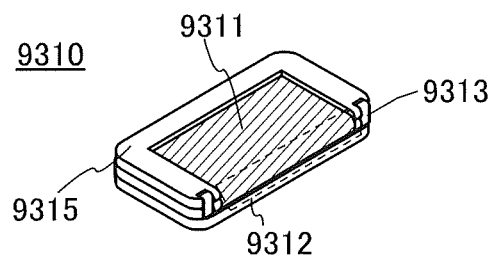

FIGS. 17A to 17C illustrate a foldable portable information terminal 9310. FIG. 17A illustrates the portable information terminal 9310 which is opened. FIG. 17B illustrates the portable information terminal 9310 which is being opened or being folded. FIG. 17C illustrates the portable information terminal 9310 which is folded. The portable information terminal 9310 is highly portable when folded. The portable information terminal 9310 is highly browsable when opened because of a seamless large display region.

A display panel 9311 is supported by three housings 9315 joined together by hinges 9313. Note that the display panel 9311 may be a touch panel (an input/output device) including a touch sensor (an input device). By bending the display panel 9311 at a connection portion between two housings 9315 with the use of the hinges 9313, the portable information terminal 9310 can be reversibly changed in shape from an opened state to a folded state. A light-emitting device of one embodiment of the present invention can be used for the display panel 9311. A display region 9312 in the display panel 9311 is a display region that is positioned at a side surface of the portable information terminal 9310 that is folded. On the display region 9312, information icons, file shortcuts of frequently used applications or programs, and the like can be displayed, and confirmation of information and start of application can be smoothly performed.

EXAMPLE 1

In this example, a light-emitting element 1 that is the light-emitting element of one embodiment of the present invention described in Embodiment is described. Structural formulae of organic compounds used for the light-emitting element 1 are shown below.

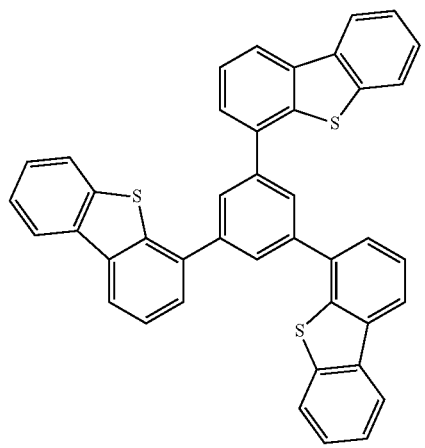

(i) DBT3P-II

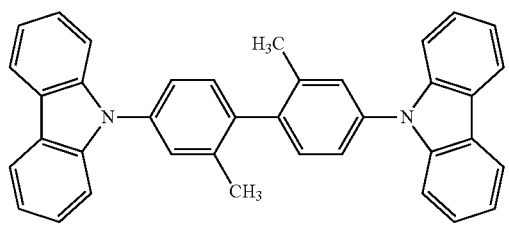

(ii) dmCBP

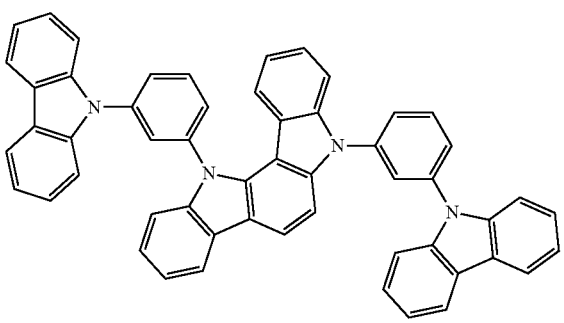

(iii) mCzPICz

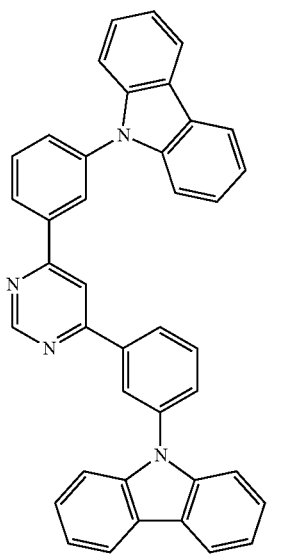

(iv) 4,6mCzP2Pm

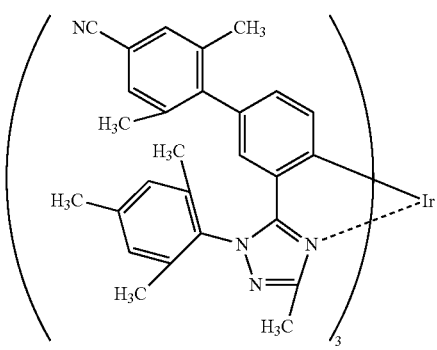

(v) Ir(MdmCN5btz1-tmp)₃

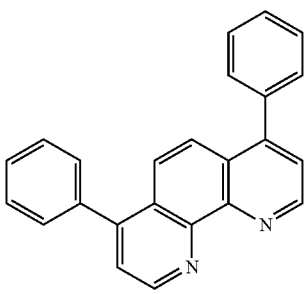

(vi) BPhen (Fabrication Method of Light-Emitting Element 1)

First, indium tin oxide containing silicon oxide (ITSO) was deposited over a glass substrate by a sputtering method to form the first electrode 101. The thickness of the first electrode 101 was set to 70 nm and the area of the electrode was set to 4 mm² (2 mm×2 mm).

Next, in pretreatment for forming the light-emitting element over the substrate, a surface of the substrate was washed with water and baked at 200° C. for one hour, and then UV ozone treatment was performed for 370 seconds.

After that, the substrate was transferred into a vacuum evaporation apparatus whose pressure was reduced to approximately $10^{-4}$ Pa, vacuum baking at 170° C. for 30 minutes was performed in a heating chamber in the vacuum evaporation apparatus, and then the substrate was cooled down for approximately 30 minutes.

Then, the substrate over which the first electrode 101 was formed was fixed to a substrate holder provided in the vacuum evaporation apparatus so that the surface on which the first electrode 101 was formed faced downward. After that, on the first electrode 101, 1,3,5-tri-(4-dibenzothiophenyl)-benzene (abbreviation: DBT3P-II) represented by Structural formula (i) and molybdenum(VI) oxide were deposited by co-evaporation to a thickness of 20 nm at a weight ratio of 2:1 (=DBT3P-II: molybdenum oxide) by an evaporation method using resistance heating, so that the hole-injection layer 111 was formed.

Next, 4,4'-bis(9-carbazole)-2,2'-dimethylbiphenyl (abbreviation: dmCBP) represented by Structural formula (ii) was deposited by evaporation to a thickness of 20 nm over the hole-injection layer 111 to form the hole-transport layer 112.

Next, 5,12-bis[3-(9H-carbazol-9-yl)phenyl]-5,12-dihydro-indolo[3,2-α]carbazole (abbreviation: mCzP2Icz) represented by Structural formula (iii), 9,9'-(pyrimidine-4,6-diyldi-3,1-phenylene)bis(9H-carbazole) (abbreviation: 4,6mCzP2Pm) represented by Structural formula (iv), and tris{4'-cyano-2',6'-dimethyl-3-[methyl-1-(2,4,6-trimethylphenyl)-1H-1,2,4-triazol-5-yl-κN⁴]-1,1'-biphenyl-4-yl-κC}iridium(III) (abbreviation: [Ir(MdmCN5btz1-tmp)₃]) were deposited by co-evaporation to a thickness of 20 nm at a weight ratio of 0.4:0.6:0.125(=mCzP2Icz:4,6mCzP2Pm:[Ir(MdmCN5btz1-tmp)₃]), so that the light-emitting layer 113 was formed.

Then, 4,6mCzP2Pm was deposited by evaporation to a thickness of 30 nm, and bathophenanthroline (abbreviation: BPhen) represented by Structural formula (vi) was deposited by evaporation to a thickness of 15 nm over the light-emitting layer 113 to form the electron-transport layer 114.

After the formation of the electron-transport layer 114, lithium fluoride (LiF) was deposited by evaporation to a thickness of 1 nm to form the electron-injection layer 115. Then, aluminum was deposited by evaporation to a thickness of 200 nm to form the second electrode 102. Through the above-described steps, the light-emitting element 1 of this example was fabricated.

The element structure of the light-emitting element 1 is shown in the following table.

TABLE 4

| Hole-injection Layer | Hole-transport Layer | Light-emitting Layer | Electron-transport Layer | | Electron-injection Layer |
|---|---|---|---|---|---|
| DBT3P-II: MoOx (2:1) | dmCBP | mCzPICz: 4,6mCzP2Pm: Ir(MdmCN5btz1-tmp)₃ (0.4:0.6:0.125) | 4,6mCzP2Pm | BPhen | LiF |
| 20 nm | 20 nm | 20 nm | 30 nm | 15 nm | 1 nm |

The light-emitting element 1 was sealed using a glass substrate in a glove box containing a nitrogen atmosphere so as not to be exposed to the air (specifically, a sealing material was applied to surround the element, UV treatment and heat treatment at 80° C. for 1 hour were performed at the time of sealing). Then, initial characteristics of the light-emitting element were measured. The measurement was carried out at room temperature (under an atmosphere where a temperature was maintained at 25° C.).

Figure 20:
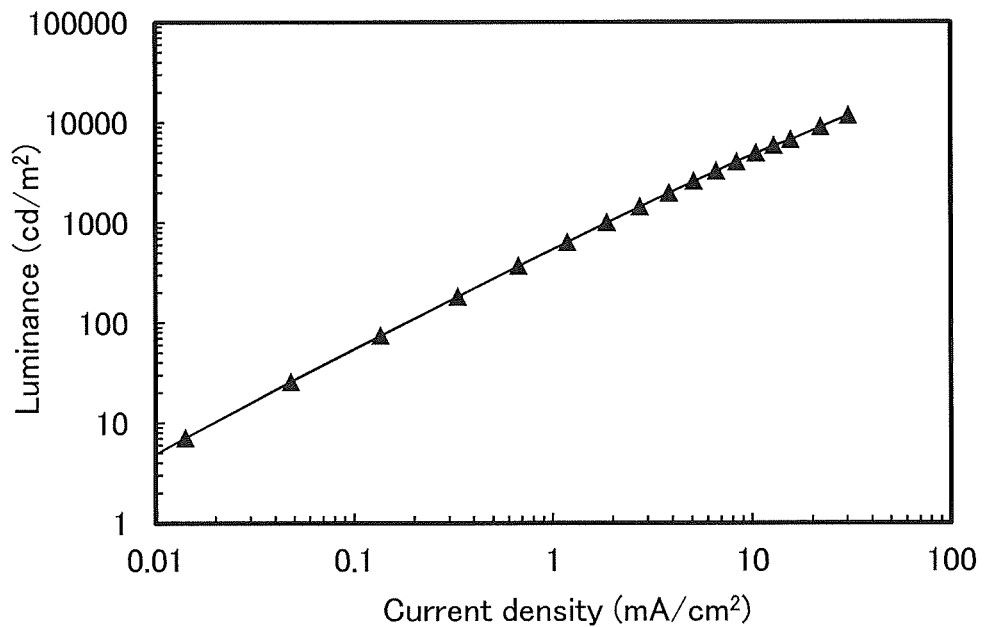
FIG. 20 shows the luminance-current density characteristics of a light-emitting element 1.
Figure 21:
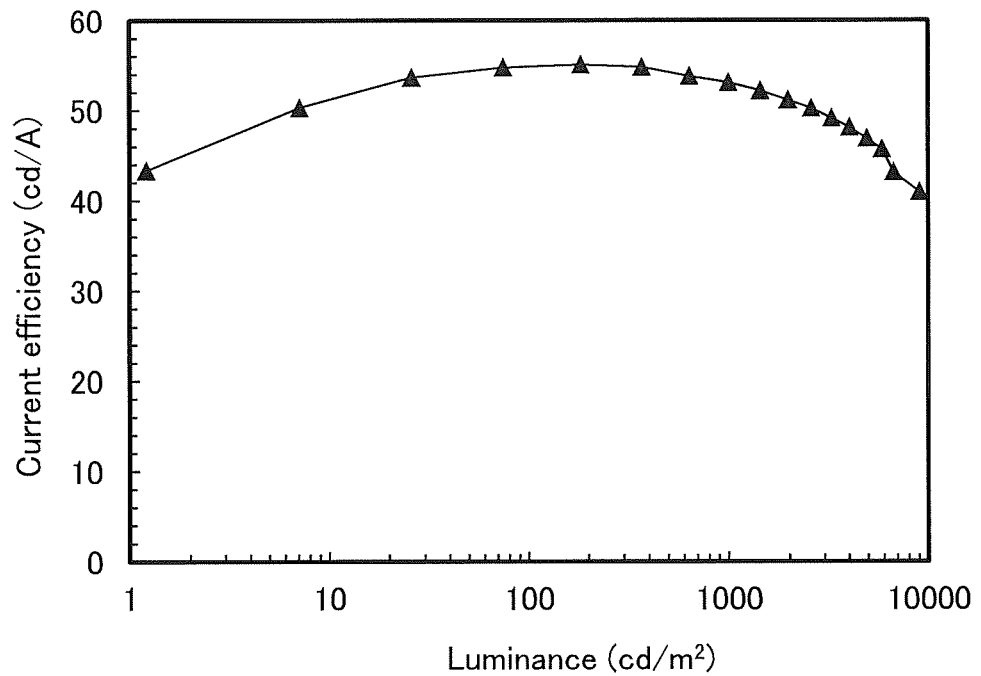
FIG. 21 shows the current efficiency-luminance characteristics of the light-emitting element 1.
Figure 22:
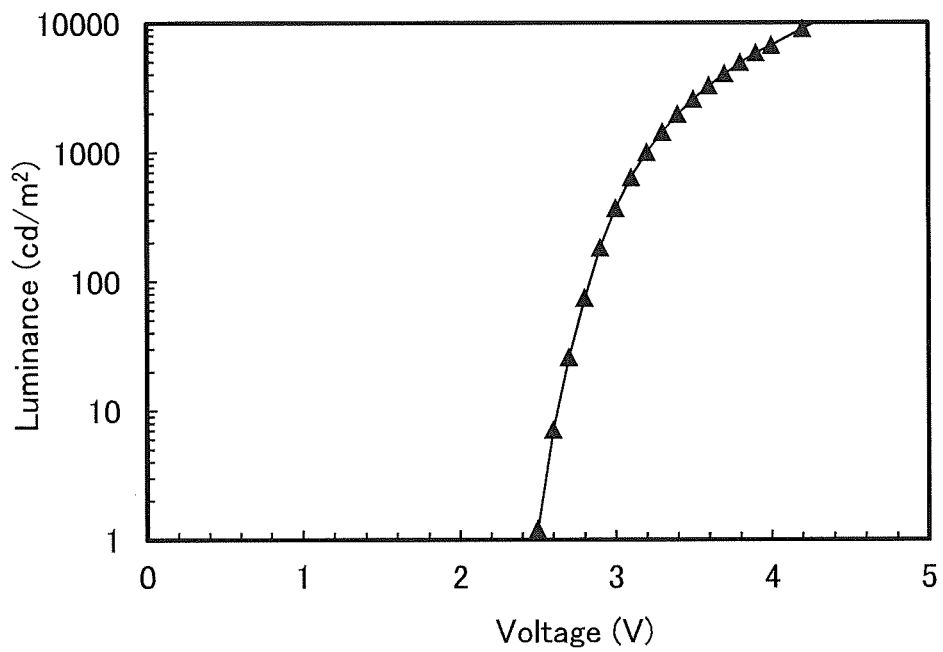
FIG. 22 shows the luminance-voltage characteristics of the light-emitting element 1.
Figure 23:
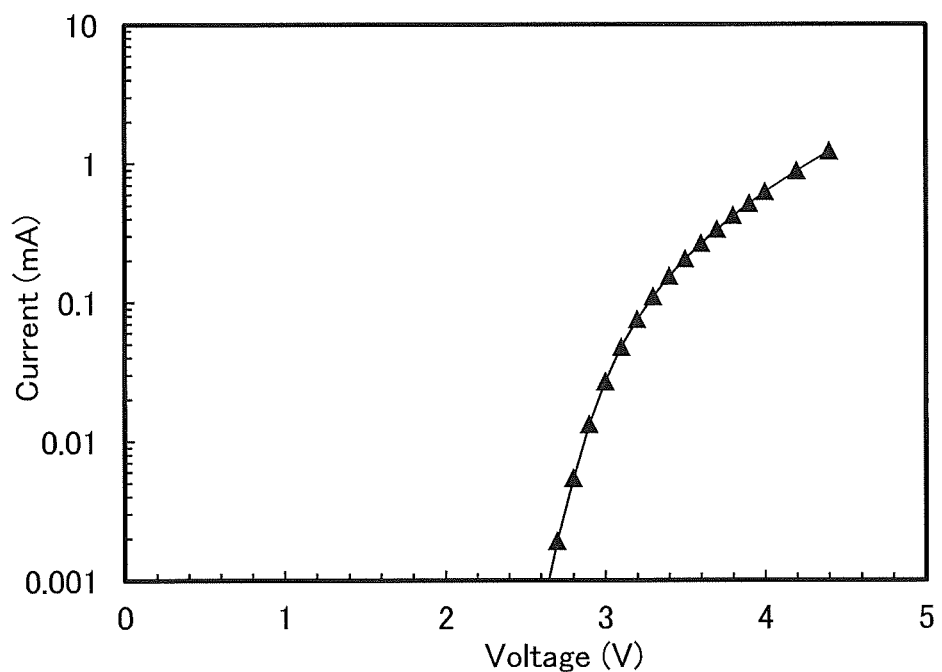
FIG. 23 shows the current-voltage characteristics of the light-emitting element 1.
Figure 24:
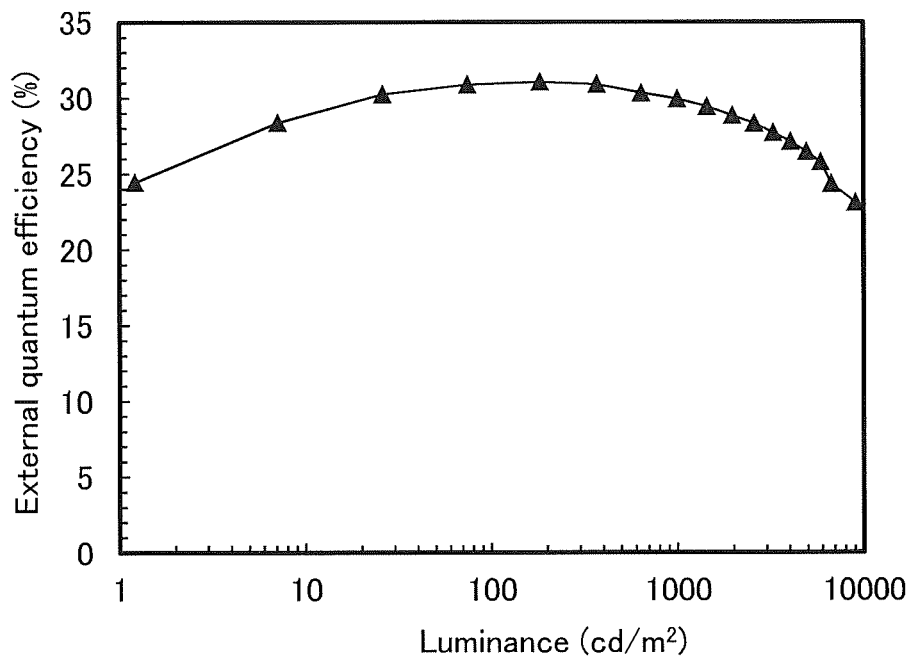
FIG. 24 shows the external quantum efficiency-luminance characteristics of the light-emitting element 1.
Figure 25:
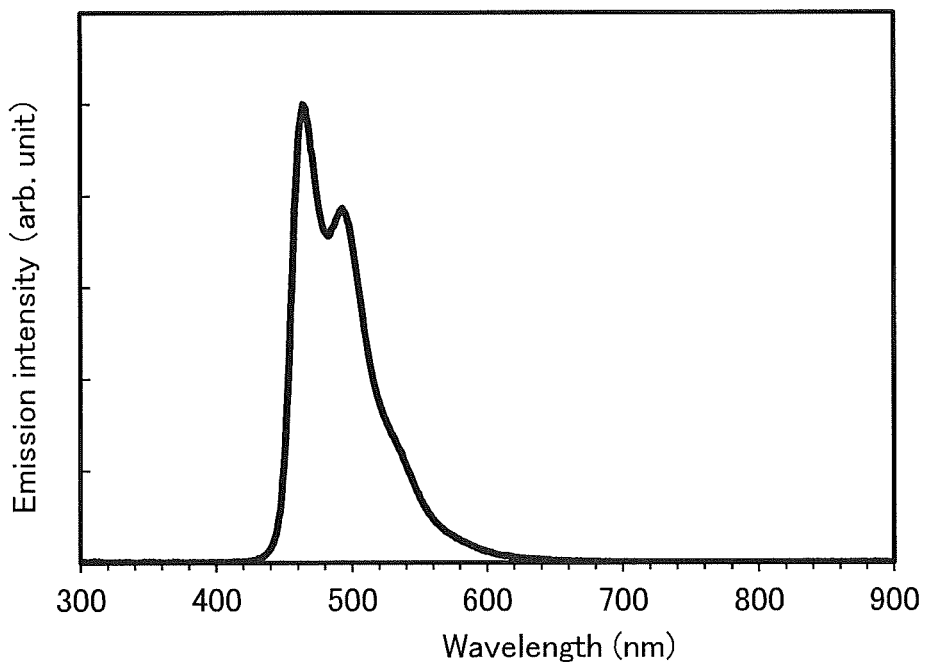
FIG. 25 shows the emission spectrum of the light-emitting element 1.

FIG. 20 shows the luminance-current density characteristics of the light-emitting element 1. FIG. 21 shows the current efficiency-luminance characteristics of the light-emitting element 1. FIG. 22 shows the luminance-voltage characteristics of the light-emitting element 1. FIG. 23 shows the current-voltage characteristics of the light-emitting element 1. FIG. 24 shows the external quantum efficiency-luminance characteristics of the light-emitting element 1. FIG. 25 shows the emission spectrum of the light-emitting element 1.

TABLE 5

| Voltage (V) | Current (mA) | Current Density (mA/cm$^2$) | Current Efficiency (cd/A) | External Quantum Efficiency (%) |
|---|---|---|---|---|
| 3.2 | 0.075 | 1.9 | 53.1 | 29.9 |

The results shown in FIG. 20, FIG. 21, FIG. 22, FIG. 23, FIG. 24, FIG. 25, and Table 5 indicate that the light-emitting element 1 exhibits extremely high efficiency, i.e., the external quantum efficiency at 1000 cd/m$^2$ is 29.9% and the maximum external quantum efficiency is 31.1%.

Note that the parameter of planarity (A×B/C$^2$) of [Ir(MdmCN5btz1-tmp)$_3$] was calculated to be 3.4. In this manner, the light-emitting element formed using the tris iridium complex with high parameter of planarity can exhibit extremely high efficiency.

EXAMPLE 2

In this example, a light-emitting element 2 that is one embodiment of the present invention described in Embodiment and a comparative light-emitting element 2 are described. Structural formulae of organic compounds used in the light-emitting element 2 and the comparative light-emitting element 2 are shown below.

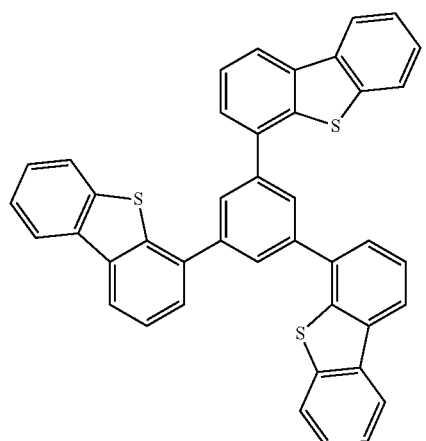

(i) DBT3P-II

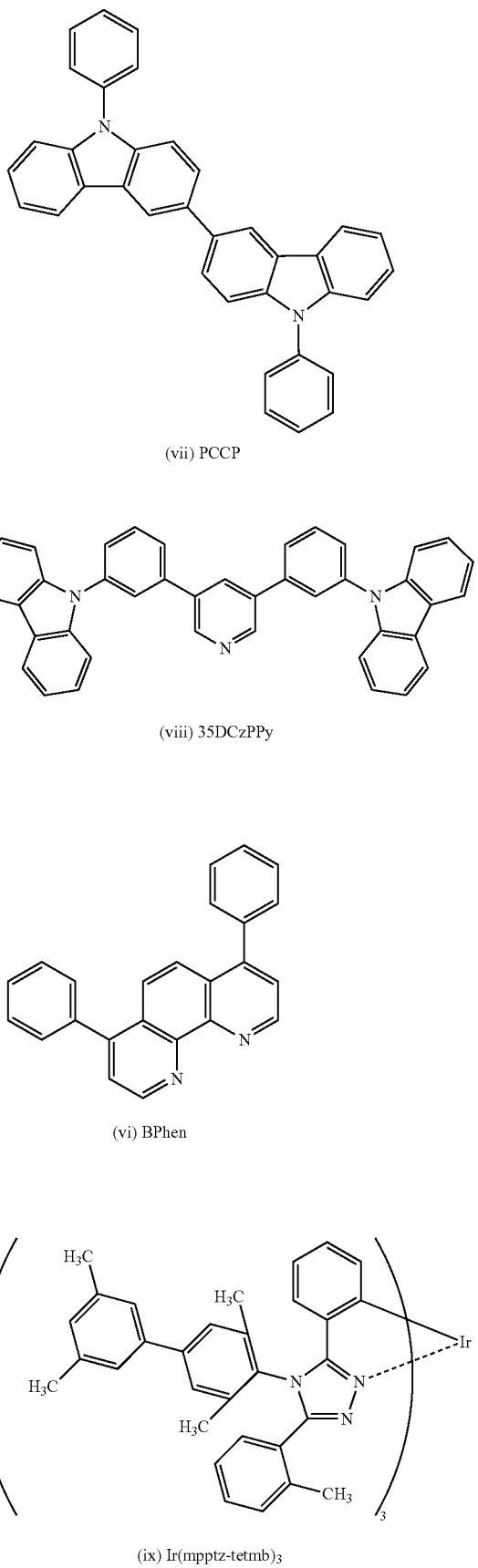

(vii) PCCP (viii) 35DCzPPy (vi) BPhen (ix) Ir(mpptz-tetmb)$_3$

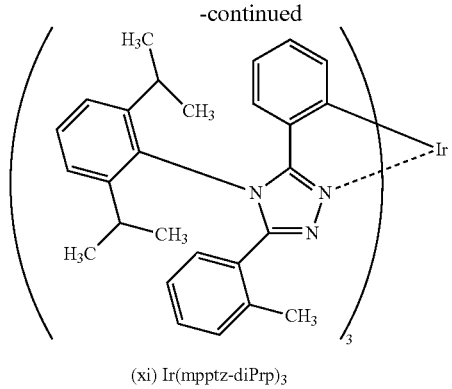

(xi) Ir(mpptz-diPrp)₃

(Fabrication Method of Light-Emitting Element 2)

First, indium tin oxide containing silicon oxide (ITSO) was deposited over a glass substrate by a sputtering method to form the first electrode 101. The thickness of the first electrode 101 was set to 110 nm and the area of the electrode was set to 4 mm² (2 mm×2 mm).

Next, in pretreatment for forming the light-emitting element over the substrate, a surface of the substrate was washed with water and baked at 200° C. for 1 hour, and then UV ozone treatment was performed for 370 seconds.

After that, the substrate was transferred into a vacuum evaporation apparatus whose pressure was reduced to approximately $10^{-4}$ Pa, vacuum baking at 170° C. for 30 minutes was performed in a heating chamber in the vacuum evaporation apparatus, and then the substrate was cooled down for approximately 30 minutes.

Then, the substrate over which the first electrode 101 was formed was fixed to a substrate holder provided in the vacuum evaporation apparatus so that the surface on which the first electrode 101 was formed faced downward. After that, on the first electrode 101, 1,3,5-tri-(4-dibenzothiophenyl)-benzene (abbreviation: DBT3P-II) represented by Structural formula (i) and molybdenum(VI) oxide were deposited by co-evaporation to a thickness of 70 nm at a weight ratio of 2:1 (=DBT3P-II: molybdenum oxide) by an evaporation method using resistance heating, so that the hole-injection layer 111 was formed.

Next, 3,3'-bis(9-phenyl-9H-carbazole) (abbreviation: PCCP) represented by Structural formula (vii) was deposited by evaporation to a thickness of 20 nm over the hole-injection layer 111 to form the hole-transport layer 112.

Then, PCCP, 3,5-bis[3-(9H-carbazol-9-yl)phenyl]pyridine (abbreviation: 35DCzPPy) represented by Structural Formula (viii), and tris{2-[5-(2-methylphenyl)-4-(3,3',5,5'-tetramethyl-1,1'-biphenyl-4-yl)-4H-1,2,4-triazol-3-yl-κN²]phenyl-κC}iridium(III) (abbreviation: [Ir(mpptz-tetmb)₃]) represented by Structural Formula (ix) were deposited by co-evaporation to a thickness of 30 nm at a weight ratio of 1:0.3:0.06 (=PCCP:35DCzPPy:[Ir(mpptz-tetmb)₃]), and then 35DCzPPy and [Ir(mpptz-tetmb)₃] were deposited by co-evaporation to a thickness of 10 nm at a weight ratio of 1:0.06 (=35DCzPPy:[Ir(mpptz-tetmb)₃]), so that the light-emitting layer 113 was formed.

Then, 35DCzPPy was deposited by evaporation to a thickness of 10 nm, and bathophenanthroline (abbreviation: BPhen) represented by Structural formula (vi) was deposited by evaporation to a thickness of 15 nm over the light-emitting layer 113 to form the electron-transport layer 114.

After the formation of the electron-transport layer 114, lithium fluoride (LiF) was deposited by evaporation to a thickness of 1 mn to form the electron-injection layer 115. Then, aluminum was deposited by evaporation to a thickness of 200 nm to form the second electrode 102. Through the above-described steps, the light-emitting element 2 of this example was fabricated.

(Fabrication Method of Comparative Light-Emitting Element 2)

The comparative light-emitting element 2 was fabricated in the same manner as the light-emitting element 2 except that tris{2-[5-(2-methylphenyl)-4-(2,6-diisopropylphenyl)-4H-1,2,4-triazol-3-yl-κN²]phenyl-κC}iridium(III) (abbreviation: [Ir(mpptz-diPrp)₃]) represented by Structural Formula (xi) was used instead of [Ir(mpptz-tetmb)₃] of the light-emitting element 2.

The element structures of the light-emitting element 2 and the comparative light-emitting element 2 are shown in the following table.

TABLE 6

| Light-emitting Element 2 | | | | | | |
|---|---|---|---|---|---|---|
| | | Light-emitting Layer | | | | |
| Hole-injection Layer | Hole-transport Layer | First Light-emitting Layer | Second Light-emitting Layer | Electron-transport Layer | | Electron-injection Layer |
| DBT3P-II: MoOx (2:1) | PCCP | PCCP: 35DCzPPy: Ir(mpptz-tetmb)₃ (1:0.3:0.06) | 35DCzPPy: Ir(mpptz-tetmb)₃ (1:0.06) | 35DCzPPy | BPhen | LiF |
| 70 nm | 20 nm | 30 nm | 10 nm | 10 nm | 15 nm | 1 nm |

TABLE 7

| Comparative Light-emitting Element 2 | | | | | | |
|---|---|---|---|---|---|---|
| | | Light-emitting Layer | | | | |
| Hole-injection Layer | Hole-transport Layer | First Light-emitting Layer | Second Light-emitting Layer | Electron-transport Layer | | Electron-injection Layer |
| DBT3P-II: MoOx | PCCP | PCCP: 35DCzPPy: | 35DCzPPy: Ir(mpptz- | 35DCzPPy | BPhen | LiF |

TABLE 7-continued

Comparative Light-emitting Element 2

| Hole-injection Layer | Hole-transport Layer | Light-emitting Layer | | Electron-transport Layer | Electron-injection Layer |
| --- | --- | --- | --- | --- | --- |
| | | First Light-emitting Layer | Second Light-emitting Layer | | |
| (2:1) | | Ir(mpptz-diPrp)$_3$ (1:0.3:0.06) | diPrp$_3$ (1:0.06) | | |
| 70 nm | 20 nm | 30 nm | 10 nm | 10 nm | 15 nm | 1 nm |

Each of the light-emitting element 2 and the comparative light-emitting element 2 was sealed using a glass substrate in a glove box containing a nitrogen atmosphere so as not to be exposed to the air (specifically, a sealing material was applied to surround the element, UV treatment and heat treatment at 80° C. for 1 hour were performed at the time of sealing). Then, initial characteristics of these light-emitting elements were measured. The measurement was carried out at room temperature (under an atmosphere where a temperature was maintained at 25° C.).

Figure 26:
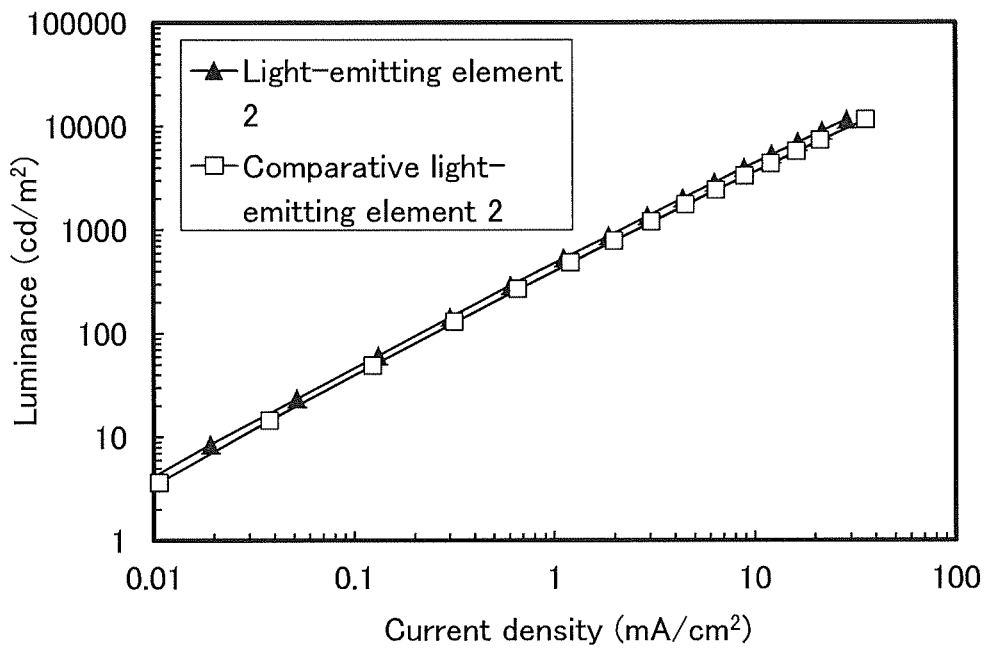
FIG. 26 shows the luminance-current density characteristics of a light-emitting element 2 and a comparative light-emitting element 2.
Figure 27:
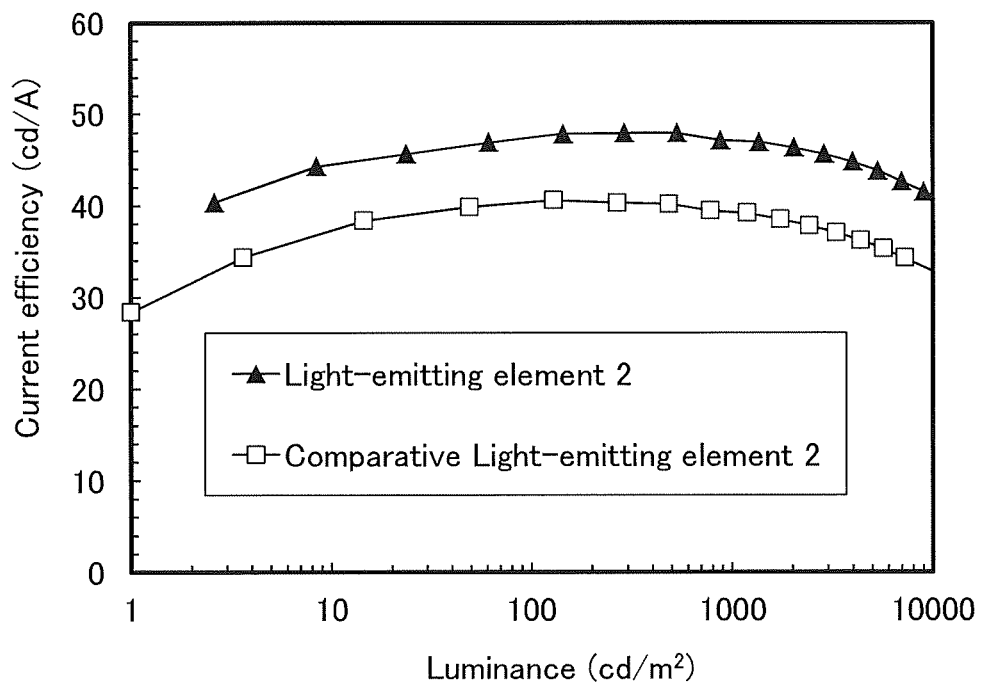
FIG. 27 shows the current efficiency-luminance characteristics of the light-emitting element 2 and the comparative light-emitting element 2.
Figure 28:
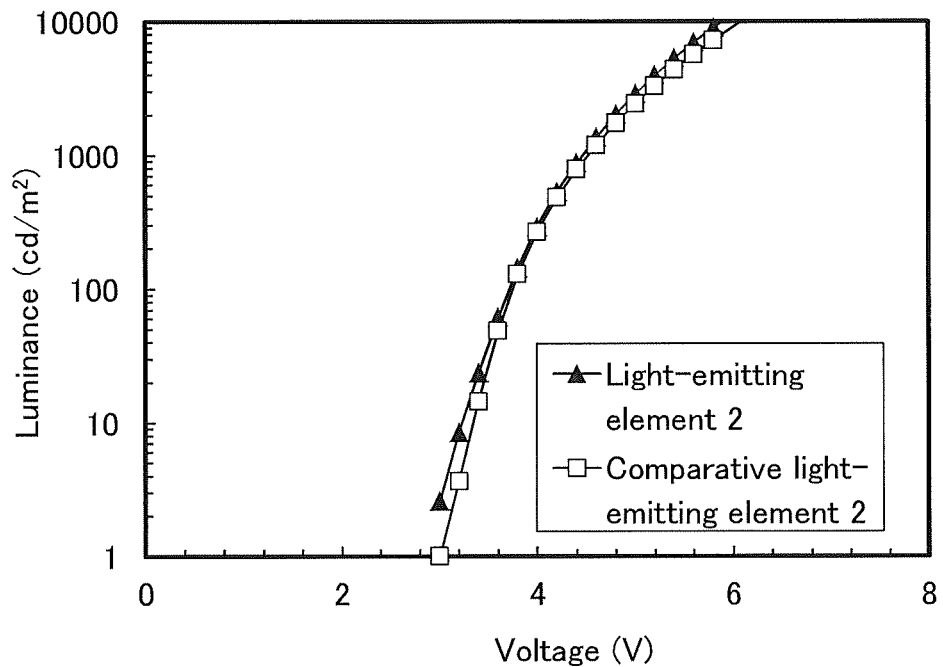
FIG. 28 shows the luminance-voltage characteristics of the light-emitting element 2 and the comparative light-emitting element 2.
Figure 29:
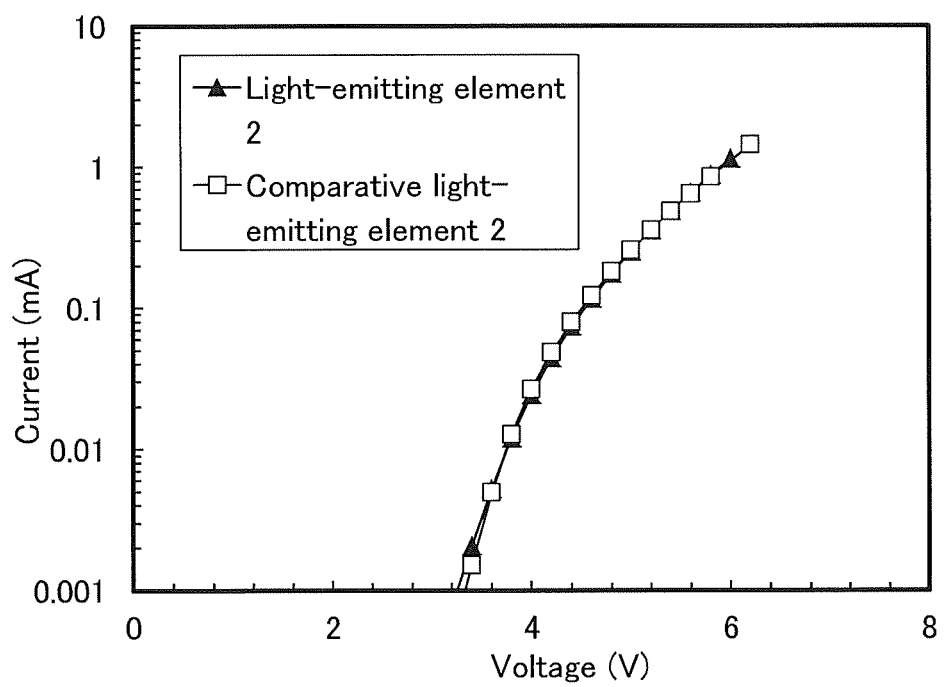
FIG. 29 shows the current-voltage characteristics of the light-emitting element 2 and the comparative light-emitting element 2.
Figure 30:
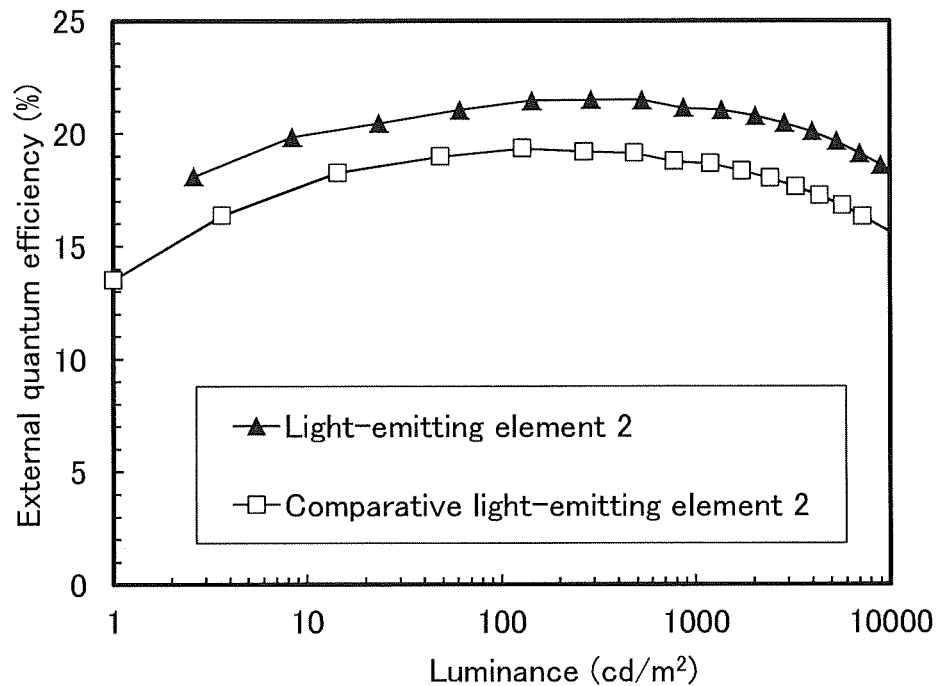
FIG. 30 shows the external quantum efficiency-luminance characteristics of the light-emitting element 2 and the comparative light-emitting element 2.
Figure 31:
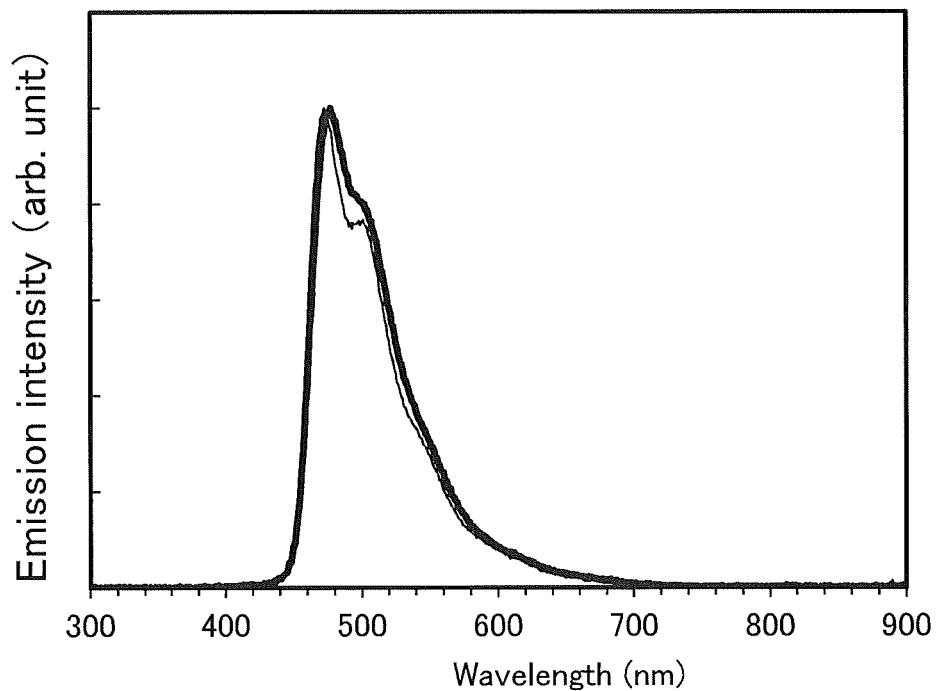
FIG. 31 shows the emission spectra of the light-emitting element 2 and the comparative light-emitting element 2.

FIG. 26 shows the luminance-current density characteristics of the light-emitting element 2 and the comparative light-emitting element 2. FIG. 27 shows the current efficiency-luminance characteristics of the light-emitting element 2 and the comparative light-emitting element 2. FIG. 28 shows the luminance-voltage characteristics of the light-emitting element 2 and the comparative light-emitting element 2. FIG. 29 shows the current-voltage characteristics of the light-emitting element 2 and the comparative light-emitting element 2. FIG. 30 shows the external quantum efficiency-luminance characteristics of the light-emitting element 2 and the comparative light-emitting element 2. FIG. 31 shows the emission spectra of the light-emitting element 2 and the comparative light-emitting element 2.

TABLE 8

| | Voltage (V) | Current (mA) | Current Density (mA/cm$^2$) | Current Efficiency (cd/A) | External Quantum Efficiency (%) |
| --- | --- | --- | --- | --- | --- |
| Light-emitting Element 2 | 4.4 | 0.074 | 1.9 | 47.1 | 21.1 |
| Comparative Light-emitting Element 2 | 4.6 | 0.122 | 3.1 | 39.2 | 18.7 |

According to FIG. 26, FIG. 27, FIG. 28, FIG. 29, FIG. 30, FIG. 31, and Table 8, the external quantum efficiency at 1000 cd/m$^2$ and the maximum external quantum efficiency of the light-emitting element 2 are 21.1% and 21.5%, respectively; and the external quantum efficiency at 1000 cd/m$^2$ and the maximum external quantum efficiency of the comparative light-emitting element 2 are 18.7% and 19.3%, respectively.

Note that the parameter of planarity (A×B/C$^2$) of [Ir(mpptz-tetmb)$_3$] used in the light-emitting element 2 was calculated to be 5.3, and the parameter of planarity (A×B/C$^2$) of [Ir(mpptz-diPrp)$_3$] used in the comparative light-emitting element 2 was calculated to be 2.4. As shown in Table 2 described in Embodiment, [Ir(mpptz-diPrp)$_3$] is an iridium complex with which the light-emitting element can achieve an external quantum efficiency of 27.7%.

As shown in the above table, the comparative light-emitting element 2 employing [Ir(mpptz-diPrp)$_3$] has an external quantum efficiency of 18.7%, whereas the light-emitting element 2, which has the same structure as the comparative light-emitting element 2 except that the dopant was [Ir(mpptz-tetmb)$_3$], has an external quantum efficiency of 21.1%; in other words, the external quantum efficiency of the light-emitting element 2 is higher than that of the comparative light-emitting element 2 by approximately 2.4%.

Note that the thicknesses of the first electrode and the hole-injection layer of each of the light-emitting element 2 and the comparative light-emitting element 2 are 110 nm and 70 nm, respectively, and thus the optical distances thereof significantly differ from those of the other light-emitting elements of this example. For this reason, the light-emitting element 2 and the comparative light-emitting element 2 have lower external quantum efficiency. Therefore, when [Ir(mpptz-tetmb)$_3$] is used instead of [Ir(mpptz-diPrp)$_3$] in a light-emitting element which has the same structure as the light-emitting element that employs [Ir(mpptz-diPrp)$_3$] and achieves an external quantum efficiency of 27.7%, an improvement similar to that described in this example is probably achieved, although a comparison cannot be made easily. In that case, it is probable that the element employing [Ir(mpptz-tetmb)$_3$] exhibits an external quantum efficiency of approximately 31%; thus, the light-emitting element with the tris iridium complex with high parameter of planarity can be an extremely favorable light-emitting element.

EXAMPLE 3

In this example, a light-emitting element 3 that is the light-emitting element of one embodiment of the present invention described in Embodiment is described. Structural formulae of organic compounds used in the light-emitting element 3 are shown below.

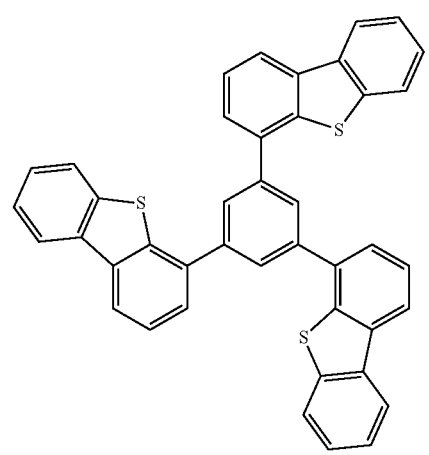

(i) DBT3P-II

-continued

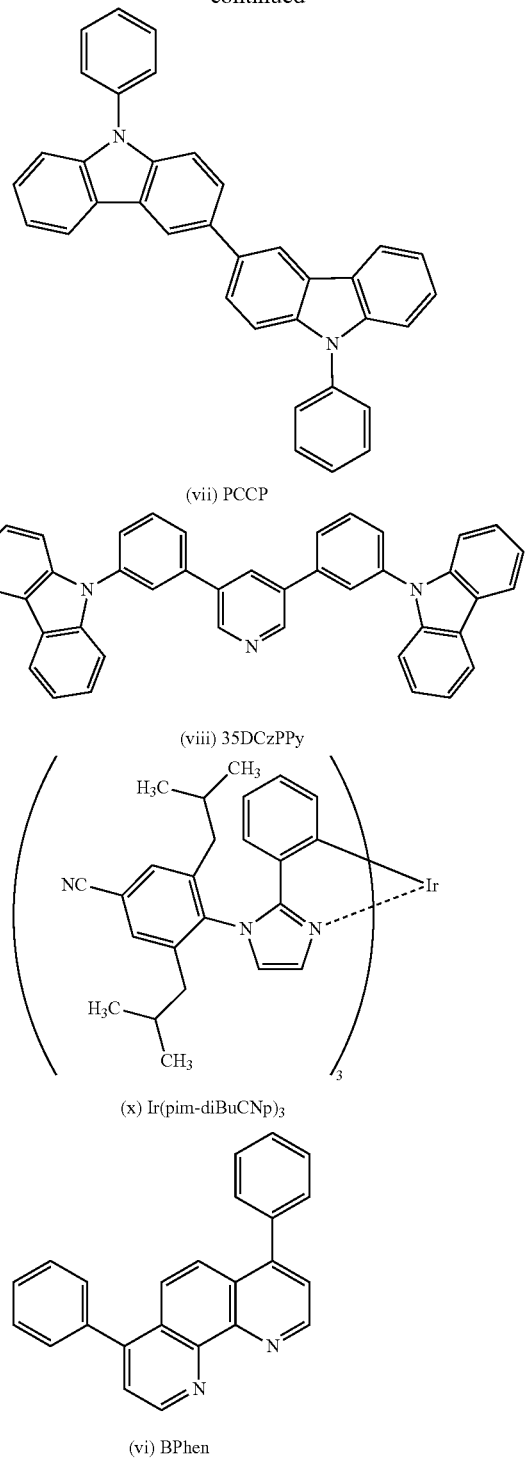

(vii) PCCP (viii) 35DCzPPy (x) Ir(pim-diBuCNp)₃

(vi) BPhen (Fabrication Method of Light-Emitting Element 3)

First, indium tin oxide containing silicon oxide (ITSO) was deposited over a glass substrate by a sputtering method to form the first electrode 101. The thickness of the first electrode 101 was set to 70 nm and the area of the electrode was set to 4 mm² (2 mm×2 mm).

Next, in pretreatment for forming the light-emitting element over the substrate, a surface of the substrate was washed with water and baked at 200° C. for 1 hour, and then UV ozone treatment was performed for 370 seconds.

After that, the substrate was transferred into a vacuum evaporation apparatus whose pressure was reduced to approximately $10^{-4}$ Pa, vacuum baking at 170° C. for 30 minutes was performed in a heating chamber in the vacuum evaporation apparatus, and then the substrate was cooled down for approximately 30 minutes.

Then, the substrate over which the first electrode 101 was formed was fixed to a substrate holder provided in the vacuum evaporation apparatus so that the surface on which the first electrode 101 was formed faced downward. After that, on the first electrode 101, 1,3,5-tri-(4-dibenzothiophenyl)-benzene (abbreviation: DBT3P-II) represented by Structural formula (i) and molybdenum(VI) oxide were deposited by co-evaporation to a thickness of 15 nm at a weight ratio of 2:1 (=DBT3P-II: molybdenum oxide) by an evaporation method using resistance heating, so that the hole-injection layer 111 was formed.

Next, 3,3'-bis(9-phenyl-9H-carbazole) (abbreviation: PCCP) represented by Structural formula (vii) was deposited by evaporation to a thickness of 20 nm over the hole-injection layer 111 to form the hole-transport layer 112.

Next, PCCT, 3,5-bis[3-(9H-carbazol-9-yl)phenyl]pyridine (abbreviation: 35DCzPPy) represented by Structural Formula (viii), and tris{2-[1-(4-cyano-2,6-diisobutylphenyl)-1H-imidazol-2-yl-κN³]phenyl-κC}iridium(III) (abbreviation: [Ir(pim-diBuCNp)₃]) represented by Structural Formula (x) were deposited by co-evaporation to a thickness of 30 nm at a weight ratio of 0.4:0.6:0.125 (=PCCP: 35DCzPPy:[Ir(pim-diBuCNp)₃]), and then 35DCzPPy and [Ir(pim-diBuCNp)₃] were deposited by co-evaporation to a thickness of 10 nm at a weight ratio of 1:0.125 (=35DCzPPy:[Ir(pim-diBuCNp)₃]), so that the light-emitting layer 113 was formed.

Then, 35DCzPPy was deposited by evaporation to a thickness of 10 nm, and bathophenanthroline (abbreviation: BPhen) represented by Structural formula (vi) was deposited by evaporation to a thickness of 15 nm over the light-emitting layer 113 to form the electron-transport layer 114.

After the formation of the electron-transport layer 114, lithium fluoride (LiF) was deposited by evaporation to a thickness of 1 nm to form the electron-injection layer 115. Then, aluminum was deposited by evaporation to a thickness of 200 nm to form the second electrode 102. Through the above-described steps, the light-emitting element 3 of this example was fabricated.

The element structure of the light-emitting element 3 is shown in the following table.

TABLE 9

| | | Light-emitting Layer | | | |
|---|---|---|---|---|---|
| Hole-injection Layer | Hole-transport Layer | First Light-emitting Layer | Second Light-emitting Layer | Electron-transport Layer | Electron-injection Layer |
| DBT3P-II: MoOx | PCCP | PCCP: 35DCzPPy: | 35DCzPPy: Ir(pim- | 35DCzPPy BPhen | LiF |

TABLE 9-continued

| | | Light-emitting Layer | | | |
|---|---|---|---|---|---|
| Hole-injection Layer | Hole-transport Layer | First Light-emitting Layer | Second Light-emitting Layer | Electron-transport Layer | Electron-injection Layer |
| (2:1) | | Ir(pim-diBuCNp)₃ (0.4:0.6:0.125) | diBuCNp3 (1:0.125) | | |
| 15 nm | 20 nm | 30 nm | 10 nm | 10 nm    15 nm | 1 nm |

The light-emitting element 3 was sealed using a glass substrate in a glove box containing a nitrogen atmosphere so as not to be exposed to the air (specifically, a sealing material was applied to surround the element, UV treatment and heat treatment at 80° C. for 1 hour were performed at the time of sealing). Then, initial characteristics of the light-emitting element were measured. The measurement was carried out at room temperature (under an atmosphere where a temperature was maintained at 25° C.).

Figure 32:
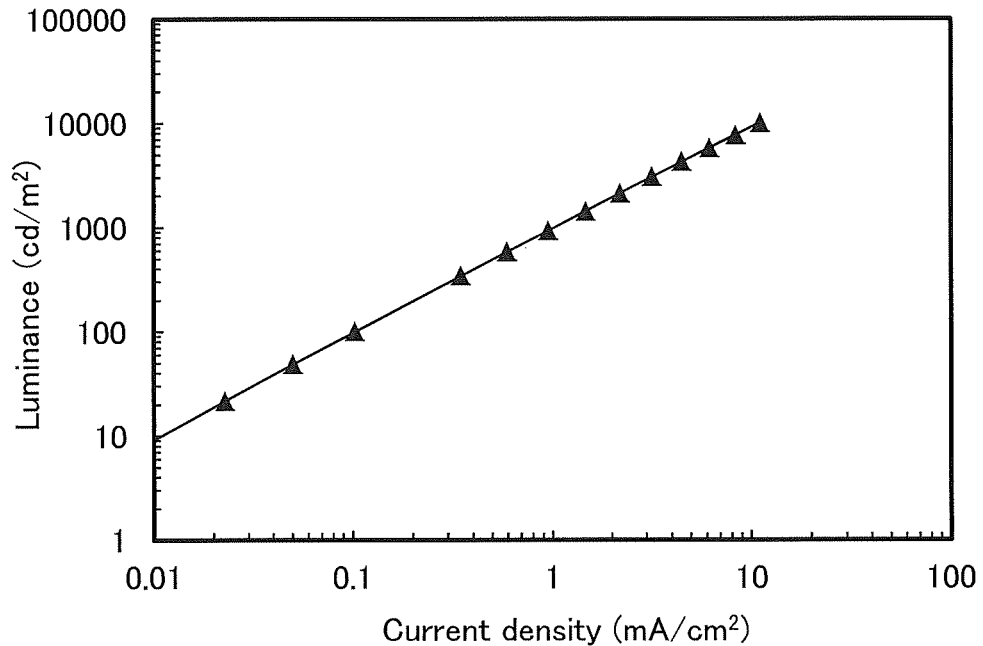
FIG. 32 shows the luminance-current density characteristics of a light-emitting element 3.
Figure 33:
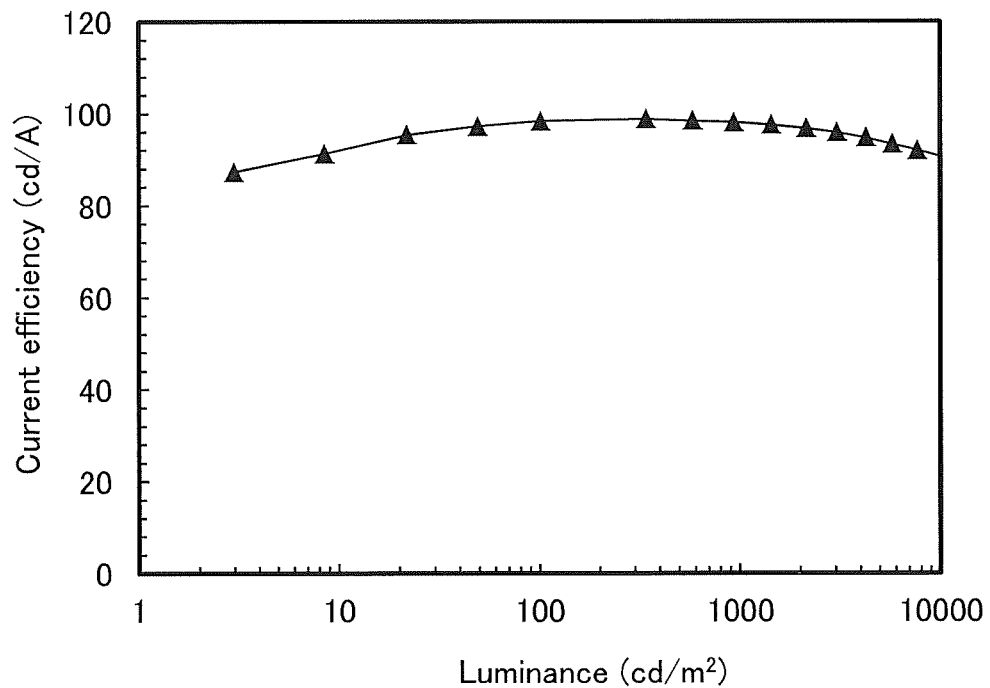
FIG. 33 shows the current efficiency-luminance characteristics of the light-emitting element 3.
Figure 34:
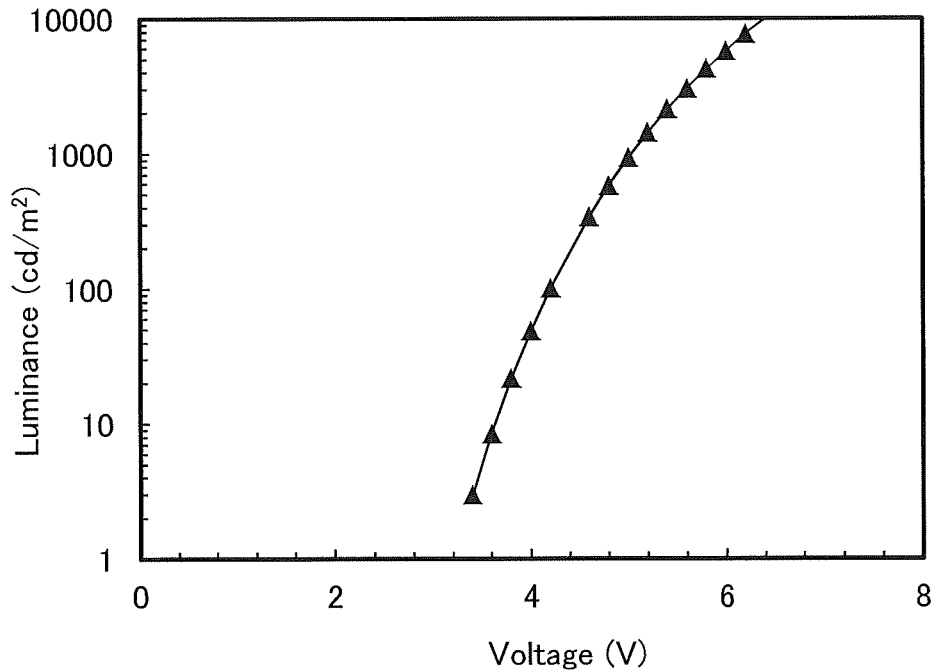
FIG. 34 shows the luminance-voltage characteristics of the light-emitting element 3.
Figure 35:
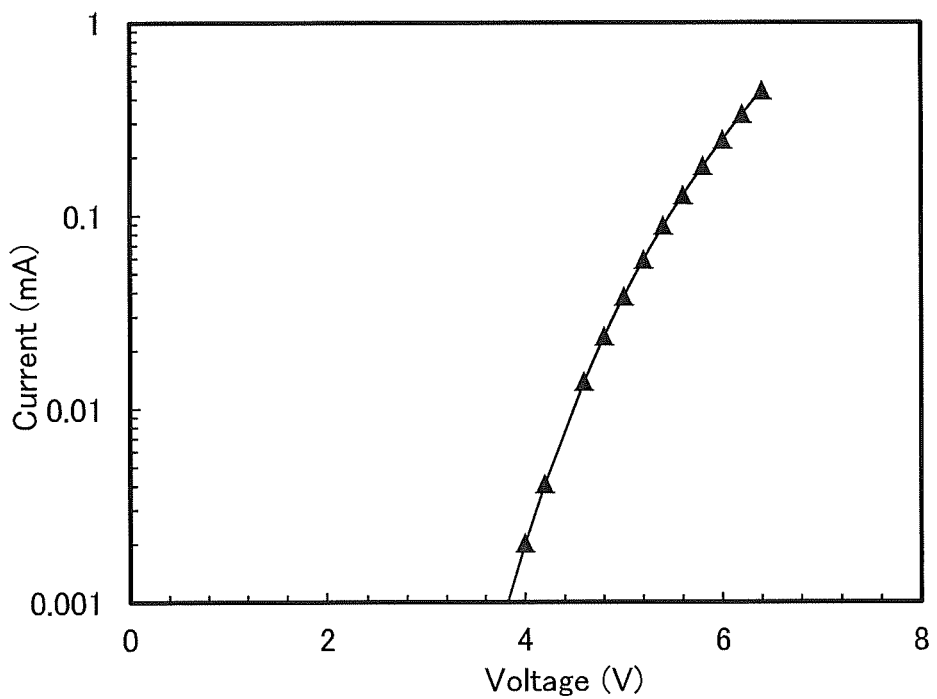
FIG. 35 shows the current-voltage characteristic of the light-emitting element 3.
Figure 36:
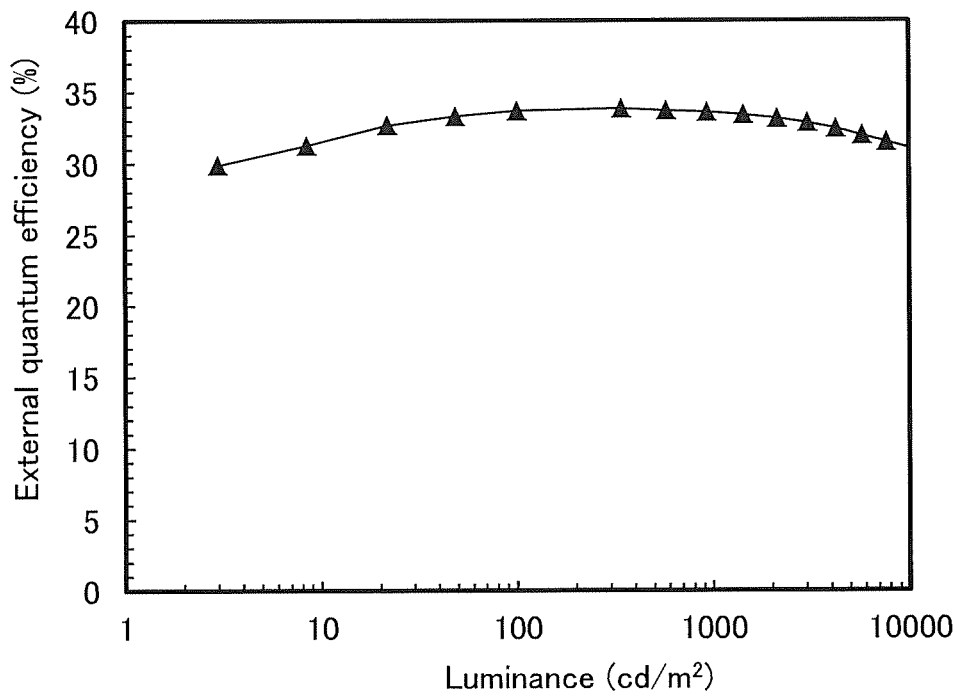
FIG. 36 shows the external quantum efficiency-luminance characteristics of the light-emitting element 3.
Figure 37:
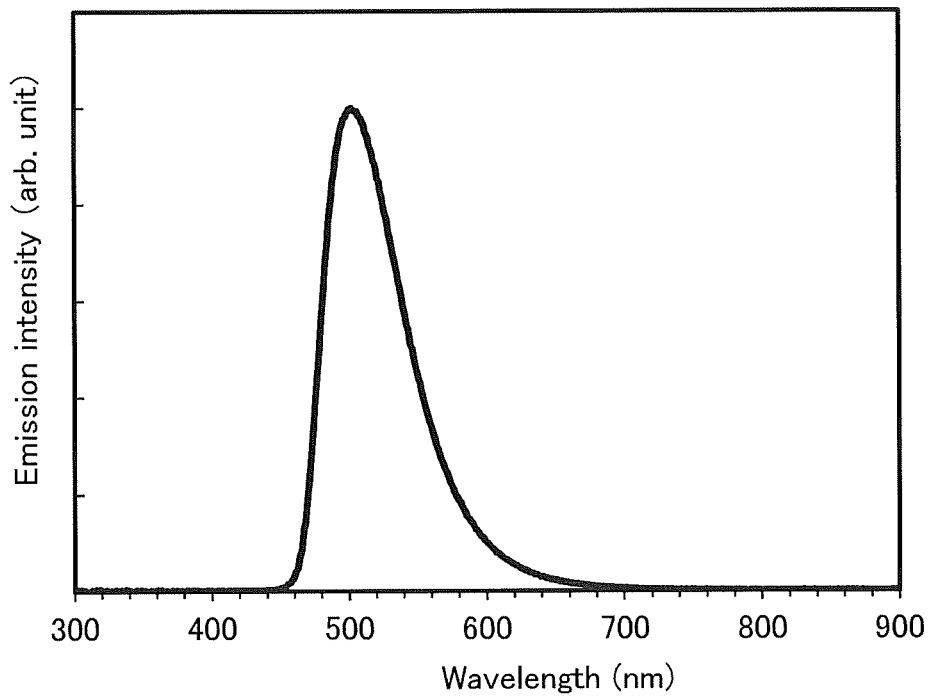
FIG. 37 shows the emission spectrum of the light-emitting element 3.

FIG. 32 shows the luminance-current density characteristics of the light-emitting element 3. FIG. 33 shows the current efficiency-luminance characteristics of the light-emitting element 3. FIG. 34 shows the luminance-voltage characteristics of the light-emitting element 3. FIG. 35 shows the current-voltage characteristics of the light-emitting element 3. FIG. 36 shows the external quantum efficiency-luminance characteristics of the light-emitting element 3. FIG. 37 shows the emission spectrum of the light-emitting element 3.

TABLE 10

| Voltage (V) | Current (mA) | Current Density (mA/cm²) | Current Efficiency (cd/A) | External Quantum Efficiency (%) |
|---|---|---|---|---|
| 5.0 | 0.038 | 1.0 | 98.1 | 33.6 |

The results shown in FIG. 32, FIG. 33, FIG. 34, FIG. 35, FIG. 36, FIG. 37, and Table 10 indicate that the light-emitting element 3 exhibits extremely high efficiency, i.e., the external quantum efficiency at 1000 cd/m² is 33.6%, the maximum external quantum efficiency is 33.8%.

Note that the parameter of planarity (A×B/C²) of [Ir(pim-diBuCNp)₃] was calculated to be 4.3. In this manner, the light-emitting element formed using the tris iridium complex with high parameter of planarity can exhibit extremely high efficiency.

Reference Example 1

In this reference example, a method for synthesizing tris{2-[4-(4-cyano-2,6-diisobutylphenyl)-5-(2-methylphenyl)-4H-1,2,4-triazol-3-yl-κN²]phenyl-κC}iridium(III) (abbreviation: [Ir(mpptz-diBuCNp)₃]), which is described in Embodiment, is described. The structure of Ir(mpptz-diBuCNp)₃ is shown below.

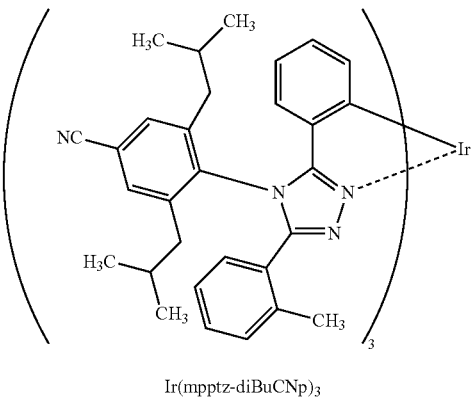

Ir(mpptz-diBuCNp)₃

Step 1: Synthesis of
4-amino-3,5-diisobutylbenzonitrile

Into a 1000 mL three-neck flask were put 9.4 g (50 mmol) of 4-amino-3,5-dichlorobenzonitrile, 26 g (253 mmol) of isobutylboronic acid, 54 g (253 mmol) of tripotassium phosphate, 2.0 g (4.8 mmol) of 2-dicyclohexylphosphino-2',6'-dimethoxybiphenyl (S-phos), and 500 mL of toluene. The atmosphere in the flask was replaced with nitrogen, and this mixture was degassed while being stirred under reduced pressure. After the degassing, 0.88 g (0.96 mmol) of tris(dibenzylideneacetone)palladium(0) was added, and the mixture was stirred under a nitrogen stream at 130° C. for 8 hours to be reacted. Toluene was added to the obtained reacted solution, and the mixture was filtered through a filter aid in which Celite (Catalog No. 531-16855, manufactured by Wako Pure Chemical Industries, Ltd. (the same applies to Celite in the following description)), aluminum oxide, and Celite were stacked in this order. The obtained filtrate was concentrated to give an oily substance. The obtained oily substance was purified by silica column chromatography. Toluene was used as a developing solvent. The resulting fraction was concentrated to give 10 g of a yellow oily substance in a yield of 87%. The obtained yellow oily substance was identified as 4-amino-3,5-diisobutylbenzonitrile by nuclear magnetic resonance (NMR). The synthesis scheme of Step 1 is shown below.

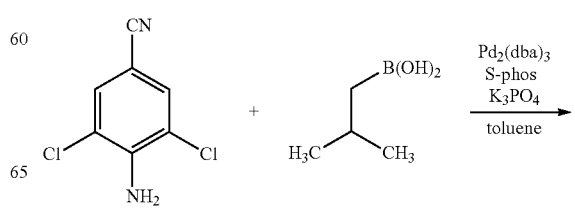

-continued

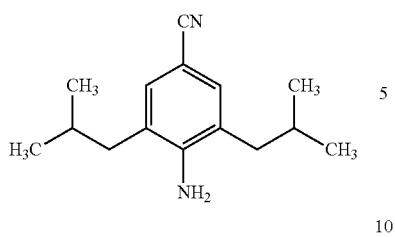

Step 2: Synthesis of 4-(4-cyano-2,6-diisobutylphenyl)-3-(2-methylphenyl)-5-phenyl-4H-1,2,4-triazole (Abbreviation: Hmpptz-diBuCNp)

Into a 300 mL three-neck flask were put 11 g (48 mmol) of 4-amino-3,5-diisobutylbenzonitrile synthesized in Step 1, 4.7 g (16 mmol) of N-(2-methylphenyl)chloromethylidene-N'-phenylchloromethylidenehydrazine, and 40 mL of N,N-dimethylaniline, and the mixture was stirred under a nitrogen stream at 160° C. for 7 hours to be reacted. After the reaction, the reacted solution was added to 300 mL of 1M hydrochloric acid and stirring was performed for 3 hours. An organic layer and an aqueous layer were separated, and the aqueous layer was subjected to extraction with ethyl acetate. The organic layer and the obtained solution of the extract were combined, and washed with a saturated aqueous solution of sodium hydrogen carbonate and then with saturated saline, and anhydrate magnesium sulfate was added to the organic layer for drying. The mixture was gravity-filtered and the filtrate was concentrated to give an oily substance. The obtained oily substance was purified by silica column chromatography. As the developing solvent, a 5:1 hexane-ethyl acetate mixed solvent was used. The obtained fraction was concentrated to give a solid. Hexane was added to the obtained solid, and the mixture was irradiated with ultrasonic waves and then subjected to suction filtration to give 2.0 g of a white solid in a yield of 28%. The obtained white solid was identified as Hmpptz-diBuCNp by nuclear magnetic resonance (NMR). The synthesis scheme of Step 2 is shown below.

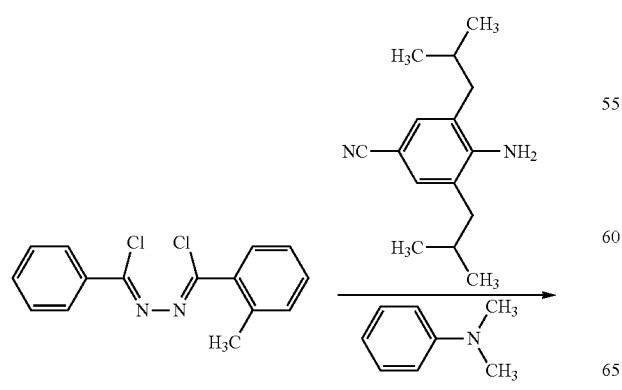

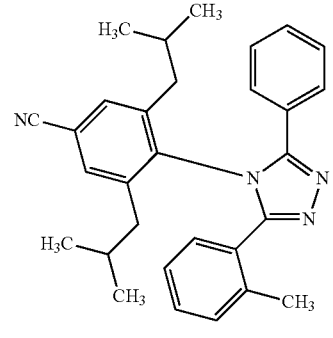

Hmpptz-diBuCNp

Step 3: Synthesis of tris{2-[4-(4-cyano-2,6-diisobutylphenyl)-5-(2-methylphenyl)-4H-1,2,4-triazol-3-yl-κN²]phenyl-κC}iridium(III) (Abbreviation: [Ir(mpptz-diBuCNp)₃])

Into a reaction container provided with a three-way cock were put 2.0 g (4.5 mmol) of Hmpptz-diBuCNp synthesized in Step 2 and 0.44 g (0.89 mmol) of tris(acetylacetonato)iridium(III), and the mixture was stirred under an argon stream at 250° C. for 43 hours to be reacted. The obtained reaction mixture was added to dichloromethane, and an insoluble matter was removed. The obtained filtrate was concentrated to obtain a solid. The obtained solid was purified by silica column chromatography. Dichloromethane was used as a developing solvent. The obtained fraction was concentrated to give a solid. The obtained solid was recrystallized from ethyl acetate/hexane, so that 0.32 g of a yellow solid was obtained in a yield of 23%. Then 0.31 g of the obtained yellow solid was purified by a train sublimation method. The purification by sublimation was performed by heating at 310° C. under a pressure of 2.6 Pa with an argon flow rate of 5.0 mL/min for 19 hours. After the purification by sublimation, 0.26 g of a yellow solid was obtained at a collection rate of 84%. The synthesis scheme of Step 3 is shown below.

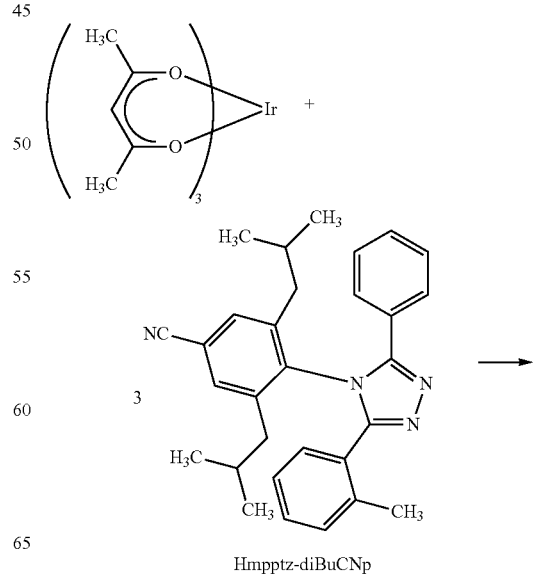

Hmpptz-diBuCNp

-continued

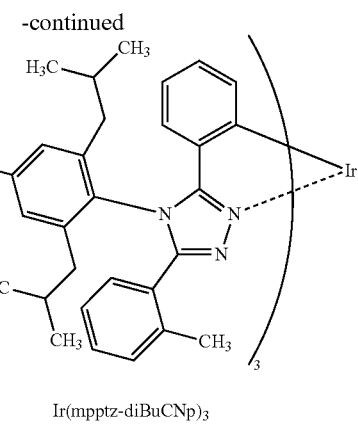

Ir(mpptz-diBuCNp)₃

The protons (¹H) of the yellow solid that was obtained in Step 3 was measured by nuclear magnetic resonance (NMR). The obtained values are shown below. The result revealed that [Ir(mpptz-diBuCNp)₃] was obtained by the synthesis method.

¹H-NMR δ (CDCl₃): 0.33 (d, 18H), 0.92 (d, 18H), 1.51-1.58 (m, 3H), 1.80-1.88 (m, 6H), 2.10-2.15 (m, 6H), 2.26-2.30 (m, 3H), 2.55 (s, 9H), 6.12 (d, 3H), 6.52 (t, 3H), 6.56 (d, 3H), 6.72 (t, 3H), 6.83 (t, 3H), 6.97 (d, 3H), 7.16 (t, 3H), 7.23 (d, 3H), 7.38 (s, 3H), 7.55 (s, 3H).

Reference Example 2

In this reference example, an example of a method for synthesizing tris{4'-cyano-2',6'-dimethyl-3-[3-methyl-1-(2,4,6-trimethylphenyl)-1H-1,2,4-triazol-5-yl-κN⁴]-1,1'-biphenyl-4-yl-κC}iridium(III) (abbreviation: [Ir(MdmCN5btz1-tmp)₃]), which is used in Example 1, is described in detail. The structure of [Ir(MdmCN5btz1-tmp)₃] is shown below.

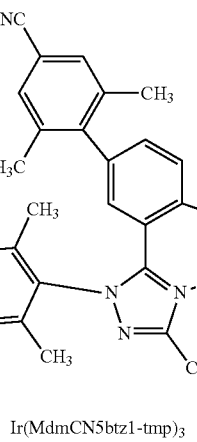

Ir(MdmCN5btz1-tmp)₃

Step 1: Synthesis of 4-cyano-2,6-dimethylphenylboronic acid pinacol ester

First, 5.0 g (24 mmol) of 4-bromo-3,5-dimethylbenzonitrile, 7.3 g (29 mmol) of bis(pinacolato)diboron, 8.4 g (86 mmol) of potassium acetate, and 120 mL of dimethyl sulfoxide (DMSO) were put into a three-neck flask, and the atmosphere in the flask was replaced with nitrogen. To this mixture were added 0.20 g (0.24 mmol) of [1,1'-bis(diphenylphosphino)ferrocene]palladium(II) dichloromethane adduct and 0.20 g (0.48 mmol) of 2-dicyclohexylphosphino-2',6'-dimethoxybiphenyl (S-phos), and the mixture was heated and stirred at 90° C. for 7 hours. To this mixture were further added 0.20 g (0.24 mmol) of [1,1'-bis(diphenylphosphino)ferrocene]palladium(II) dichloromethane adduct, 0.20 g (0.48 mmol) of 2-dicyclohexylphosphino-2',6'-dimethoxybiphenyl (S-phos), and 3.5 g (14 mmol) of bis(pinacolato)diboron were further added to, and the mixture was heated and stirred at 100° C. for 17 hours to be reacted. Water was added to the reacted solution to separate the solution into an organic layer and an aqueous layer, and the aqueous layer was subjected to extraction with toluene. A solution obtained by combining the organic layer and the solution of the extract was washed with water and saturated saline, and anhydrous magnesium sulfate was added thereto for drying. The obtained mixture was subjected to gravity filtration, and the filtrate was concentrated to give a solid. This solid was purified by flash column chromatography. As developing solvents, first, a mixed solvent of toluene and ethyl acetate in a ratio of 10:1 (v:v) was used, and then a mixed solvent of toluene and ethyl acetate in a ratio of 5:1 (v:v) was used. The obtained fraction was concentrated to give a solid. This solid was washed with toluene and hexane, so that 3.5 g of a white solid was obtained in a yield of 57%. The obtained white solid was identified as 4-cyano-2,6-dimethylphenylboronic acid pinacol ester by nuclear magnetic resonance (NMR). The synthesis scheme of Step 1 is shown below.

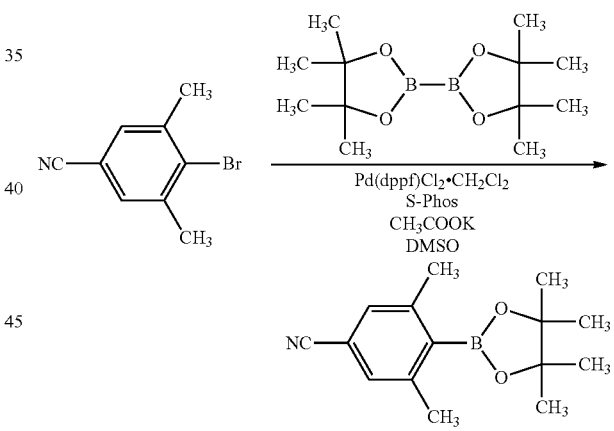

Step 2: Synthesis of 5-(4'-cyano-2',6'-dimethyl-1,1'-biphenyl-3-yl)-3-methyl-1-(2,4,6-trimethylphenyl)-1H-1,2,4-triazole (Abbreviation: HMdmCN5btz1-tmp)

Into a three-neck flask were put 4.0 g (11 mmol) of 5-(3-bromophenyl)-1-(2,4,6-trimethylphenyl)-3-methyl-1H-1,2,4-triazole, 3.2 g (12 mmol) of 4-cyano-2,6-dimethylphenylboronic acid pinacol ester obtained in Step 1, 4.1 g (20 mmol) of potassium phosphate, 75 mL of toluene, and 7 mL of water. The atmosphere in the flask was replaced with nitrogen. To this mixture were added 0.26 g (0.45 mmol) of bis(dibenzylideneacetone)palladium(0) and 0.37 g (0.90 mmol) of 2-dicyclohexylphosphino-2',6'-dimethoxybiphenyl (S-phos), and the mixture was heated and stirred at 90° C. for 7.5 hours to be reacted. After the reaction, an organic layer and an aqueous layer of the obtained reacted solution were separated, the aqueous layer was subjected to extraction with toluene, and the solution of the extract and the organic layer were combined and washed with water and saturated saline. Anhydrous magnesium sulfate was added to the organic layer for drying. The obtained mixture was subjected to gravity filtration, and the filtrate was concentrated to give an oily substance. This oily substance was purified by flash column chromatography. As developing solvents, toluene was used, and then ethyl acetate was added to increase the polarity such that the ratio of toluene: ethyl acetate=4:1. The obtained fraction was concentrated to give a solid. This solid was washed with ethanol, so that 3.9 g of a white solid was obtained in a yield of 85%. The obtained white solid was identified as 5-(4'-cyano-2',6'-dimethyl-1,1'-biphenyl-3-yl)-3-methyl-1-(2,4,6-trimethylphenyl)-1H-1,2,4-triazole (abbreviation: HMdmCN5btz1-tmp) by nuclear magnetic resonance (NMR). The synthesis scheme of Step 2 is shown below.

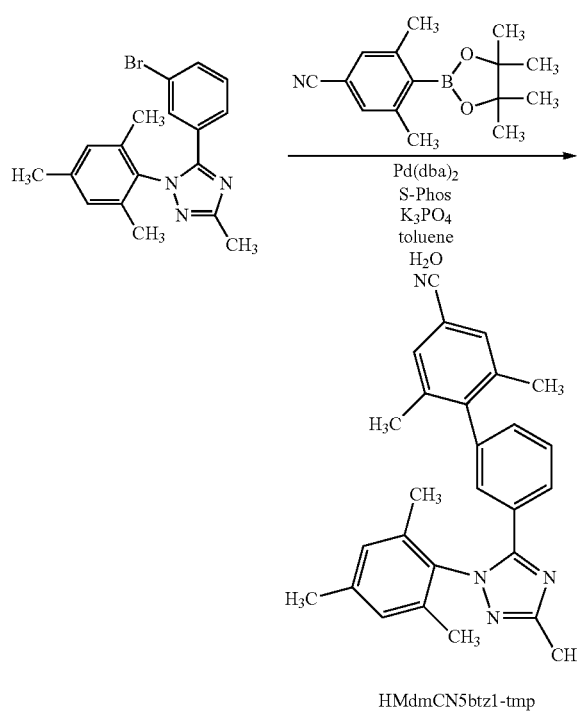

Step 3: Synthesis of tris{4'-cyano-2',6'-dimethyl-3-[3-methyl-1-(2,4,6-trimethylphenyl)-1H-1,2,4-triazol-5-yl-κN⁴]-1,1'-biphenyl-4-yl-κC}iridium(III) (Abbreviation: [Ir(MdmCN5btz1-tmp)₃])

Into a 50 mL recovery flask were put 1.0 g (2.5 mmol) of a ligand HMdmCN5btz1-tmp obtained in Step 2, 0.33 g (1.1 mmol) of iridium chloride hydrate, 15 mL of 2-ethoxyethanol, and 5 mL of water. The atmosphere in the flask was replaced with argon. This flask was heated by irradiation with microwaves under conditions of 100 W and 100° C. for one hour to cause a reaction. After the reaction, the reacted solution was concentrated to give a yellow oily substance. To this oily substance were added 0.58 g (2.2 mmol) of silver trifluoromethanesulfonate and 2.28 g (5.61 mmol) of a ligand HMdmCN5btz1-tmp. The atmosphere in the flask was replaced with nitrogen, and the mixture was heated and stirred at 165° C. for 23 hours. After the reaction, the reaction mixture was dissolved in dichloromethane, and the mixture was subjected to suction filtration to remove an insoluble solid. The resulting filtrate was purified by silica column chromatography. As a developing solvent, a mixed solvent of dichloromethane and ethyl acetate in a ratio of 5:1 (v:v) was used. The obtained fraction was concentrated to give a solid. This solid was recrystallized from ethyl acetate/hexane, so that 8 mg of a yellow solid was obtained in a yield of 0.5%. The obtained yellow solid was identified as [Ir(MdmCN5btz1-tmp)₃] by nuclear magnetic resonance (NMR). The synthesis scheme of Step 3 is shown below.

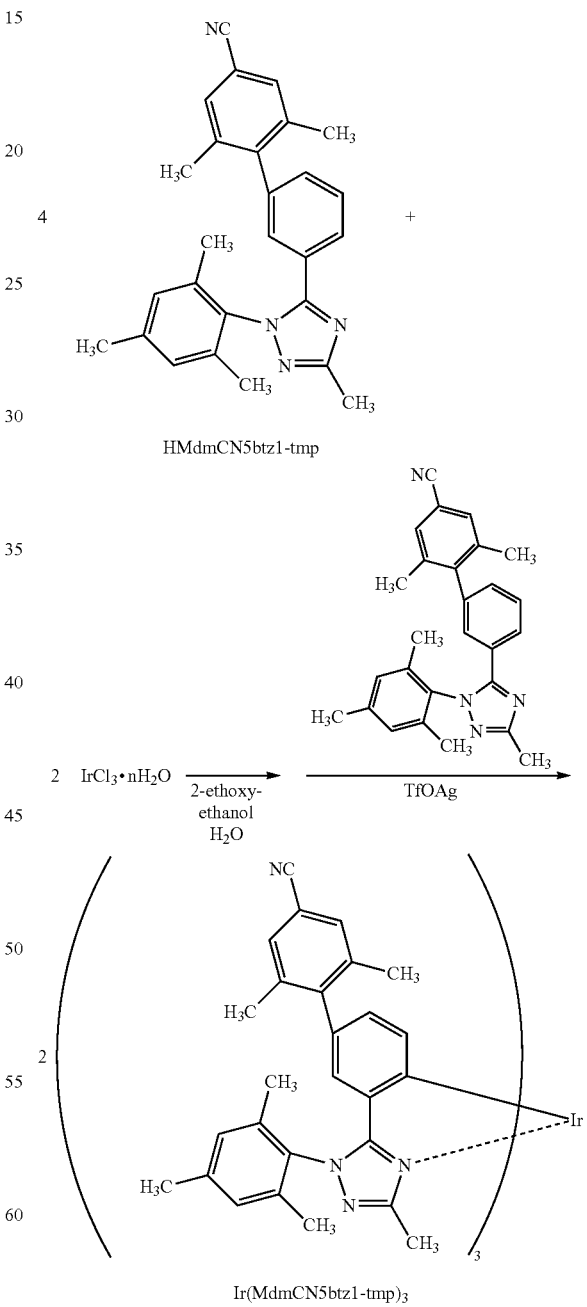

The protons (¹H) of the yellow solid that was obtained in Step 3 was measured by nuclear magnetic resonance (NMR). The obtained values are shown below. The results revealed that [Ir(MdmCN5btz1-tmp)₃] was obtained.

¹H-NMR δ (CD₂Cl₂): 1.71 (s, 9H), 1.86 (s, 9H), 1.90 (s, 9H), 2.10 (s, 9H), 2.12 (s, 9H), 2.28 (s, 9H), 6.19 (d, 3H), 6.44 (dd, 3H), 6.70 (d, 3H), 6.95 (s, 3H), 7.00 (s, 3H), 7.25 (s, 6H).

Reference Example 3

In this reference example, a method for synthesizing tris{2-[1-(4-cyano-2,6-diisobutylphenyl)-1H-imidazol-2-yl-κN³]phenyl-κC}iridium(III) (abbreviation: [Ir(pim-diBuCNp)₃]), which is the organometallic complex used in Example 3, is described. The structural formula of [Ir(pim-diBuCNp)₃] is shown below.

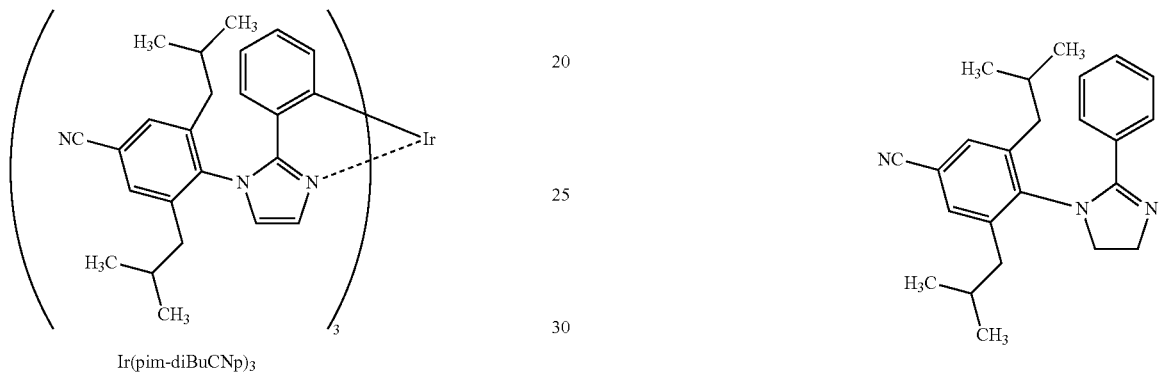

Step 1: Synthesis of 1-(4-cyano-2,6-diisobutylphenyl)-2-phenyl-4,5-dihydro-1H-imidazole Into a 1000 mL three-neck flask were put 22 g (117 mmol) of N-(2-chloroethyl)benzamide and 260 mL of dehydrated xylene. To this mixed solution was added 33 g (158 mmol) of phosphorus pentachloride, and the mixture was heated and stirred at 140° C. for one hour to be reacted. After the reaction, the mixture was cooled down to room temperature, a mixed solution of 28 g (120 mmol) of 4-amino-3,5-diisobutylbenzonitrile and 60 mL of dehydrated xylene was dropped thereinto, and heating and stirring were performed at 140° C. for 5 hours. This reaction mixture was slowly added to 500 mL of water and stirring was performed at room temperature for 30 minutes. To this mixture was added chloroform. The obtained solution of the extract was slowly added to a 1M sodium hydroxide aqueous solution and the mixture was stirred at room temperature for 30 minutes. An aqueous layer and an organic layer of this mixture were separated. The obtained solution of the extract was washed with a saturated aqueous solution of sodium hydrogen carbonate, and then washed with saturated saline. After washing, anhydrous magnesium sulfate was added to the organic layer for drying, and the resulting mixture was subjected to gravity filtration to give a filtrate. The obtained filtrate was concentrated to give a solid. A mixed solvent of ethyl acetate and hexane was added to the solid, the mixture was subjected to suction filtration, whereby 33 g of a white solid was obtained in a yield of 79%. The obtained white solid was identified as 1-(4-cyano-2,6-diisobutylphenyl)-2-phenyl-4,5-dihydro-1H-imidazole by nuclear magnetic resonance (NMR). A synthesis scheme of Step 1 is shown in (a-2).

Step 2: Synthesis of 1-(4-cyano-2,6-diisobutylphenyl)-2-phenyl-1H-imidazole (Abbreviation: Hpim-diBuCNp)

Into a 200 mL three-neck flask were put 15 g (42 mmol) of 1-(4-cyano-2,6-diisobutylphenyl)-2-phenyl-4,5-dihydro-1H-imidazole synthesized in Step 1 and acetonitrile. To the mixed solution was added a powder obtained by putting 13 g (84 mmol) of potassium permanganate and 29 g of aluminum oxide in a mortar and grinding them, and the mixture was stirred at room temperature for 17 hours to be reacted. This reaction mixture was subjected to suction filtration through Celite. The obtained filtrate was concentrated to give an oily substance. Toluene was added to the obtained oily substance, and the mixture was filtered through a filter aid in which Celite, aluminum oxide, and Celite were stacked in this order. The obtained filtrate was concentrated to give an oily substance. The obtained oily substance was purified by silica column chromatography. As the developing solvent, a 5:1 hexane-ethyl acetate mixed solvent was used. The obtained fraction was concentrated to give 8.0 g of a colorless oily substance in a yield of 53%. The obtained colorless oily substance was identified as 1-(4-cyano-2,6-diisobutylphenyl)-2-phenyl-1H-imidazole (abbreviation: Hpim-diBuCNp) by nuclear magnetic resonance (NMR). A synthesis scheme of Step 2 is shown in (b-2).

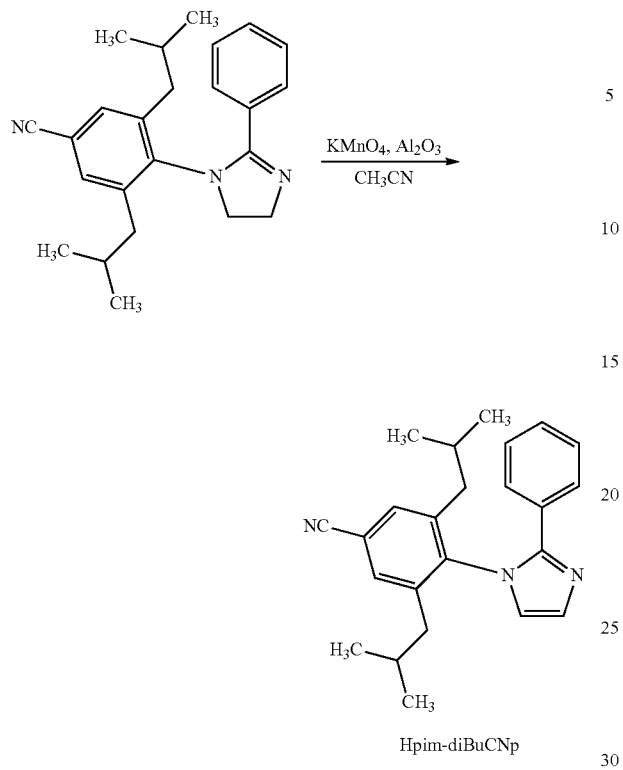

Hpim-diBuCNp

Step 3: Synthesis of [Ir(pim-diBuCNp)₃]

Into a reaction container equipped with a three-way cock were put 5.0 g (14 mmol) of 1-(4-cyano-2,6-diisobutylphenyl)-2-phenyl-1H-imidazole synthesized in Step 2 and 1.4 g (2.8 mmol) of tris(acetylacetonato)iridium(III), and the mixture was heated at 250° C. under an argon stream for 38 hours to be reacted. Toluene was added to the obtained reaction mixture, and an insoluble matter was removed. The obtained filtrate was concentrated to obtain a solid. The obtained solid was purified by silica column chromatography. As a developing solvent, first, toluene was used. Next, a 9:1 toluene-ethyl acetate mixed solvent was used. The obtained fraction was concentrated to give a solid. The obtained solid was recrystallized from ethyl acetate/hexane, so that 0.6 g of a yellow solid was obtained in a yield of 18%. Then, 0.6 g of the obtained yellow solid was purified by a train sublimation method. The purification by sublimation was performed by heating at 280° C. under a pressure of 2.6 Pa with an argon flow rate of 5.0 mL/min for 17 hours. After the purification by sublimation, 0.4 g of a yellow solid was obtained at a collection rate of 67%. A synthesis scheme of Step 3 is shown in (c-2).

The protons (¹H) of the yellow solid that was obtained in Step 3 was measured by a nuclear magnetic resonance (NMR). The obtained values are shown below. These results reveal that [Ir(pim-diBuCNp)₃] was obtained.

¹H-NMR δ (CDCl₃): 0.43 (d, 9H), 0.56 (d, 9H), 0.79 (t, 18H), 1.42-1.50 (m, 3H), 1.73-1.81 (m, 3H), 1.97-2.02 (m, 3H), 2.12-2.17 (m, 3H), 2.24-2.29 (m, 3H), 2.46-2.50 (m, 3H), 6.05 (d, 3H), 6.40 (t, 3H), 6.59 (t, 3H), 6.71-6.76 (m, 9H), 7.54 (d, 6H).

Reference Example 4

In this reference example, a method for synthesizing tris{2-[5-(2-methylphenyl)-4-(3,3',5,5'-tetramethyl-1,1'-biphenyl-4-yl)-4H-1,2,4-triazol-3-yl-κN²]phenyl-κC}iridium (III) (abbreviation: [Ir(mpptz-tetmb)₃]), which is the organometallic complex described in Embodiment, is described. The structure of [Ir(mpptz-tetmb)₃] is shown below.

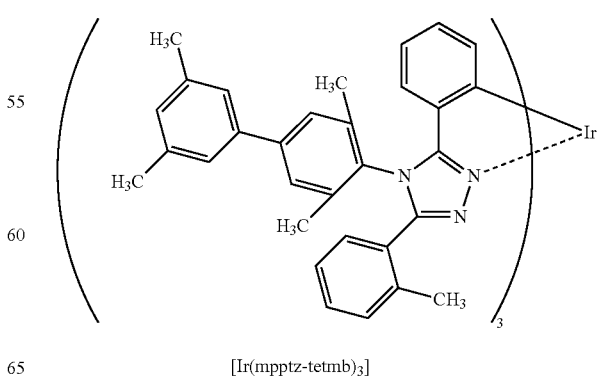

[Ir(mpptz-tetmb)₃]

Step 1: Synthesis of 4-(4-bromo-2,6-dimethylphenyl)-5-(2-methylphenyl)-3-phenyl-4H-1,2,4-triazole Into a 300 mL three-neck flask were put 8.5 g (28 mmol) of N-(2-methylphenyl)chloromethylidene-N'-phenylchloromethylidenehydrazine, 17 g (85 mmol) of 4-bromo-2,6-dimethylaniline, and 40 mL of N,N-dimethylaniline, and the mixture was heated and stirred under a nitrogen stream at 180° C. for 14 hours. After reaction for the predetermined time, the reacted solution was put into 1M hydrochloric acid and stirred for 2 days. After the reaction, extraction was performed with ethyl acetate. Then, purification was performed by silica column chromatography. As a developing solvent, a 2:1 hexane-ethyl acetate mixed solvent was used. The obtained fraction was concentrated to give a white solid. The obtained solid was recrystallized from ethyl acetate/hexane to give 5.5 g of a white solid in a yield of 46%. The obtained white solid was identified as 4-(4-bromo-2,6-dimethylphenyl)-5-(2-methylphenyl)-3-phenyl-4H-1,2,4-triazole by nuclear magnetic resonance (NMR). The synthesis scheme of Step 1 is shown below.

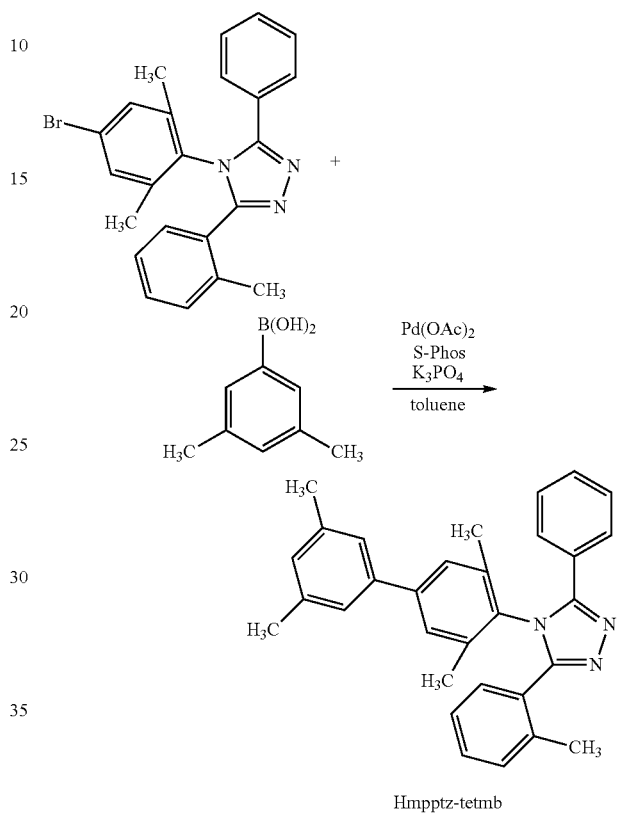

Step 2: Synthesis of 5-(2-methylphenyl)-4-(3,3',5,5'-tetramethyl-1,1'-biphenyl-4-yl)-2-phenyl-4H-1,2,4-triazole (Abbreviation: Hmpptz-tetmb)

Into a 200 mL three-neck flask were put 5.5 g (13 mmol) of 4-(4-bromo-2,6-dimethylphenyl)-5-(2-methylphenyl)-3-phenyl-4H-1,2,4-triazole synthesized in Step 1, 2.3 g (16 mmol) of 3,5-dimethylphenylboronic acid, 3.3 g (16 mmol) of tripotassium phosphate, 0.32 g (0.78 mmol) of 2-dicyclohexylphosphino-2',6'-dimethoxybiphenyl (abbreviation: S-Phos), and 60 mL of toluene. The atmosphere in the flask was replaced with nitrogen, and the mixture was degassed while being stirred under reduced pressure. After the degassing, 0.088 g (0.39 mmol) of palladium(II) acetate was added, and the mixture was stirred under a nitrogen stream at 100° C. for 22 hours. After the reaction for the predetermined time, water was added to the obtained reacted solution, and extraction was performed with chloroform. After that, purification was performed by silica column chromatography. As a developing solvent, a 3:1 toluene-ethyl acetate mixed solvent was used. The obtained fraction was concentrated to give a white solid. The obtained solid was recrystallized from ethyl acetate to give 4.0 g of a white solid in a yield of 69%. The obtained white solid was identified as Hmpptz-tetmb by nuclear magnetic resonance (NMR). The synthesis scheme of Step 2 is shown below.

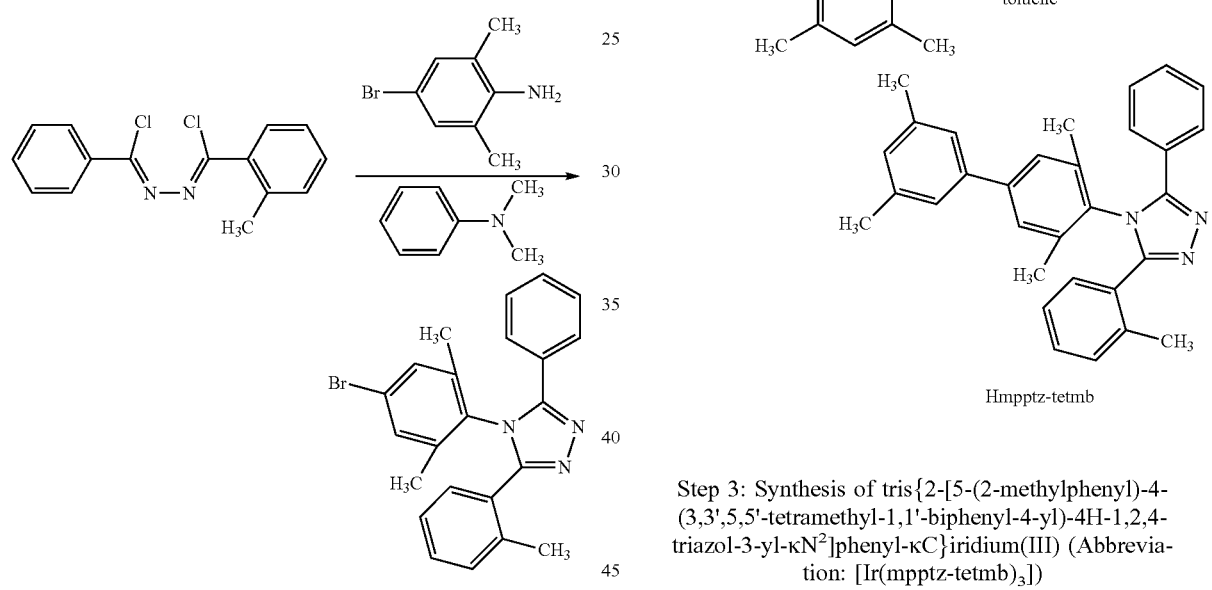

Step 3: Synthesis of tris{2-[5-(2-methylphenyl)-4-(3,3',5,5'-tetramethyl-1,1'-biphenyl-4-yl)-4H-1,2,4-triazol-3-yl-κN²]phenyl-κC}iridium(III) (Abbreviation: [Ir(mpptz-tetmb)₃])

Into a reaction container provided with a three-way cock were put 4.0 g (9.0 mmol) of Hmpptz-tetmb synthesized in Step 2 and 0.88 g (1.8 mmol) of tris(acetylacetonato)iridium (III), and the mixture was heated under an argon stream at 250° C. for 43 hours. Dichloromethane was added to the obtained reaction mixture, and the mixture was irradiated with ultrasonic waves and then subjected to suction filtration to give a solid. Toluene was added to the solid, and the mixture was heated so that the solid was dissolved and then subjected to gravity filtration to remove a solid, which serves as an impurity. The obtained filtrate was recrystallized to give 0.93 g of a yellow solid, which was the object of the synthesis, in a yield of 34%. Then, 0.92 g of the obtained solid was purified by a train sublimation method. The purification by sublimation was performed by heating at 375° C. under a pressure of $1.7\times10^{-2}$ Pa with an argon flow rate of 0 mL/min for 24 hours. After the purification by sublimation, 0.046 g of a yellow solid was obtained at a collection rate of 5%. The synthesis scheme of Step 3 is shown below.

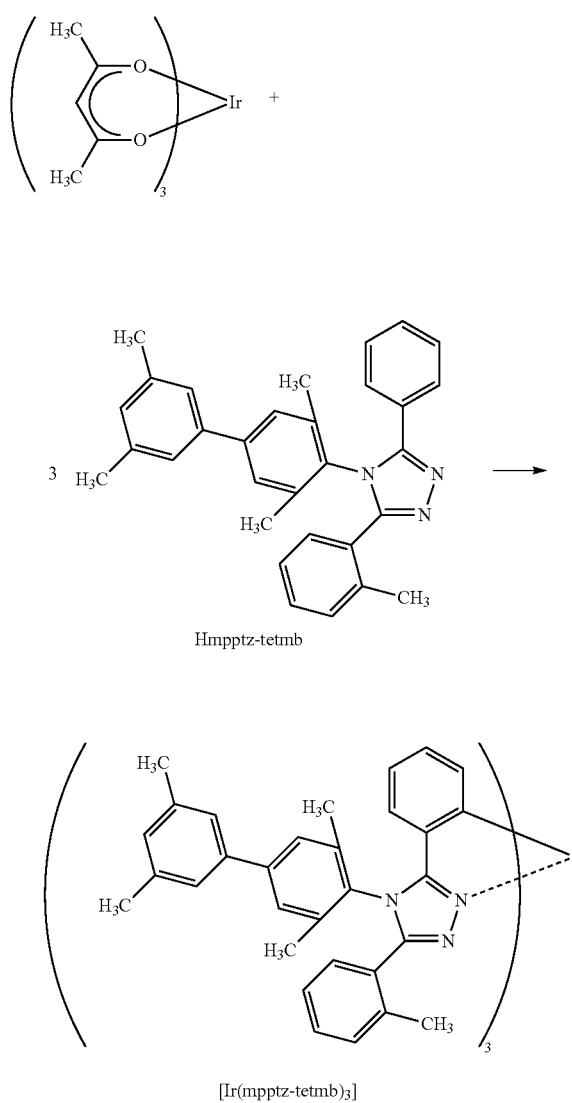

Hmpptz-tetmb

[Ir(mpptz-tetmb)₃]

Figure 38:
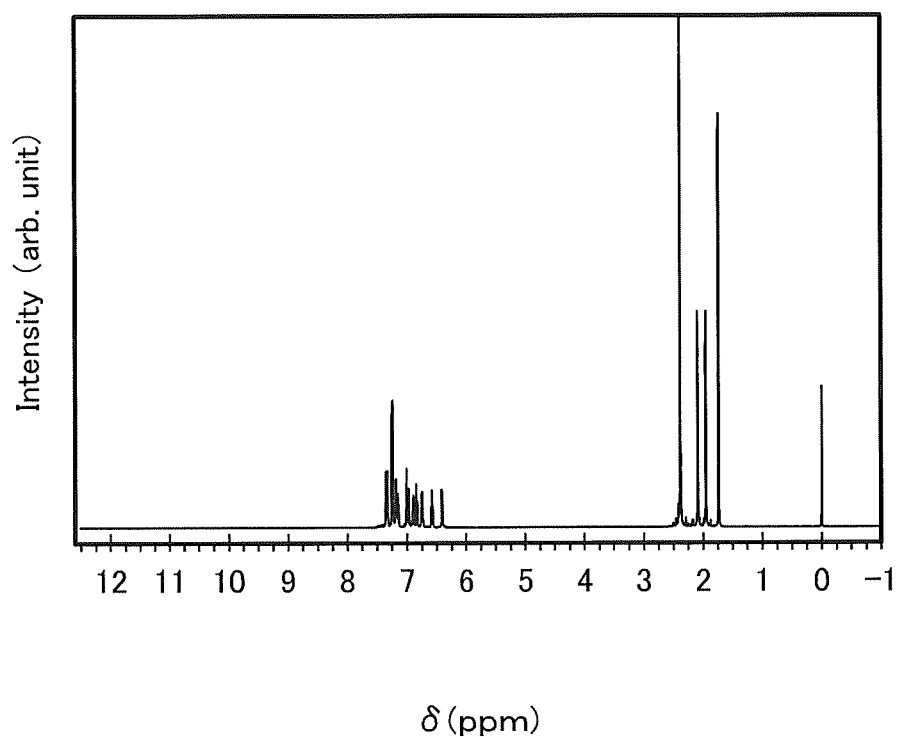
FIG. 38 shows $^1$H-NMR spectrum of [Ir(mpptz-tetmb)$_3$].

The protons (¹H) of the yellow solid that was obtained in Step 3 was measured by nuclear magnetic resonance (NMR). The obtained values are shown below. FIG. 38 shows ¹H-NMR spectrum. The results reveal that [Ir(mpptz-tetmb)₃] was obtained.

¹H-NMR δ (CDCl₃): 1.95 (s, 9H), 2.09 (s, 9H), 2.38 (s, 27H), 6.41 (d, 3H), 6.58 (t, 3H), 6.75 (t, 3H), 6.84 (d, 3H), 6.90 (t, 3H), 6.98 (d, 3H), 7.01 (s, 3H), 7.14-7.20 (m, 6H), 7.24 (s, 6H), 7.34 (d, 6H).

Figure 39:
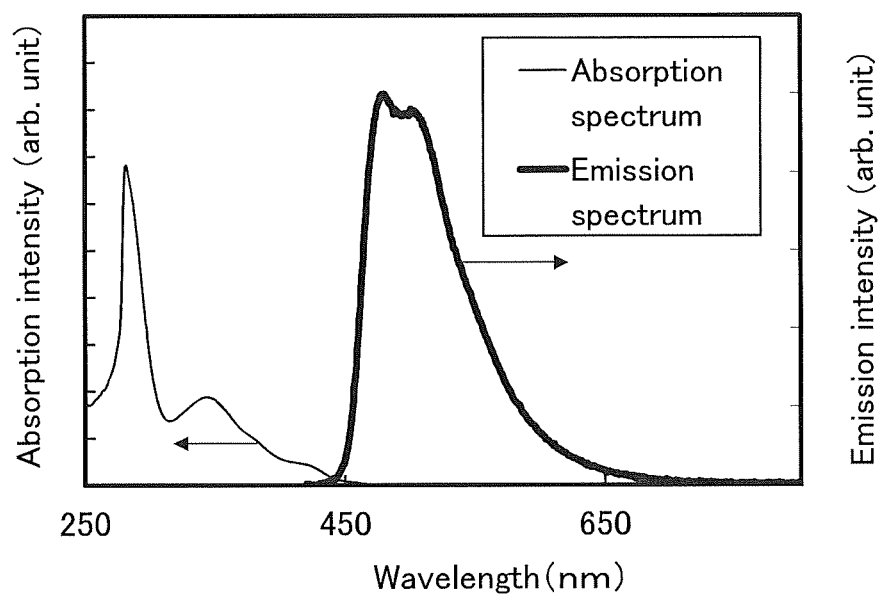
FIG. 39 shows the emission spectrum and the absorption spectrum of [Ir(mpptz-tetmb)$_3$].

Next, an ultraviolet-visible absorption spectrum (hereinafter, simply referred to as absorption spectrum) and an emission spectrum of a dichloromethane solution of [Ir(mpptz-tetmb)₃] were measured. The measurement of the absorption spectrum was conducted at room temperature, for which an ultraviolet and visible spectrophotometer (V550 type manufactured by JASCO Corporation) was used and the dichloromethane solution (0.0100 mmol/L) was put in a quartz cell. In addition, the measurement of the emission spectrum was performed at room temperature in such a manner that an absolute PL quantum yield measurement system (C11347-01 manufactured by Hamamatsu Photonics K.K.) was used, and the deoxidized dichloromethane solution (0.0100 mmol/L) was sealed in a quartz cell under a nitrogen atmosphere in a glove box (LABstar M13 (1250/780) manufactured by Bright Co., Ltd.). FIG. 39 shows measurement results of the absorption spectrum and the emission spectrum. The horizontal axis represents wavelength and the vertical axes represent absorption intensity and emission intensity. Note that the absorption spectrum in FIG. 39 is a result obtained by subtraction of a measured absorption spectrum of only dichloromethane that was put in a quartz cell from the measured absorption spectrum of the dichloromethane solution (0.0100 mmol/L) in a quartz cell.

EXAMPLE 4

In this example, light-emitting elements 4 and 5 of one embodiment of the present invention, which are described in Embodiment, and a comparative light-emitting element 3 are described. Structural formulae of organic compounds used in the light-emitting elements 4 and 5 and the comparative light-emitting element 3 are shown below.

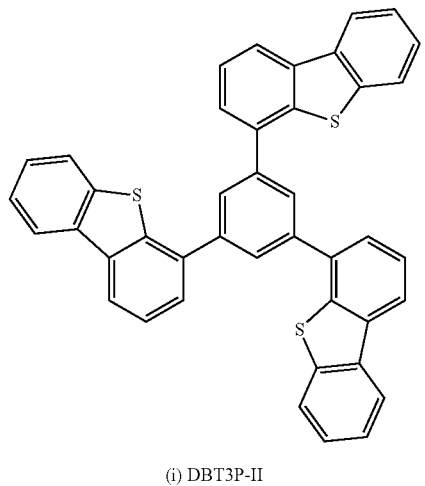

(i) DBT3P-II

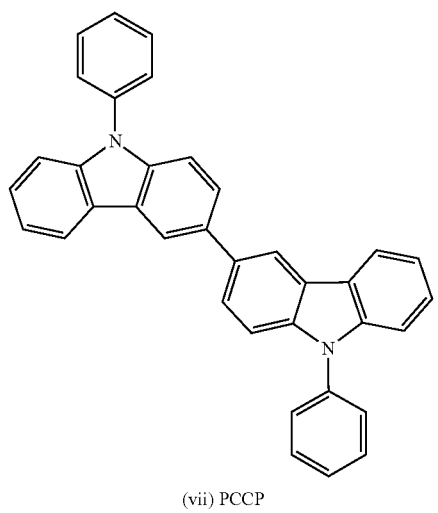

(vii) PCCP

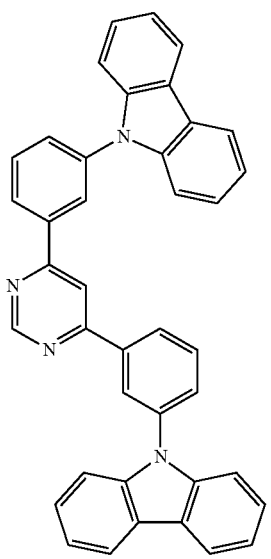

(iv) 4,6mCzP2Pm

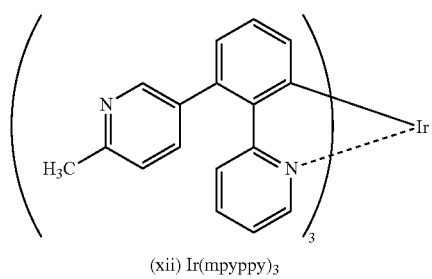

(xii) Ir(mpyppy)₃

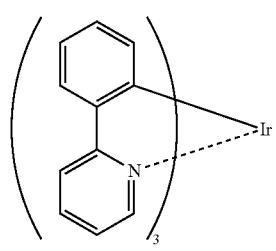

(xiv) [Ir(ppy)₃]

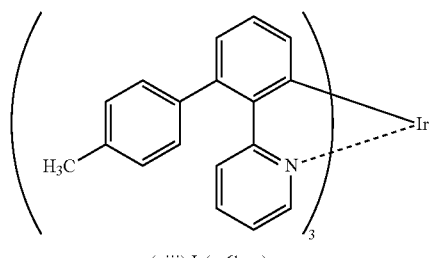

(xiii) Ir(m6bpy)₃

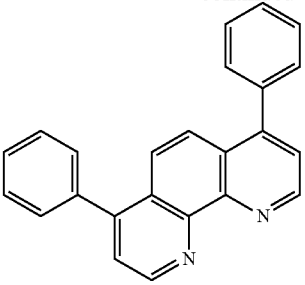

(vi) BPhen (Fabrication Method of Light-Emitting Element 4)

First, indium tin oxide containing silicon oxide (ITSO) was deposited over a glass substrate by a sputtering method to form the first electrode 101. The thickness of the first electrode 101 was set to 70 nm and the area of the electrode was set to 4 mm² (2 mm×2 mm).

Next, in pretreatment for forming the light-emitting element over the substrate, a surface of the substrate was washed with water and baked at 200° C. for 1 hour, and then UV ozone treatment was performed for 370 seconds.

After that, the substrate was transferred into a vacuum evaporation apparatus whose pressure was reduced to approximately $10^{-4}$ Pa, vacuum baking at 170° C. for 30 minutes was performed in a heating chamber in the vacuum evaporation apparatus, and then the substrate was cooled down for approximately 30 minutes.

Then, the substrate over which the first electrode 101 was formed was fixed to a substrate holder provided in the vacuum evaporation apparatus so that the surface on which the first electrode 101 was formed faced downward. After that, on the first electrode 101, 1,3,5-tri-(4-dibenzothiophenyl)-benzene (abbreviation: DBT3P-II) represented by Structural formula (i) and molybdenum(VI) oxide were deposited by co-evaporation to a thickness of 40 nm at a weight ratio of 2:1 (=DBT3P-II: molybdenum oxide) by an evaporation method using resistance heating, so that the hole-injection layer 111 was formed.

Next, 3,3'-bis(9-phenyl-9H-carbazole) (abbreviation: PCCP) represented by Structural formula (vii) was deposited by evaporation to a thickness of 20 nm over the hole-injection layer 111 to form the hole-transport layer 112.

Next, 9,9'-(pyrimidine-4,6-diyldi-3,1-phenylene)bis(9H-carbazole) (abbreviation: 4,6mCzP2Pm) represented by Structural formula (iv), PCCP, and tris[3-(2-methylpyridin-5-yl)-2-(2-pyridinyl)-κN)phenyl-κC]iridium(III) (abbreviation: [Ir(mpyppy)₃]) were deposited by co-evaporation to a thickness of 20 nm at a weight ratio of 0.5:0.5:0.1 (=4,6mCzP2Pm:PCCP:[Ir(mpyppy)₃]), and then 4,6mCzP2Pm, PCCP, and [Ir(mpyppy)₃] were deposited by co-evaporation to a thickness of 20 nm at a weight ratio of 0.8:0.2:0.1 (=4,6mCzP2Pm:PCCP:[Ir(mpyppy)₃]), so that the light-emitting layer 113 was formed.

Then, 4,6mCzP2Pm was deposited by evaporation to a thickness of 20 nm, and bathophenanthroline (abbreviation: BPhen) represented by Structural formula (vi) was deposited by evaporation to a thickness of 10 nm over the light-emitting layer 113 to form the electron-transport layer 114.

After the formation of the electron-transport layer 114, lithium fluoride (LiF) was deposited by evaporation to a thickness of 1 nm to form the electron-injection layer 115. Then, aluminum was deposited by evaporation to a thickness of 200 nm to form the second electrode 102. Through the above-described steps, the light-emitting element 4 of this example was fabricated.
(Fabrication Method of Light-Emitting Element 5)

The light-emitting element 5 was fabricated in the same manner as the light-emitting element 4 except that tris[4'-methyl-2-(2-pyridinyl-κN)(1,1'-biphenyl)-3-yl-κC]iridium (III) (abbreviation: [Ir(m6bpy)$_3$]) represented by Structure formula (xiii) was used instead of [Ir(mpyppy)$_3$] of the light-emitting element 4.
(Fabrication Method of Comparative Light-Emitting Element 3)

The comparative light-emitting element 3 was fabricated in the same manner as the light-emitting element 4 except that tris(2-phenylpyridinato-N,C$^2$')iridium(III) (abbreviation: [Ir(ppy)$_3$]) was used instead of [Ir(mpyppy)$_3$] of the light-emitting element 4.

The element structures of the light-emitting elements 4 and 5 and the comparative light-emitting element 3 are shown in the following tables.

Each of the light-emitting elements 4 and 5 and the comparative light-emitting element 3 was sealed using a glass substrate in a glove box containing a nitrogen atmosphere so as not to be exposed to the air (specifically, a sealing material was applied to surround the element, UV treatment and heat treatment at 80° C. for 1 hour were performed at the time of sealing). Then, initial characteristics of these light-emitting element were measured. The measurement was carried out at room temperature (under an atmosphere where a temperature was maintained at 25° C.).

Figure 40:
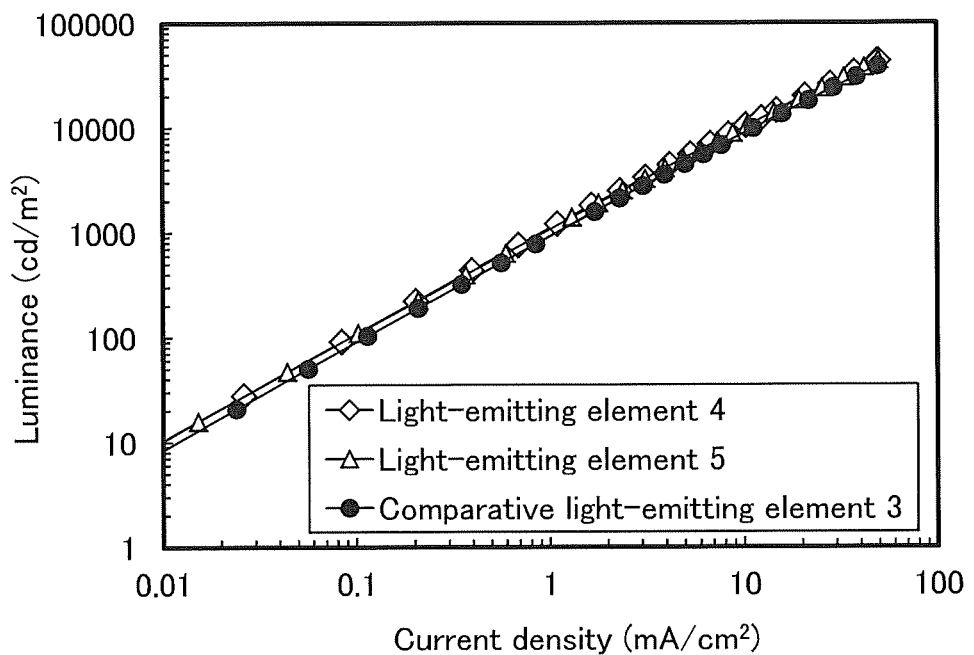
FIG. 40 shows the luminance-current density characteristics of light-emitting elements 4 and 5 and a comparative light-emitting element 3.
Figure 41:
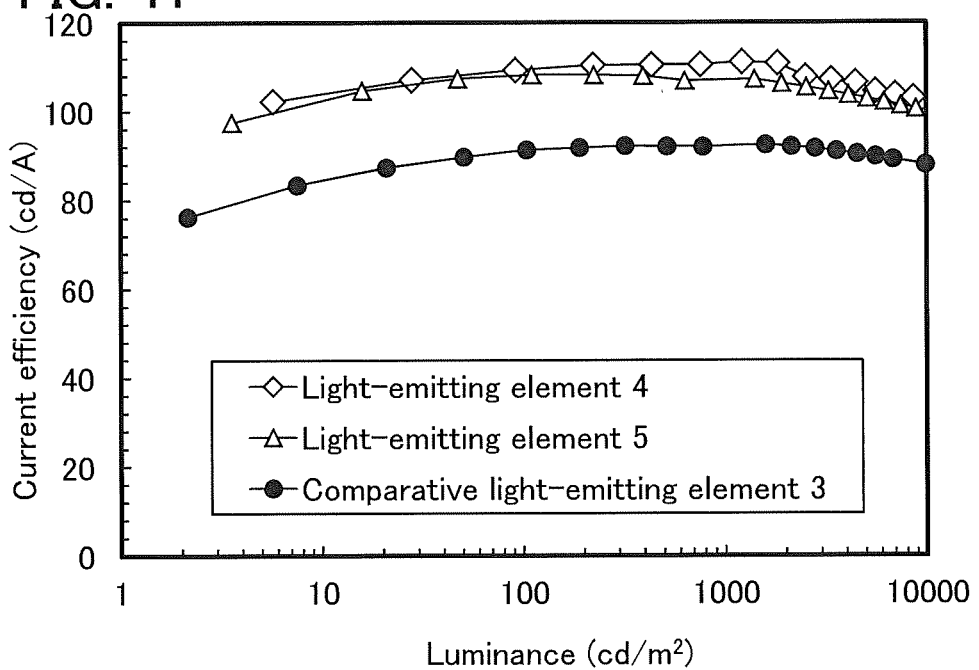
FIG. 41 shows the current efficiency-luminance characteristics of the light-emitting elements 4 and 5 and the comparative light-emitting element 3.
Figure 42:
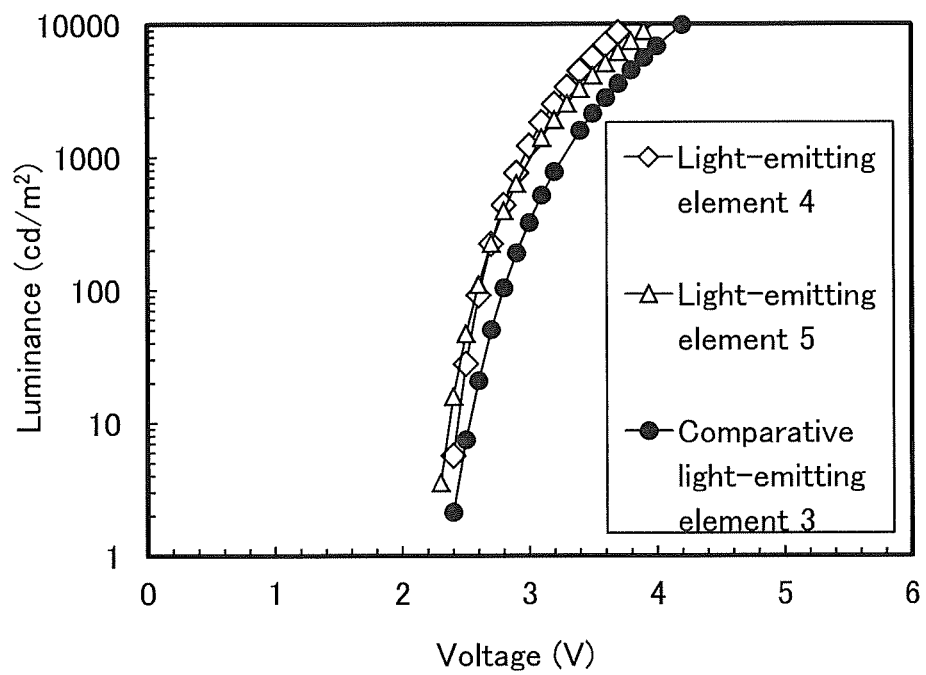
FIG. 42 shows the luminance-voltage characteristics of the light-emitting elements 4 and 5 and the comparative light-emitting element 3.
Figure 43:
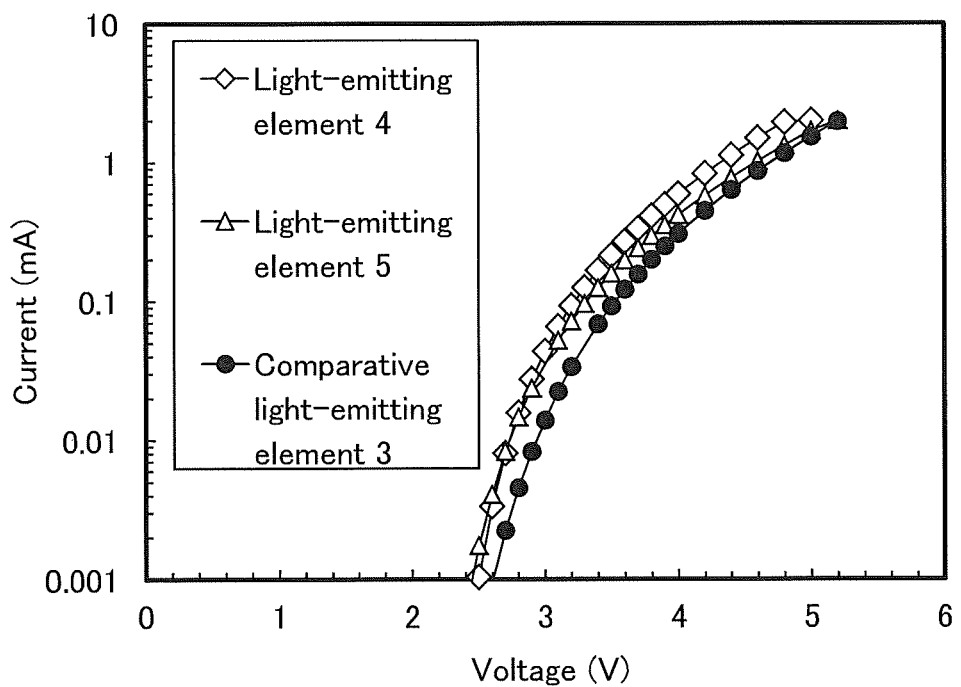
FIG. 43 shows the current-voltage characteristic of the light-emitting elements 4 and 5 and the comparative light-emitting element 3.
Figure 44:
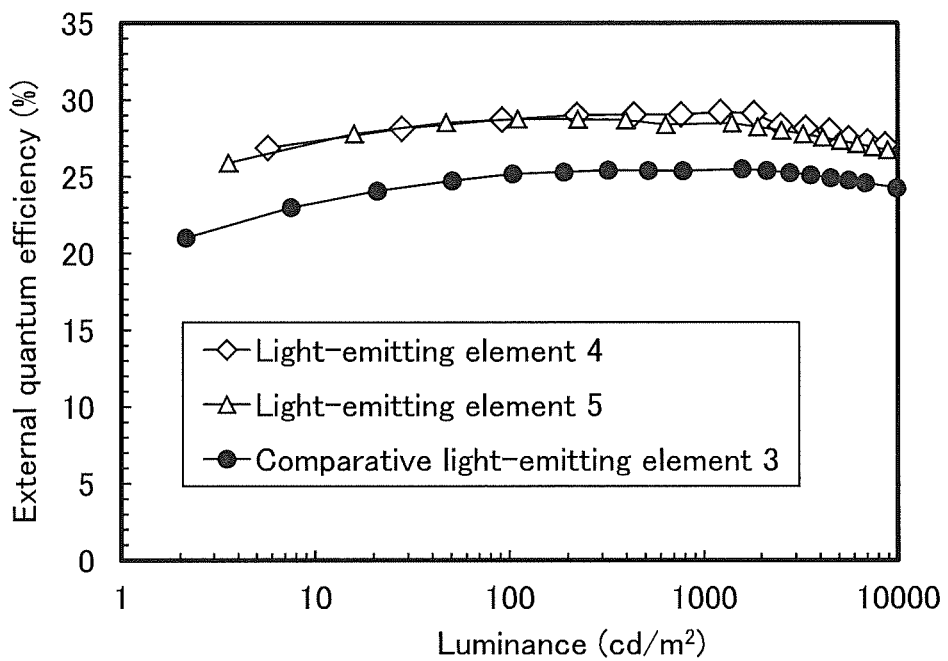
FIG. 44 shows the external quantum efficiency-luminance characteristics of the light-emitting elements 4 and 5 and the comparative light-emitting element 3.

FIG. 40 shows the luminance-current density characteristics of the light-emitting elements 4 and 5 and the comparative light-emitting element 3. FIG. 41 shows the current efficiency-luminance characteristics of the light-emitting elements 4 and 5 and the comparative light-emitting element 3. FIG. 42 shows the luminance-voltage characteristics of the light-emitting elements 4 and 5 and the comparative light-emitting element 3. FIG. 43 shows the current-voltage characteristics of the light-emitting elements 4 and 5 and the comparative light-emitting element 3. FIG. 44 shows the

TABLE 11

| | | Light-emitting Element 4 | | | | |
|---|---|---|---|---|---|---|
| | | Light-emitting Layer | | | | |
| Hole-injection Layer | Hole-transport Layer | First Light-emitting Layer | Second Light-emitting Layer | Electron-transport Layer | | Electron-injection Layer |
| DBT3P-II: MoOx (2:1) | PCCP | 4,6CzP2Pm: PCCP: Ir(mpyppy)$_3$ (0.5:0.5:0.1) | 4,6CzP2Pm: PCCP: Ir(mpyppy)$_3$ (0.8:0.2:0.1) | 4,6CzP2Pm | BPhen | LiF |
| 40 nm | 20 nm | 20 nm | 20 nm | 20 nm | 10 nm | 1 nm |

TABLE 12

| | | Light-emitting Element 5 | | | | |
|---|---|---|---|---|---|---|
| | | Light-emitting Layer | | | | |
| Hole-injection Layer | Hole-transport Layer | First Light-emitting Layer | Second Light-emitting Layer | Electron-transport Layer | | Electron-injection Layer |
| DBT3P-II: MoOx (2:1) | PCCP | 4,6CzP2Pm: PCCP: Ir(m6bpy)$_3$ (0.5:0.5:0.1) | 4,6CzP2Pm: PCCP: Ir(m6bpy)$_3$ (0.8:0.2:0.1) | 4,6CzP2Pm | BPhen | LiF |
| 40 nm | 20 nm | 20 nm | 20 nm | 20 nm | 10 nm | 1 nm |

TABLE 13

Figure 45:
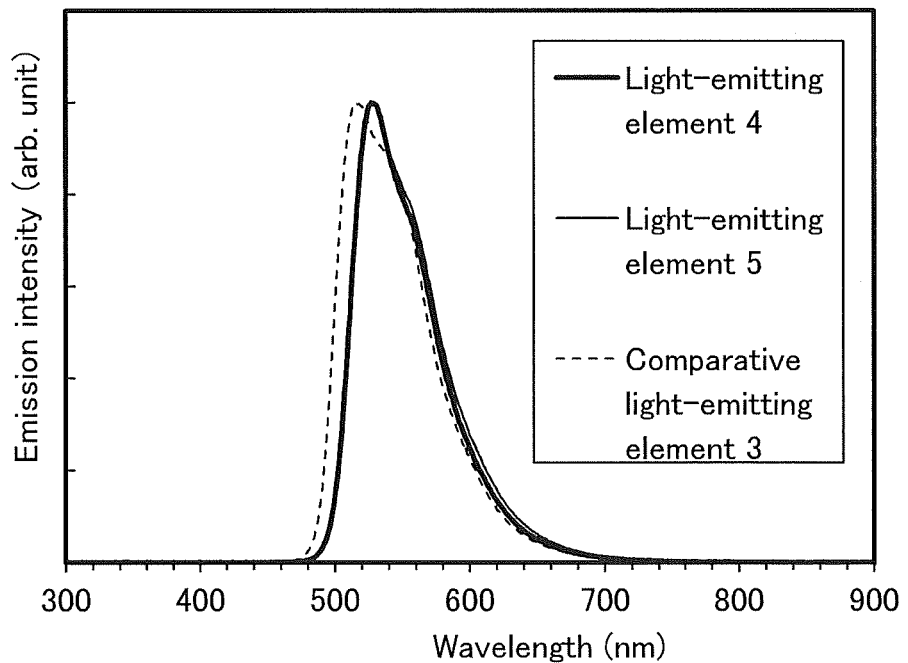
FIG. 45 shows the emission spectrum of the light-emitting elements 4 and 5 and the comparative light-emitting element 3.

| | | Comparative Light-emitting Element 3 | | | | |
|---|---|---|---|---|---|---|
| | | Light-emitting Layer | | | | |
| Hole-injection Layer | Hole-transport Layer | First Light-emitting Layer | Second Light-emitting Layer | Electron-transport Layer | | Electron-injection Layer |
| DBT3P-II: MoOx (2:1) | PCCP | 4,6CzP2Pm: PCCP: Ir(ppy)$_3$ (0.5:0.5:0.1) | 4,6CzP2Pm: PCCP: Ir(ppy)$_3$ (0.8:0.2:0.1) | 4,6CzP2Pm | BPhen | LiF |
| 40 nm | 20 nm | 20 nm | 20 nm | 20 nm | 10 nm | 1 nm | external quantum efficiency-luminance characteristics of the light-emitting elements 4 and 5 and the comparative light-emitting element 3. FIG. 45 shows the emission spectrum of the light-emitting elements 4 and 5 and the comparative light-emitting element 3.

TABLE 14

| | Voltage (V) | Current (mA) | Current Density (mA/cm$^2$) | Current Efficiency (cd/A) | External Quantum Efficiency (%) |
|---|---|---|---|---|---|
| Light-emitting Element 4 | 3.0 | 0.044 | 1.1 | 111.1 | 29.2 |
| Light-emitting Element 5 | 2.9 | 0.024 | 0.6 | 106.9 | 28.4 |
| Comparative Light-emitting Element 3 | 3.2 | 0.034 | 0.8 | 92.1 | 25.4 |

The results shown in FIG. 40, FIG. 41, FIG. 42, FIG. 43, FIG. 44, FIG. 45, and Table 14 indicate that the external quantum efficiencies at around 1000 cd/m$^2$ of the light-emitting elements 4 and 5 and the comparative light-emitting element 3 were 29.2%, 28.4%, and 25.4%, respectively.

The parameter of planarity (A×B/C$^2$) of [Ir(mpyppy)$_3$] used in the light-emitting element 4 was calculated as 5.7, that of [Ir(m6bpy)$_3$] used in the light-emitting element 5 was calculated to be 5.8, and that of [Ir(ppy)$_3$] used in the comparative light-emitting element 3 was calculated as 1.9. In this manner, the light-emitting element formed using the tris iridium complex with high parameter of planarity can exhibit extremely high efficiency.

EXAMPLE 5

Synthesis Example 1

In this example, a method for synthesizing tris[3-(2-methylpyridin-5-yl)-2-(2-pyridinyl)-κN)phenyl-κC]iridium (III) (abbreviation: [Ir(mpyppy)$_3$]) that is the iridium complex used in Example 4 is described. The structure formula of [Ir(mpyppy)$_3$] is shown below.

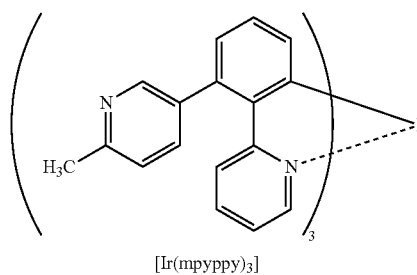

[Ir(mpyppy)$_3$]

Step 1: Synthesis of 2-[2-(2-methyl-5-pyridyl)phenyl]pyridine (Abbreviation: Hmpyppy)

Into a 200 mL three-neck flask were put 2.3 g (15 mmol) of 2-phenylpyridine, 2.5 g (15 mmol) of 5-bromo-2-methylpyridin, 0.38 g (1.5 mmol) of triphenylphosphine, 8.0 g (58 mmol) of potassium carbonate, and 0.18 g (0.36 mmol) of benzeneruthenium(II)chloride dimer. The atmosphere in the flask was replaced with nitrogen, and the mixture was degassed while being stirred under reduced pressure. After the degassing, 58 mL of 1-methyl-2-pyrrolidone (abbreviation: NMP) was added, and the mixture was stirred under a nitrogen stream at 120° C. for 7 hours. Toluene was added to the obtained reacted solution, and the mixture was subjected to suction filtration through Celite. The obtained filtrate was concentrated to give an oily substance. The obtained oily substance was purified by silica column chromatography. As the developing solvent, a 5:1 hexane-ethyl acetate mixed solvent was used. The resulting fraction was concentrated to give 2.5 g of a yellow oily substance in a yield of 69%. The obtained yellow oily substance was identified as 2-[2-(2-methyl-5-pyridyl)phenyl]pyridine (abbreviation: Hmpyppy) by nuclear magnetic resonance (NMR). A scheme of the synthesis of Step 1 is shown below.

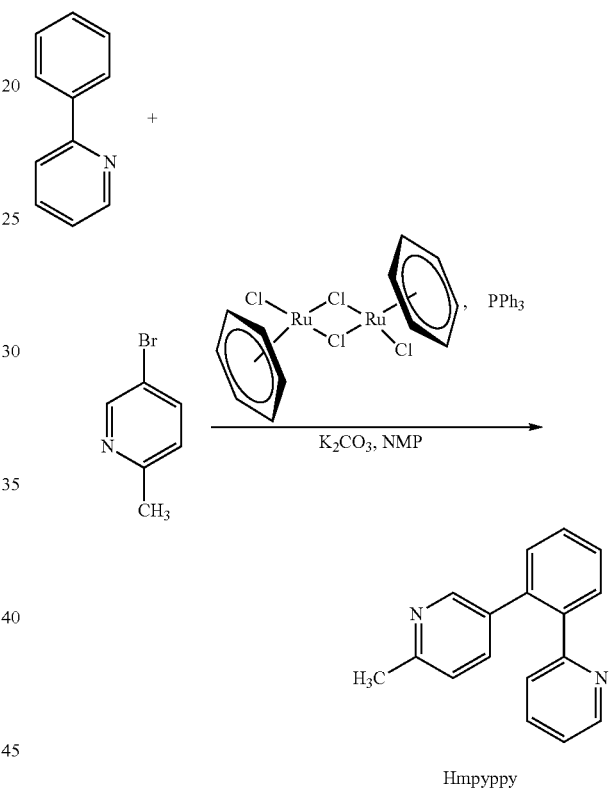

Step 2: Synthesis of di-μ-chloro-tetrakis[3-(2-methylpyridin-5-yl)-2-(2-pyridinyl-κN)phenyl-κC] iridium(III) (Abbreviation: [Ir(mpyppy)$_2$Cl]$_2$)

Into a 100-mL round-bottom flask were put 2.4 g (10 mmol) of 2-[2-(2-methyl-5-pyridyl)phenyl]pyridine (abbreviation: Hmpyppy) synthesized in Step 1, 1.3 g (4.5 mmol) of iridium chloride monohydrate, 30 mL of 2-ethoxyethanol, and 10 mL of water, and the atmosphere in the flask was replaced with argon. This reaction container was subjected to irradiation with microwaves (2.45 GHz, 100 W) for 3 hour to cause a reaction. After the reaction, the reaction solution was subjected to suction filtration to give 1.7 g of a yellow solid in a yield of 53%. A scheme of the synthesis of Step 2 is shown below.

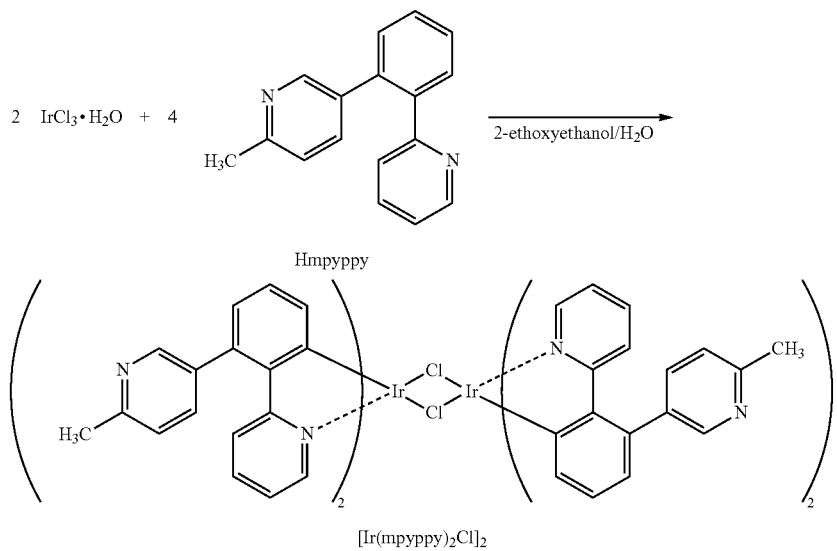

Step 3: Synthesis of tris[3-(2-methylpyridin-5-yl)-2-(2-pyridinyl)-κN)phenyl-κC]iridium(III) (Abbreviation: [Ir(mpyppy)₃])

Into a 200 mL three-neck flask were put 1.7 g (1.2 mmol) of [Ir(mpyppy)₂Cl]₂ synthesized in Step 2, 1.5 g (6.1 mmol) of Hmpyppy, 1.7 g (12 mmol) of potassium carbonate, and 10 g of phenol, and the mixture was heated under a nitrogen stream at 190° C. for 31 hours. Methanol was added to the reaction mixture, and the mixture was irradiated with ultrasonic waves and then suction-filtered to give a yellow solid. Dichloromethane and water were added so that the obtained solid was dissolved, and extraction was performed. Then, the extracted solution was concentrated, dichloromethane was added to the obtained solid, and the mixture was filtered through a filter aid in which Celite, neutral silica gel, and Celite were stacked in this order. Furthermore, the mixture was washed with ethyl acetate, and the obtained filtrate was concentrated to give a solid. The obtained solid was recrystallized from ethyl acetate to give 0.45 g of a yellow solid in a yield of 20%. Then, 0.44 g of the obtained solid was purified by a train sublimation method. The purification by sublimation was performed by heating at 320° C. under a pressure of 2.6 Pa with an argon flow rate of 5 mL/min for 16 hours. After the purification by sublimation, 0.35 g of a yellow solid was obtained in a yield of 80%. The synthesis scheme of Step 3 is shown below.

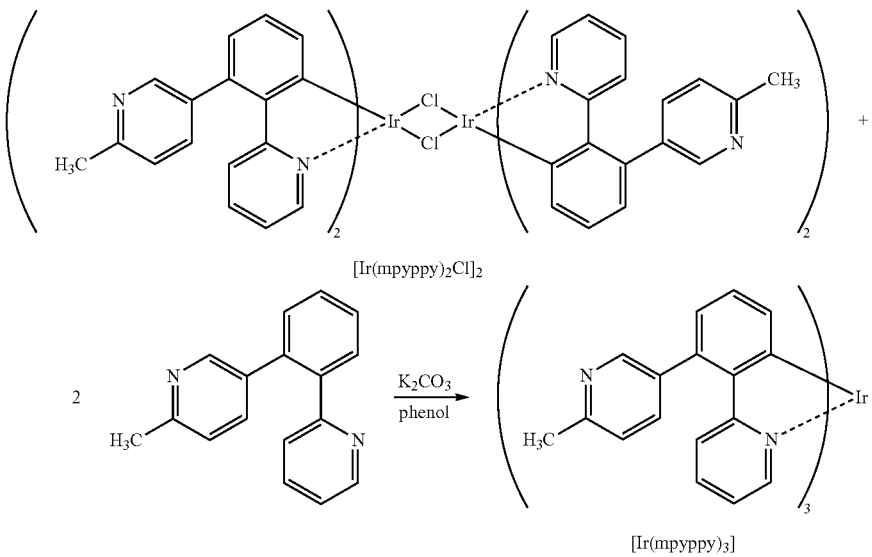

Figure 46A:
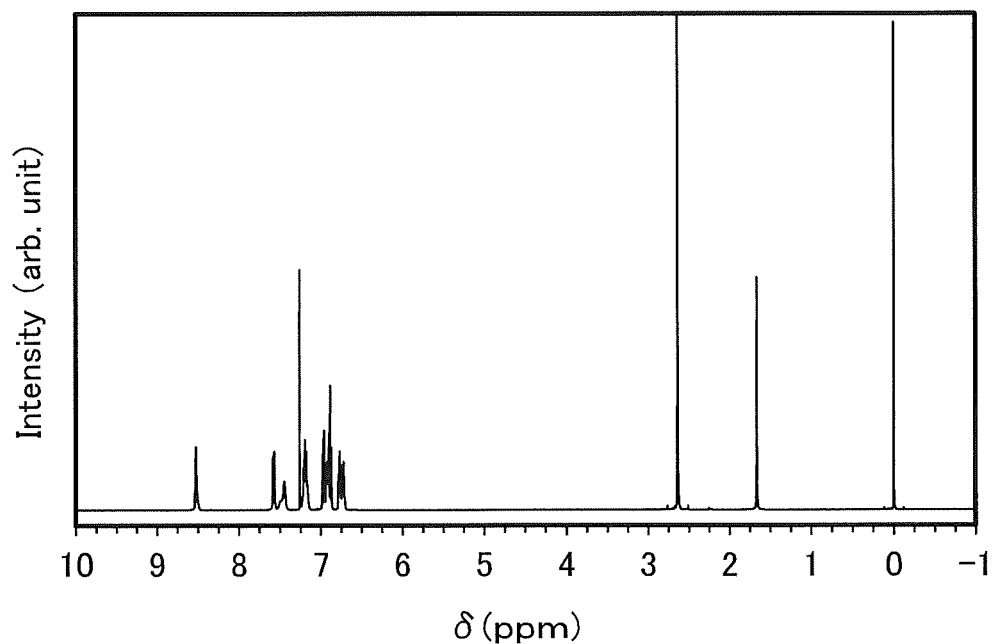
FIGS. 46A and 46B shows $^1$H-NMR spectrum of [Ir(mpyppy)$_3$].
Figure 46B:
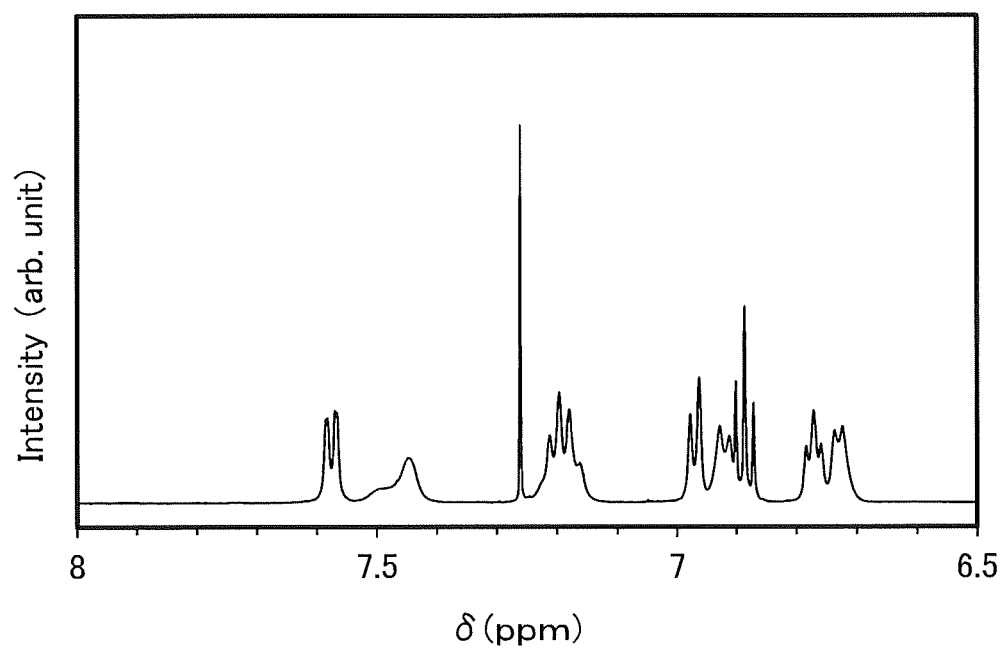

The protons ($^1$H) of the yellow solid that was obtained in Step 3 was measured by nuclear magnetic resonance (NMR). The obtained values are shown below. In addition, $^1$H NMR charts are shown in FIGS. 46A and 46B. The results revealed that [Ir(mpyppy)₃] was obtained.

$^1$H-NMR δ (CDCl₃): 2.64 (s, 9H), 6.72-6.78 (m, 6H), 6.87-6.98 (m, 9H), 7.16-7.21 (m, 6H), 7.45 (br, 3H), 7.58 (d, 3H), 8.53 (s, 3H).

Figure 47:
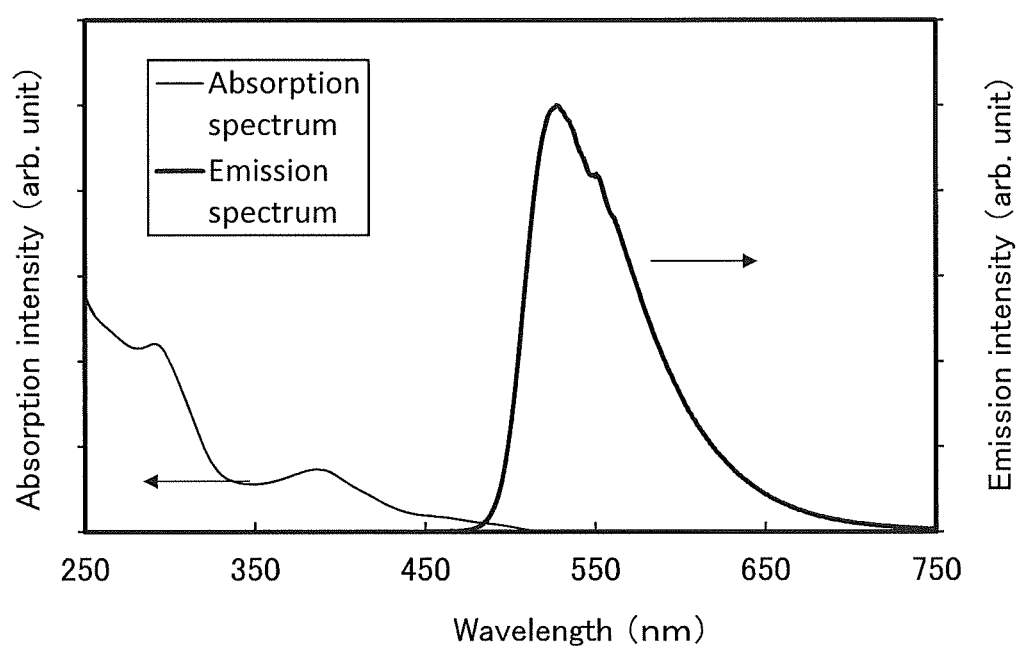
FIG. 47 shows the emission spectrum and the absorption spectrum of [Ir(mpyppy)$_3$].

Next, an ultraviolet-visible absorption spectrum (hereinafter, simply referred to as absorption spectrum) and an emission spectrum of a dichloromethane solution of [Ir(mpyppy)$_3$] were measured. The measurement of the absorption spectrum was conducted at room temperature, for which an ultraviolet and visible spectrophotometer (V550 type manufactured by JASCO Corporation) was used and the dichloromethane solution (0.0093 mmol/L) was put in a quartz cell. In addition, the measurement of the emission spectrum was performed at room temperature in such a manner that an absolute PL quantum yield measurement system (C11347-01 manufactured by Hamamatsu Photonics K.K.) was used, and the deoxidized dichloromethane solution (0.0093 mmol/L) was sealed in a quartz cell under a nitrogen atmosphere in a glove box (LABstar M13 (1250/780) manufactured by Bright Co., Ltd.). FIG. 47 shows measurement results of the absorption spectrum and the emission spectrum. The horizontal axis represents wavelength and the vertical axes represent absorption intensity and emission intensity. Note that the absorption spectrum in FIG. 47 is a result obtained by subtraction of a measured absorption spectrum of only dichloromethane that was put in a quartz cell from the measured absorption spectrum of the dichloromethane solution (0.0093 mmol/L) in a quartz cell.

As shown in FIG. 47, the iridium complex, [Ir(mpyppy)$_3$], had an emission peak at 528 nm, and green light emitted from dichloromethane was observed.

Next, [Ir(mpyppy)$_3$] obtained in this example was analyzed by liquid chromatography mass spectrometry (LC/MS).

In the analysis by LC-MS, liquid chromatography (LC) separation was carried out with UltiMate 3000 produced by Thermo Fisher Scientific K.K., and the MS analysis was carried out with Q Exactive produced by Thermo Fisher Scientific K.K.

In the LC separation, a given column was used at a column temperature of 40° C., an appropriate solvent was selected, the sample was prepared by dissolving [[Ir(mpyppy)$_3$] in an organic solvent at an arbitrary concentration, and the injection amount was 5.0 μL.

A component with m/z of 929.29, which is an ion derived from [Ir(mpyppy)$_3$], was subjected to the MS$^2$ analysis by a Targeted-MS$^2$ method. For setting of the Targeted-MS$^2$, the mass range of a target ion was set to m/z=929.29±2.0 (isolation window=4) and detection was performed in a positive mode. Measurement was performed with energy (normalized collision energy: NCE) for accelerating a target ion in a collision cell set to 20. The obtained MS spectrum is shown in FIG. 48.

Figure 48:
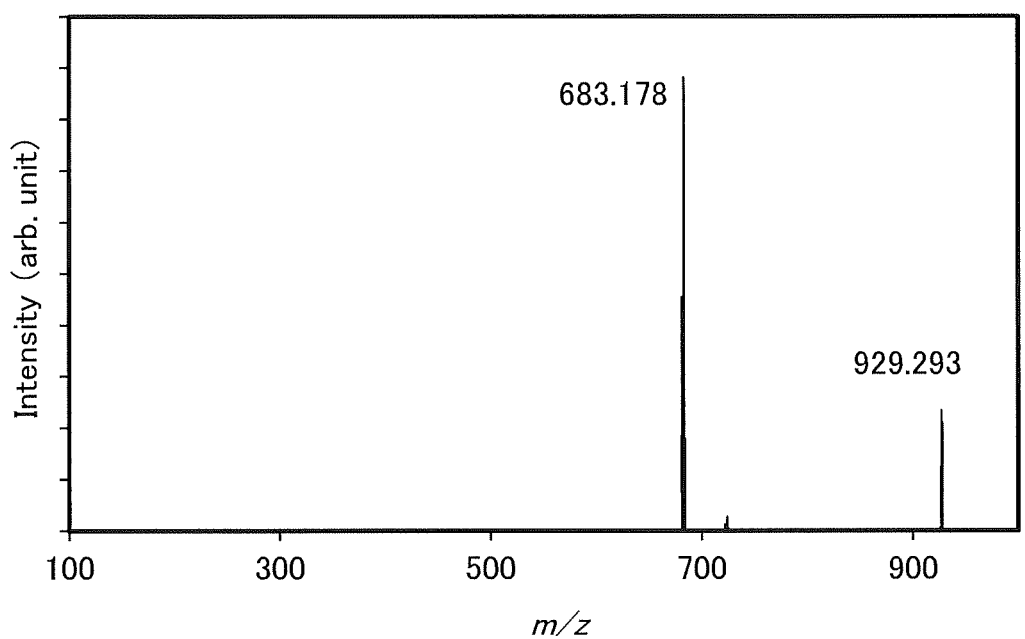
FIG. 48 shows the LC-MS spectrum of [Ir(mpyppy)$_3$].

FIG. 48 shows that product ions of [Ir(mpyppy)$_3$] are mainly detected around m/z=683. The results in FIG. 48 show characteristics derived from [Ir(mpyppy)$_3$] and therefore can be regarded as important data for identifying [Ir(mpyppy)$_3$] contained in a mixture.

It can be presumed that the product ion around m/z=683 is a cation in a state where Hmpyppy that is a ligand of [Ir(mpyppy)$_3$] is eliminated. This suggests that [Ir(mpyppy)$_3$] contains Hmpyppy.

EXAMPLE 6

Synthesis example 2

In this example, a method for synthesizing tris[4'-methyl-2-(2-pyridinyl-κN)(1,1'-biphenyl)-3-yl-κC]iridium(III) (abbreviation: [Ir(m6bpy)$_3$]) that is the organometallic complex used in Example 4 is described. The structure formula of [Ir(m6bpy)$_3$] is shown below.

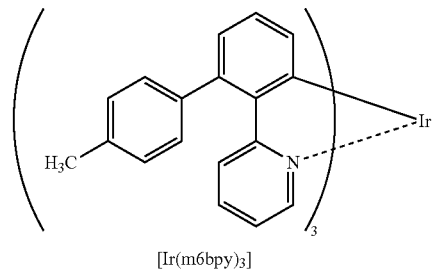

[Ir(m6bpy)$_3$]

Step 1: Synthesis of 4'-methyl-2-(1,1'-biphenyl)-2-yl-pyridin (Abbreviation: Hm6bpy)

Into a 200 mL three-neck flask were put 15 g (97 mmol) of 2-phenylpyridine, 13 g (77 mmol) of 4-bromotoluene, 2.5 g (9.7 mmol) of triphenylphosphine, 53 g (386 mmol) of potassium carbonate, and 1.2 g (2.4 mmol) of benzeneruthenium(II)chloride dimer. The atmosphere in the flask was replaced with nitrogen, and the mixture was degassed while being stirred under reduced pressure. After the degassing, 100 mL of 1-methyl-2-pyrrolidone (abbreviation: NMP) was added, and the mixture was stirred under a nitrogen stream at 120° C. for 18 hours. After the predetermined period of time, extraction was performed with ethyl acetate. After that, purification was performed by silica column chromatography. As the developing solvent, a 10:1 hexane-ethyl acetate mixed solvent was used. The obtained fraction was concentrated to give 11 g of a green oily substance in a yield of 59%. The obtained green oily substance was identified as 4'-methyl-2-(1,1'-biphenyl)-2-yl-pyridin (abbreviation: Hm6bpy) by nuclear magnetic resonance (NMR). The synthesis scheme of Step 1 is shown below.

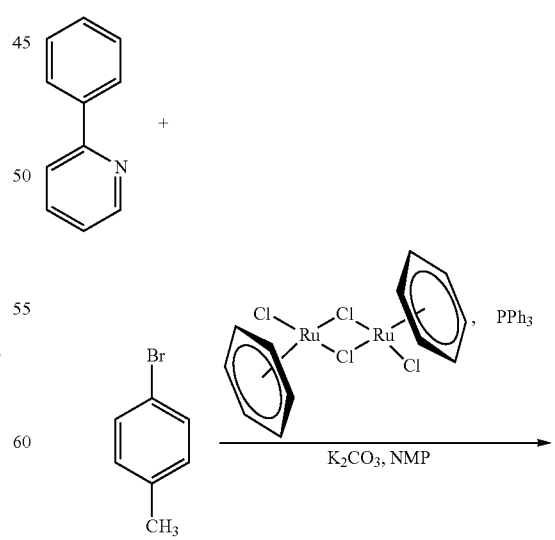

Step 2: Synthesis of di-μ-chloro-tetrakis[4'-methyl-2-(2-pyridinyl-κN)(1,1'-biphenyl)-3-yl-κC]iridium(III) (Abbreviation: [Ir(m6bpy)₂Cl]₂)

Into a 100-mL round-bottom flask were put 5.0 g (20 mmol) of 4'-methyl-2-(1,1'-biphenyl)-2-yl-pyridin (abbreviation: Hm6bpy) synthesized in Step 1, 2.9 g (9.6 mmol) of iridium chloride monohydrate, 35 mL of 2-ethoxyethanol, and 12 mL of water, and the atmosphere in the flask was replaced with argon. This reaction container was subjected to irradiation with microwaves (2.45 GHz, 100 W) for 3 hour to cause a reaction. After the reaction, the reaction solution was subjected to suction filtration to give 3.8 g of a yellow solid in a yield of 55%. The synthesis scheme of Step 2 is shown below.

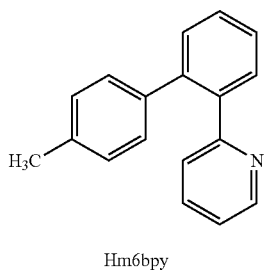

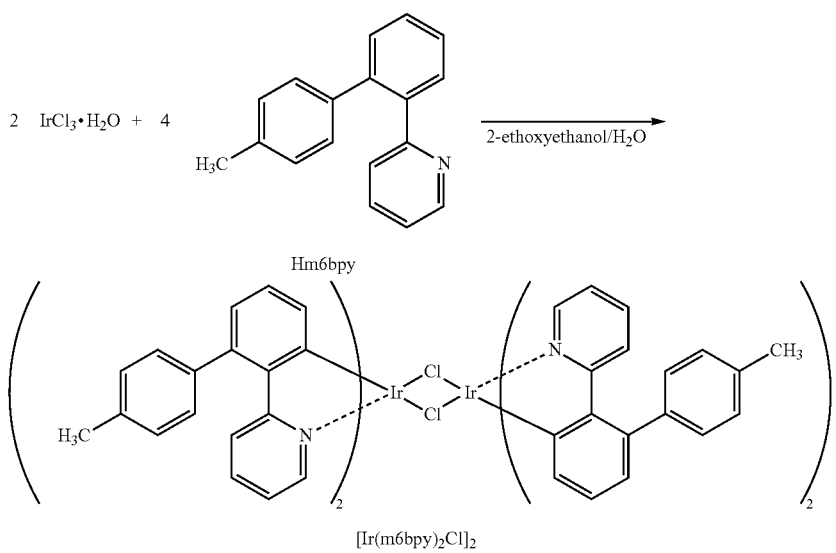

Step 3: Synthesis of tris[4'-methyl-2-(2-pyridinyl-κN)(1,1'-biphenyl)-3-yl-κC]iridium(III) (Abbreviation: [Ir(m6bpy)₃])

Into a flask were put 3.8 g (2.6 mmol) of [Ir(m6bpy)₂Cl]₂ synthesized in Step 2, 1.9 g (7.9 mmol) of Hm6bpy, 3.6 g (26 mmol) of potassium carbonate, and 15 g of phenol, and the mixture was heated under a nitrogen stream at 190° C. for 3.5 hours. Methanol was added to the reaction mixture, and the mixture was irradiated with ultrasonic waves and then suction-filtered to give a yellow solid. The obtained yellow solid was washed with water and then washed with ethanol. Dichloromethane was added to the obtained solid, and the mixture was filtered through a filter aid in which Celite, neutral silica gel, and Celite were stacked in this order. The obtained filtrate was concentrated to give a solid. Ethanol was added to the obtained solid, and the mixture was irradiated with ultrasonic waves and then suction filtered to give 4.7 g of a yellow solid in a yield of 98%. Then, 2.6 g of the obtained solid was purified by a train sublimation method. The purification by sublimation was conducted by heating at 290° C. under a pressure of 2.1 Pa with a flow rate of argon gas of 10.7 mL/min for 21 hours. After the purification by sublimation, 1.3 g of a yellow solid was obtained in a yield of 50%. The synthesis scheme of Step 3 is shown below.

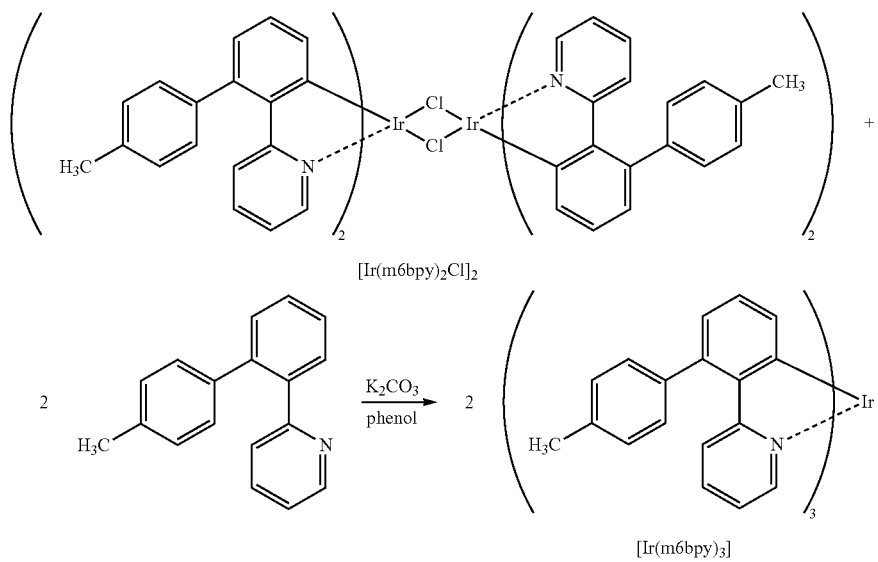

[Ir(m6bpy)₃]

Figure 49A:
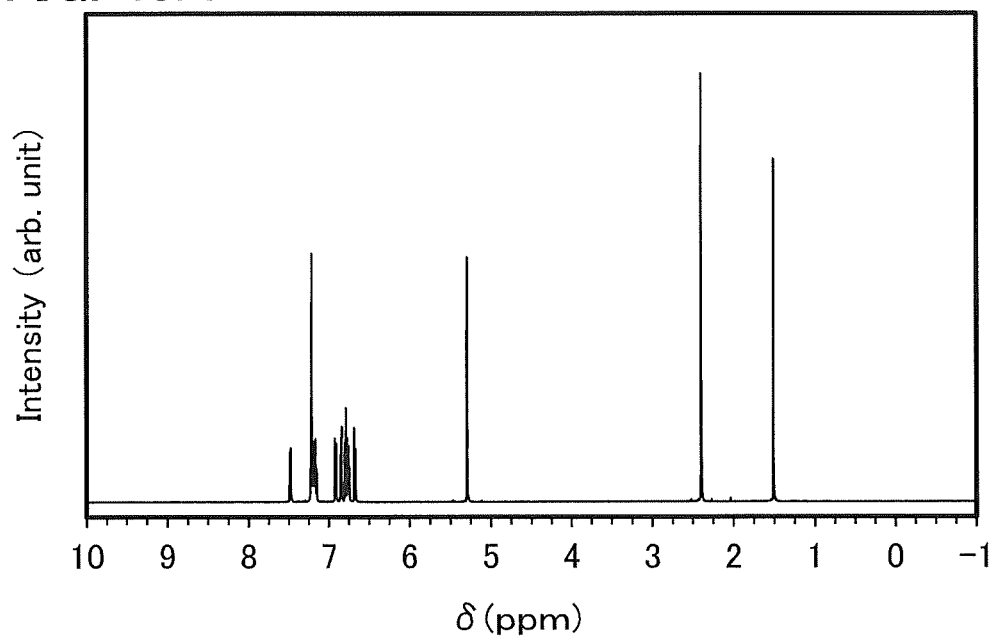
FIGS. 49A and 49B each show $^1$H-NMR spectrum of [Ir(m6bpy)$_3$].
Figure 49B:
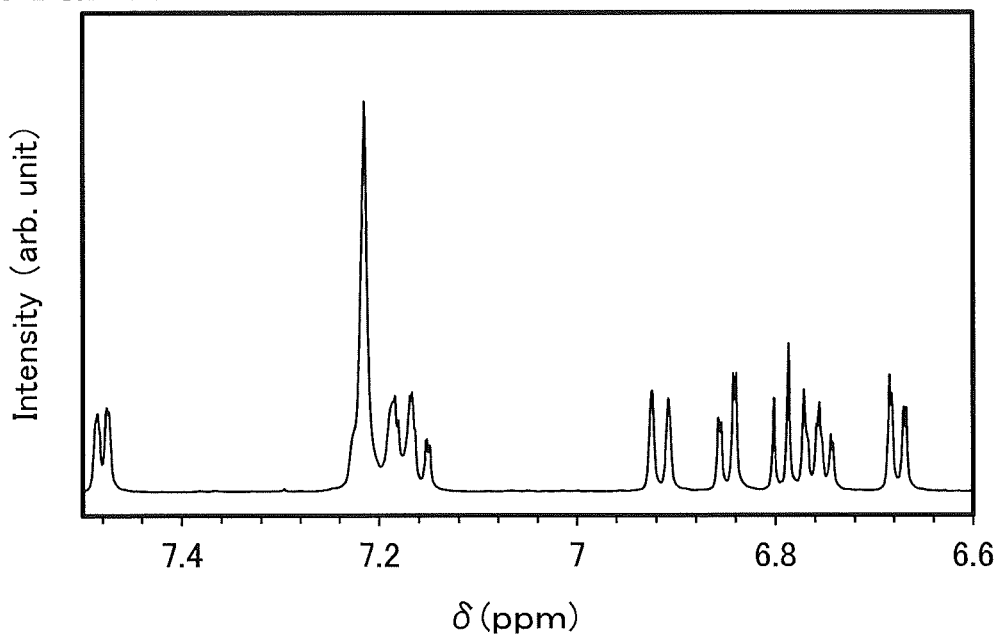

The protons ($^1$H) of the yellow solid that was obtained in Step 3 was measured by nuclear magnetic resonance (NMR). The obtained values are shown below. FIGS. 49A and 49B show the $^1$H NMR charts. These results reveal that [Ir(m6bpy)$_3$], which is the organometallic complex of one embodiment of the present invention, was obtained in this synthesis example.

$^1$H-NMR δ (CD$_2$Cl$_2$): 2.40 (s, 9H), 6.67-6.69 (m, 3H), 6.74-6.80 (m, 6H), 6.85 (d, 3H), 6.92 (d, 3H), 7.15-7.22 (m, 15H), 7.48 (d, 3H).

Figure 50:
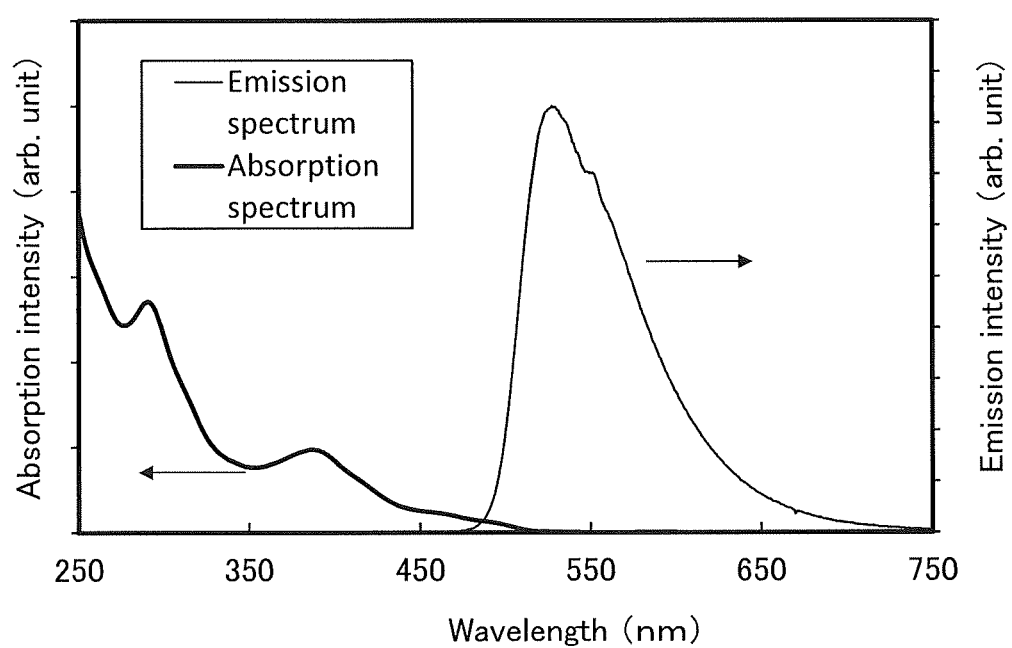
FIG. 50 shows the emission spectrum and the absorption spectrum of [Ir(m6bpy)$_3$].

Next, an ultraviolet-visible absorption spectrum (hereinafter, simply referred to as absorption spectrum) and an emission spectrum of a dichloromethane solution of [Ir(m6bpy)$_3$] were measured. The measurement of the absorption spectrum was conducted at room temperature, for which an ultraviolet and visible spectrophotometer (V550 type manufactured by JASCO Corporation) was used and the dichloromethane solution (0.0093 mmol/L) was put in a quartz cell. In addition, the measurement of the emission spectrum was performed at room temperature in such a manner that an absolute PL quantum yield measurement system (C11347-01 manufactured by Hamamatsu Photonics K.K.) was used, and the deoxidized dichloromethane solution (0.0093 mmol/L) was sealed in a quartz cell under a nitrogen atmosphere in a glove box (LABstar M13 (1250/780) manufactured by Bright Co., Ltd.). FIG. 50 shows measurement results of the absorption spectrum and the emission spectrum. The horizontal axis represents wavelength and the vertical axes represent absorption intensity and emission intensity. Note that the absorption spectrum in FIG. 50 is a result obtained by subtraction of a measured absorption spectrum of only dichloromethane that was put in a quartz cell from the measured absorption spectrum of the dichloromethane solution (0.0093 mmol/L) in a quartz cell.

As shown in FIG. 50, the iridium complex, [Ir(m6bpy)$_3$], had an emission peak at 528 nm, and green light emitted from dichloromethane was observed.

Next, [Ir(m6bpy)$_3$] obtained in this example was analyzed by liquid chromatography mass spectrometry (LC/MS).

In the analysis by LC-MS, liquid chromatography (LC) separation was carried out with UltiMate 3000 produced by Thermo Fisher Scientific K.K., and the MS analysis was carried out with Q Exactive produced by Thermo Fisher Scientific K.K.

In the LC separation, a given column was used at a column temperature of 40° C., and solution sending was performed in such a manner that an appropriate solvent was selected, the sample was prepared by dissolving [Ir(m6bpy)$_3$] in an organic solvent at an arbitrary concentration, and the injection amount was 5.0 µL.

A component with m/z of 924.29, which is an ion derived from [Ir(m6bpy)$_3$], was subjected to the MS$^2$ analysis by a Targeted-MS$^2$ method. For setting of the Targeted-MS$^2$, the mass range of a target ion was set to m/z=924.29±2.0 (isolation window=4) and detection was performed in a positive mode. Measurement was performed with energy (normalized collision energy: NCE) for accelerating a target ion in a collision cell set to 40. The obtained MS spectrum is shown in FIG. 51.

Figure 51:
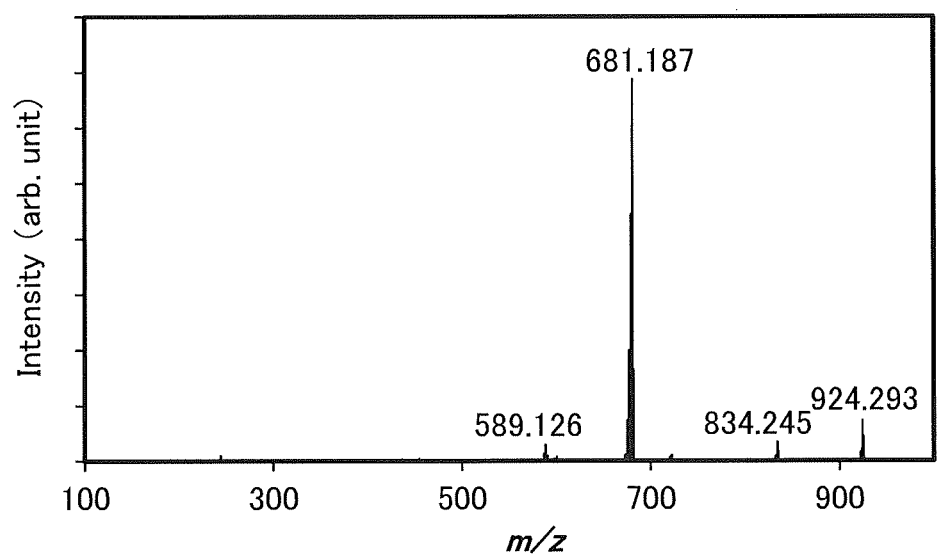
FIG. 51 shows the LC-MS spectrum of [Ir(m6bpy)$_3$].

FIG. 51 shows that product ions of [Ir(m6bpy)$_3$] are mainly detected around m/z=834, 681, and 589. The results in FIG. 51 show characteristics derived from [Ir(m6bpy)$_3$] and therefore can be regarded as important data for identifying [Ir(m6bpy)$_3$] contained in a mixture.

It can be presumed that the product ion around m/z=834 is a cation in a state where a tolyl group is eliminated from [Ir(m6bpy)$_3$], the product ion around m/z=681 is a cation in a state where Hm6bpy is eliminated from [Ir(m6bpy)$_3$], and the product ion around m/z=589 is a cation in a state where Hm6bpy and a tolyl group are eliminated from [Ir(m6bpy)$_3$], which suggests that [Ir(m6bpy)$_3$] includes Hm6bpy and a tolyl group.

This application is based on Japanese Patent Application Serial No. 2016-167185 filed with Japan Patent Office on Aug. 29, 2016, the entire contents of which are hereby incorporated by reference.

What is claimed is:
1. A light-emitting element comprising:
a first electrode;
a second electrode; and
a layer including an organic compound, wherein the layer including an organic compound is located between the first electrode and the second electrode, wherein the layer including an organic compound comprises a light-emitting layer, wherein the light-emitting layer comprises a host material comprising a first organic compound comprising a pyrimidine skeleton, wherein the light-emitting layer comprises a tris iridium complex, wherein on the assumption that there is a rectangle which covers the iridium complex and in which at least one atom of the iridium complex is located over each of four sides when the iridium complex is two-dimensionally seen from a direction of a C3 symmetry axis of the iridium complex, $A \times B/C^2$ is greater than or equal to 3.0 and lower than or equal to 5.7, where A represents a maximum length of a long side of the rectangle, B represents a length of a short side of the rectangle when the length of the long side of the rectangle is A, and C represents a width in the direction of the C3 symmetry axis when the iridium complex is two-dimensionally seen from a normal direction of the C3 symmetry axis, and wherein the iridium complex comprises a ligand comprising a triazole skeleton or a ligand comprising an imidazole skeleton.

2. The light-emitting element according to claim 1, wherein the $A \times B/C^2$ is 4.3.

3. A light-emitting device comprising:
the light-emitting element according to claim 1; and
at least one of a transistor and a substrate.

4. An electronic device comprising:
the light-emitting device according to claim 3; and
at least one of a sensor, an operation button, a speaker, and a microphone.

5. A lighting device comprising:
the light-emitting device according to claim 3; and
a housing.

6. The light-emitting element according to claim 1, wherein the first organic compound further comprises a carbazole skeleton.

7. The light-emitting element according to claim 1, wherein the host material further comprises a second organic compound.

8. The light-emitting element according to claim 7, wherein the second organic compound comprises a carbazole skeleton.

9. The light-emitting element according to claim 7, wherein a weight ratio of the host material to the tris iridium complex is 1:0.10 or higher and 1:0.125 or lower.

10. The light-emitting element according to claim 1, wherein the light-emitting element emits blue light.

11. The light-emitting element according to claim 1, wherein an orientation parameter of the tris iridium complex is lower than or equal to 0.25.

12. An organometallic complex represented by a following formula:

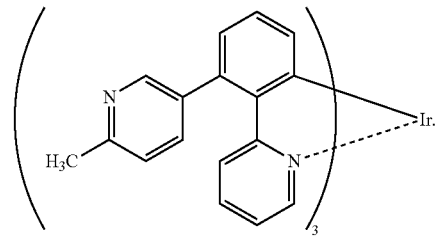

13. A light-emitting element comprising:
a first electrode;
a second electrode; and
a layer including an organic compound, wherein the layer including an organic compound is located between the first electrode and the second electrode, wherein the layer including an organic compound comprises a light-emitting layer, wherein the light-emitting layer comprises a host material comprising a first organic compound comprising a pyrimidine skeleton, wherein the light-emitting layer comprises a tris iridium complex, wherein on the assumption that there is a rectangle which covers the iridium complex and in which at least one atom of the iridium complex is located over each of four sides when the iridium complex is two-dimensionally seen from a direction of a C3 symmetry axis of the iridium complex, $A \times B/C^2$ is greater than or equal to 3.0 and lower than or equal to 4.3, where A represents a maximum length of a long side of the rectangle, B represents a length of a short side of the rectangle when the length of the long side of the rectangle is A, and C represents a width in the direction of the C3 symmetry axis when the iridium complex is two-dimensionally seen from a normal direction of the C3 symmetry axis, and wherein the iridium complex comprises a ligand comprising a pyridine skeleton.

14. The light-emitting element according to claim 13, wherein the first organic compound and/or the second organic compound comprise a carbazole skeleton.

15. The light-emitting element according to claim 14, wherein the first organic compound comprises a pyrimidine skeleton.

16. The light-emitting element according to claim 13, wherein the light-emitting element emits blue light.

17. A light-emitting device comprising:
the light-emitting element according to claim 13; and
at least one of a transistor and a substrate.

* * * * *